(12) United States Patent
Crisman et al.

(10) Patent No.: US 11,802,295 B2
(45) Date of Patent: *Oct. 31, 2023

(54) METHODS FOR TRANSDUCTION AND CELL PROCESSING

(71) Applicant: Juno Therapeutics, Inc., Seattle, WA (US)

(72) Inventors: Ryan L. Crisman, Seattle, WA (US); Chris Ramsborg, Seattle, WA (US); Travis Wood, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1057 days.

This patent is subject to a terminal disclaimer.

(21) Appl. No.: 16/541,083

(22) Filed: Aug. 14, 2019

(65) Prior Publication Data

US 2019/0376084 A1 Dec. 12, 2019

Related U.S. Application Data

(62) Division of application No. 14/932,660, filed on Nov. 4, 2015, now Pat. No. 10,428,351.

(60) Provisional application No. 62/129,023, filed on Mar. 5, 2015, provisional application No. 62/075,801, filed on Nov. 5, 2014.

(51) Int. Cl.
| | | |
|---|---|---|
| *C12N 15/87* | (2006.01) | |
| *C12N 5/0783* | (2010.01) | |
| *C07K 16/28* | (2006.01) | |
| *C07K 14/725* | (2006.01) | |
| *A61K 35/17* | (2015.01) | |
| *B04B 7/08* | (2006.01) | |
| *C12N 15/86* | (2006.01) | |

(52) U.S. Cl.
CPC .............. *C12N 15/87* (2013.01); *A61K 35/17* (2013.01); *B04B 7/08* (2013.01); *C07K 14/7051* (2013.01); *C07K 16/2896* (2013.01); *C12N 5/0636* (2013.01); *C07K 2319/74* (2013.01); *C12N 15/86* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,163,519 A | 8/1979 | Stabile |
| 4,452,773 A | 6/1984 | Molday |
| 4,690,915 A | 9/1987 | Rosenberg |
| 4,795,698 A | 1/1989 | Owen et al. |
| 4,950,401 A | 8/1990 | Unger et al. |
| 5,200,084 A | 4/1993 | Liberti et al. |
| 5,219,740 A | 6/1993 | Miller et al. |
| 5,437,998 A | 8/1995 | Schwarz et al. |
| 5,911,983 A | 6/1999 | Barranger et al. |
| 6,040,177 A | 3/2000 | Riddell et al. |
| 6,123,655 A | 9/2000 | Fell |
| 6,207,453 B1 | 3/2001 | Maass et al. |
| 6,410,319 B1 | 6/2002 | Raubitschek et al. |
| 6,451,995 B1 | 9/2002 | Cheung et al. |
| 6,733,433 B1 | 5/2004 | Fell |
| 7,001,513 B2 | 2/2006 | Bell |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 8,324,353 B2 | 12/2012 | Jensen |
| 8,389,282 B2 | 3/2013 | Sadelain et al. |
| 8,399,645 B2 | 3/2013 | Campana et al. |
| 8,497,118 B2 | 7/2013 | Jensen |
| 8,747,289 B2 | 6/2014 | Coelho |

(Continued)

FOREIGN PATENT DOCUMENTS

| | | |
|---|---|---|
| CN | 102329776 A | 1/2012 |
| EP | 0452342 | 10/1991 |

(Continued)

OTHER PUBLICATIONS

US 8,252,592 B2, 08/2012, Sadelain (withdrawn)
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.
Ayuk, et al., "Establishment of an optimised gene transfer protocol for human primary T lymphocytes according to clinical requirements," Gene Therapy (1999) 6: 1788-1792.

(Continued)

*Primary Examiner* — Allison M Fox
*Assistant Examiner* — Kimberly A Aron
(74) *Attorney, Agent, or Firm* — MORRISON & FOERSTER LLP

(57) ABSTRACT

Provided are methods, systems, and kits for cell processing, e.g., for therapeutic use, such as for adoptive cell therapy. The provided methods include transduction methods, in which cells and virus are incubated under conditions that result in transduction of the cells with a viral vector. The incubation in some embodiments is carried out in an internal cavity of a generally rigid centrifugal chamber, such as a cylindrical chamber made of hard plastic, the cavity of which may have a variable volume. The methods include other processing steps, including those carried out in such a chamber, including washing, selection, isolation, culture, and formulation. In particular, the disclosure relates to method providing advantages over available processing methods, such as available methods for large-scale processing. Such advantages include, for example, reduced cost, streamlining, increased efficacy, increased safety, and increased reproducibility among different subjects and conditions.

26 Claims, 13 Drawing Sheets

(56) References Cited

U.S. PATENT DOCUMENTS

| | | | |
|---|---|---|---|
| 8,802,374 B2 | 8/2014 | Jensen | |
| 8,815,597 B2 | 8/2014 | Chono et al. | |
| 10,428,351 B2 | 10/2019 | Crisman et al. | |
| 2002/0131960 A1 | 9/2002 | Sadelain et al. | |
| 2003/0170238 A1 | 9/2003 | Gruenberg et al. | |
| 2008/0171951 A1 | 7/2008 | Fell | |
| 2011/0003380 A1 | 1/2011 | Miltenyi et al. | |
| 2011/0207225 A1* | 8/2011 | Mehta | C12N 13/00 435/173.6 |
| 2013/0095993 A1 | 4/2013 | Isaksson et al. | |
| 2013/0149337 A1 | 6/2013 | Cooper et al. | |
| 2013/0287748 A1 | 10/2013 | June et al. | |
| 2014/0080212 A1 | 3/2014 | Asgari | |
| 2016/0199412 A1 | 7/2016 | Tareen | |
| 2016/0250258 A1 | 9/2016 | Delaney et al. | |
| 2017/0037369 A1 | 2/2017 | Ramsborg et al. | |

FOREIGN PATENT DOCUMENTS

| | | |
|---|---|---|
| EP | 0995802 | 4/2000 |
| EP | 2537416 | 12/2012 |
| EP | 2594632 | 5/2013 |
| JP | 2008048651 A | 3/2008 |
| WO | WO 1992/008796 | 5/1992 |
| WO | WO 1994/028143 | 12/1994 |
| WO | WO 1997/021824 | 6/1997 |
| WO | WO 2000/014257 | 3/2000 |
| WO | WO 2000/038762 | 7/2000 |
| WO | WO 2003/009889 | 2/2003 |
| WO | WO 2009/072003 | 6/2009 |
| WO | WO 2010/008579 | 1/2010 |
| WO | WO 2011/116221 | 9/2011 |
| WO | WO 2012/129514 | 9/2012 |
| WO | WO 2013/071154 | 5/2013 |
| WO | WO 2013/072288 | 5/2013 |
| WO | WO 2013/123061 | 8/2013 |
| WO | WO 2013/126726 | 8/2013 |
| WO | WO 2013/127964 | 9/2013 |
| WO | WO 2013/138465 | 9/2013 |
| WO | WO 2013/166321 | 11/2013 |
| WO | WO 2014/027016 | 2/2014 |
| WO | WO 2014/031687 | 2/2014 |
| WO | WO 2014/055668 | 4/2014 |
| WO | WO 2015/162211 | 10/2015 |
| WO | WO 2016/073602 | 5/2016 |

OTHER PUBLICATIONS

Bahnson et al., "Centrifugal enhancement of retroviral mediated gene transfer," J Virol Methods (1995) 54(2-3):131-43.

Biosafe SA, U.S. Food and Drug Administration 510(k) Submission Summary—BK110022, Oct. 20, 2011, retrieved from the internet at http://www.fda.gov/downloads/BiologicsBloodVaccines/BloodBloodProducts/ApprovedProducts/SubstantiallyEquivalent510kDeviceInformation/UCM278385.pdf.

Biosafe, SEPAX Cell Processing System Operator's Manual, release date Jan. 17, 2008, 208 pages.

Boris-Lawrie et al., "Recent advances in retrovirus vector technology," Cur. Opin. Genet. Develop. (1993) 3:102-109.

Brentjens et al., "CD19-targeted T cells rapidly induce molecular remissions in adults with chemotherapy-refractory acute lymphoblastic leukemia," Sci Transl Med. (2013) 5(177).

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10):1137-46.

Chen et al., "The Woodchuck hepatitis virus X gene is important for establishment of virus infection in Woodchucks," J Virol. Mar. 1993;67(3):1218-1226.

Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.

Davila et al., "CD19 CAR-targeted T cells induce long-term remission and B Cell Aplasia in an immunocompetent mouse model of B cell acute lymphoblastic leukemia," PLoS ONE (2013) 8(4):e61338.

Fedorov et al., "PD-1- and CTLA-4-based inhibitory chimeric antigen receptors (iCARs) divert off-target immunotherapy responses," Sci. Transl. Medicine (2013) 5(215):215ra172.

Herman et al., "The VITAL assay: a versatile fluorometric technique for assessing CTL- and NKT-mediated cytotoxicity against multiple targets in vitro and in vivo," J. Immunological Methods (2004) 285(1):25-40.

International Search Report and Written Opinion for PCT/US2015/059030, dated May 12, 2016, 21 pages.

Invitation to Pay Additional Fees for PCT/US2015/059030, dated Feb. 9, 2016, 11 pages.

Kalos et al., "T cells with chimeric antigen receptors have potent antitumor effects and can establish memory in patients with advanced leukemia," Sci Transl Med (2011) 3(95):95ra73.

Klebanoff et al., "Sorting through subsets: which T-cell populations mediate highly effective adoptive immunotherapy?" J Immunother. (2012) 35(9):651-660.

Kochenderfer et al., "Construction and preclinical evaluation of an anti-CD19 chimeric antigen receptor," J. Immunotherapy (2009) 32(7):689-702.

Kochenderfer et al., "Treating B-cell cancer with T cells expressing anti-CD19 chimeric antigen receptors," Nature Reviews Clinical Oncology (2013) 10, 267-276.

Koste et al., "T-cell receptor transfer into human T cells with ecotropic retroviral vectors," Gene Therapy (2014) 21:533-538.

Lupton S. D. et al., "Dominant positive and negative selection using a hygromycin phosphotransferase-thymidine kinase fusion gene," Mol. and Cell Biol. (1991) 11:6.

Miller et al., "Improved retroviral vectors for gene transfer and expression," BioTechniques (1989) 7:980-990.

Miller et al., "Retrovirus packaging cells," Human Gene Therapy (1990) 1:5-14.

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.

Nishimura et al., "Enhanced efficiency by centrifugal manipulation of adenovirus-mediated interleukin 12 gene transduction into human monocyte-derived dendritic cells," Hum Gene Ther. (2001) 12(4):333-46.

Nyberg-Hoffman et el., "Sensitivity and reproducibility in adenoviral infectious titer determination," Nat Med. (1997) 3(7): 808-11.

O'Doherty et al., "Human immunodeficiency virus type 1 spinoculation enhances infection through virus binding," J Virol., Nov. 2000;74(21):10074-80.

Park et al., "Treating cancer with genetically engineered T cells," Trends Biotechnol. (2011) 29(11):550-557.

Raviv et al., "Cell Therapies—The Challenges & Possible Solutions for Transferring Cell Therapy From the Bench to the Industry," Drug Development & Delivery. Mar. 2014;14(2):58-63.

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

Rosenberg, et al., "Cell transfer immunotherapy for metastatic solid cancer—what clinicians need to know," Nat Rev Clin Oncol. (2011) 8(10):577-85).

Sadelain et al., "The basic principles of chimeric antigen receptor design," Cancer Discov. (2013) 3(4):388-398.

Scarpa et al., "Characterization of recombinant helper retroviruses from Moloney-based vectors in ecotropic and amphotropic packaging cell lines," Virology (1991) 180:849-852.

Sepax 2 Brochure, retrieved from the internet at http://www.haemotec.co.za/downloads/BiosafeSepaxAutomatedCellProcessing-Sepax2.pdf retrieved on Oct. 31, 2014.

(56) References Cited

OTHER PUBLICATIONS

Sepax® System introduction brochure, retrieved from the Internet at http://diamedil.info/Sepax_system_introduction.pdf retrieved on Oct. 31, 2014.
Spencer, "Enhancing lentiviral transduction efficiency," Sigma-Aldrich, Retrieved from the Internet:http://www.sigmaaldrich.com/technical-documents/articles/life-science-innovations/enhancing-lentiviral.html [retrieved on Oct. 5, 2014].
Tayi, "Quantitative analysis of retrovirus-mediated gene transfer into mammalian cells," Thesis, Publicly available (2010); https://dx.doi.org/10.14288/1.0058879.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10):928-933.
Tsukahara et al., "CD19 target-engineered T-cells accumulate at tumor lesions in human B-cell lymphoma xenograft mouse models," Biochem Biophys Res Commun (2013) 438(1):84-9.
Turtle et al., "Engineered T cells for anti-cancer therapy," Curr. Opin. Immunol. (2012) 24(5):633-39.
Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1997) 11:223-232.
Wu et al., "Adoptive T-cell therapy using autologous tumor-infiltrating lymphocytes for metastatic melanoma: current status and future outlook," Cancer (2012) 18(2):160-75.
Xu, "Viral and plasmid transduction systems: methods to modify immune cells for cancer immunotherapy," Biology Education Centre and Department of Immunology, Genetics and Pathology (IGP), Rudbeck Laboratory, Uppsala University (2011) 29 pages.
Yi et al., "T-cell exhaustion: characteristics, causes and conversion," Immunology Apr. 2010: 129(4):474-81.

* cited by examiner

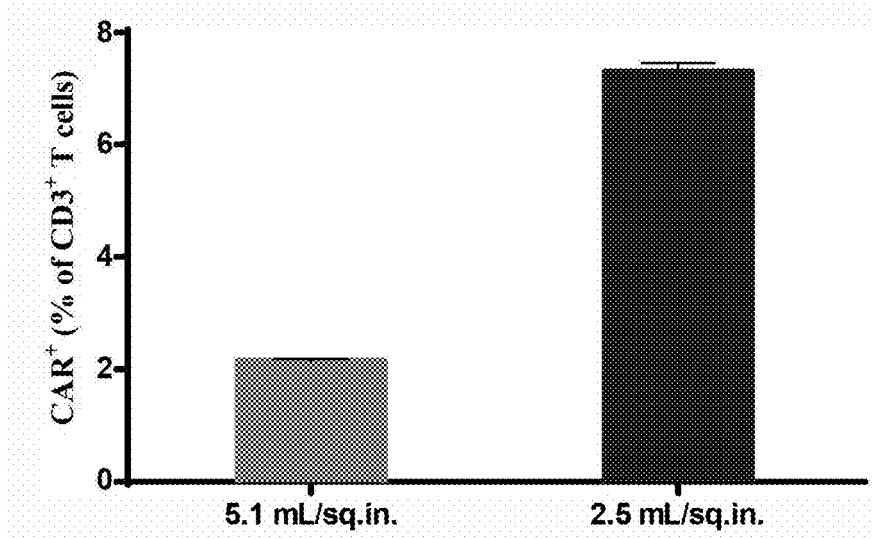

METHODS FOR TRANSDUCTION AND CELL PROCESSING

CROSS-REFERENCE TO RELATED APPLICATIONS

This application is a divisional of U.S. Ser. No. 14/932,660 filed Nov. 4, 2015, entitled "Methods for Transduction and Cell Processing," which claims priority from U.S. provisional application No. 62/075,801 filed Nov. 5, 2014, entitled "Methods for Transduction and Cell Processing," and U.S. provisional application No. 62/129,023 filed Mar. 5, 2015, entitled "Methods for Transduction and Cell Processing," the contents of which are incorporated by reference in their entirety.

FIELD

The present disclosure relates to cell processing for therapeutic use, such as for adoptive cell therapy. The provided methods generally include transduction methods, in which cells and viral vector particles are incubated under conditions that result in transduction of the cells with a viral vector. The incubation may be carried out in an internal cavity of a generally rigid centrifugal chamber, such as a cylindrical chamber made of hard plastic. The methods include other processing steps, including those carried out in such a chamber, including washing, selection, isolation, culture, and formulation. In particular, the disclosure relates to method providing advantages over available processing methods, such as available methods for large-scale processing. Such advantages include, for example, reduced cost, streamlining, increased efficacy, increased safety, and increased reproducibility among different subjects and conditions.

BACKGROUND

Certain methods are available for cell processing, including large-scale methods and methods for use in preparation of cells for adoptive cell therapy. For example, methods for viral vector transfer, e.g., transduction, selection, isolation, stimulation, culture, washing, and formulation, are available. Available methods have not been entirely satisfactory. Improved methods are needed, for example, for large-scale processing, e.g., transduction, of cells for adoptive cell therapy. For example, methods are needed to improve efficiency and reproducibility, and to reduce time, cost, handling, complexity, and/or other parameters associated with such production. Among the provided embodiments are methods, systems, and kits addressing such needs.

SUMMARY

Provided are methods for cell processing, such as for transfer of viral vectors and/or immunoaffinity-based selection of cells. In some embodiments, the cells are for use in cell therapy, such primary cells prepared for autologous or allogeneic transfer, e.g., in adoptive cell therapy. The methods may include additional cell processing steps, such as cell washing, isolation, separation.

In some embodiments, the methods are carried out by incubating, in a vessel, such as an internal cavity of a centrifugal chamber, a composition (deemed an input composition), which contains cells and viral vector particles, the viral particles containing a recombinant viral vector, thereby generating an output composition that contains a plurality of the cells transduced with the viral vector. The centrifugal chamber typically is rotatable around an axis of rotation. The axis of rotation in some embodiments is vertical. The chamber typically includes an end wall, a side wall extending from the end wall, such as a substantially rigid side wall, and at least one opening, such as an inlet/outlet or an inlet and an outlet. At least a portion of the side wall generally surrounds the internal cavity. The at least one opening (e.g., the inlet/outlet or the inlet and the outlet) is capable of permitting intake of liquid into the internal cavity and expression of liquid from the cavity. The at least one opening in some embodiments is coaxial with the chamber and in some embodiments is in an end wall of the chamber. The side wall may be a curvilinear, e.g., cylindrical or generally cylindrical.

In some embodiments, the methods include incubating, in an internal cavity of a centrifugal chamber, an input composition containing cells and viral particles containing a recombinant viral vector, wherein said centrifugal chamber is rotatable around an axis of rotation and includes an end wall, a substantially rigid side wall extending from said end wall, and at least one opening, at least a portion of said side wall surrounding said internal cavity and said at least one opening being capable of permitting intake of liquid into said internal cavity and expression of liquid from said cavity, wherein the centrifugal chamber is rotating around said axis of rotation during at least a portion of the incubation and the method generates an output composition containing a plurality of the cells transduced with the viral vector.

In some embodiments, the centrifugal chamber further includes a movable member, such as a piston. In such embodiments, the internal cavity is generally one of variable volume, e.g., a cavity of variable volume defined by the end wall, the side wall, and the movable member, e.g., the piston, such that the movable member is capable of moving within the chamber (such as axially within the chamber) to vary the internal volume of the cavity. In some embodiments, liquid is moved in and out of the chamber alternatively by way of a pump, syringe, and/or motor, or other device for intake and expressing liquid or gas, which for example pulls liquid from the cavity and/or pushes liquid in, while the volume of the cavity itself remains constant.

In some embodiments, the methods include incubating, in an internal cavity of a centrifugal chamber, an input composition containing cells and a viral particle containing a recombinant viral vector, said centrifugal chamber being rotatable around an axis of rotation and comprising an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity, wherein the centrifugal chamber is rotating around the axis of rotation during at least a portion of the incubation, the total liquid volume of said input composition present in said cavity during rotation of said centrifugal chamber is no more than about 5 mL per square inch of the internal surface area of the cavity and the method generates an output composition comprising a plurality of the cells transduced with the viral vector.

The chamber may comprise two end walls. In some such embodiments, one end wall together with other features defines the internal cavity, while the other is outside of the cavity. In some embodiments, the cavity is bound by both end walls.

The at least one opening may comprise: an inlet and an outlet, respectively capable of permitting said intake and expression, or a single inlet/outlet, capable of permitting said intake and said expression.

Typically, the incubation is carried out at least in part under rotation of the chamber, such as under centrifugal force or acceleration. Thus, the methods in some embodiments further include effecting rotation of the centrifugal chamber, such as around its axis of rotation, during at least a portion of the incubation.

In some of any such embodiments, said rotating includes rotation at a relative centrifugal force (RCF) at an internal surface of the side wall of the cavity and/or at a surface layer of the cells of greater than at or about 200 g, greater than at or about 300 g, or greater than at or about 500 g. In some of any such embodiments, said rotating includes rotation at a relative centrifugal force at an internal surface of the side wall of the cavity and/or at a surface layer of the cells that is: at or about 1000 g, 1500 g, 2000 g, 2100 g, 2200 g, 2500 g or 3000 g; or at least at or about 1000 g, 1500 g, 2000 g, 2100 g, 2200 g, 2500 g, or 3000 g. In some of any such embodiments, said rotating includes rotation at a relative centrifugal force at an internal surface of the side wall of the cavity and/or at a surface layer of the cells that is: between or between about 1000 and 3600, 1000 and 3200, 1000 and 2800, 1000 and 2000, 1000 and 1600, 1600 and 3600, 1600 and 3200, 1600 and 2800, 1600 and 2000, 2000 and 3600, 2000 and 3200, 2000 and 2800, 2800 and 3600, 2800 and 3200, 3200 and 3600, each inclusive; or at least at or about 2000 g, 2100, 2200 g, 2400 g, 2600 g, 2800 g, 3000 g, 3200 g or 3600 g; or at or about 2000 g, 2100 g, 2200 g, 2400 g, 2600 g, 2800 g, 3000 g, 3200 g or 3600 g.

In some of any such embodiments, the at least a portion of the incubation during which the chamber is rotating is for a time that is: greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes; or between or between about 5 minutes and 60 minutes, 10 minutes and 60 minutes, 15 minutes and 60 minutes, 15 minutes and 45 minutes, 30 minutes and 60 minutes or 45 minutes and 60 minutes, each inclusive.

In some embodiments, the input composition (or the number of cells) in the cavity during the incubation, e.g., at any one time or during the entire incubation, and/or processed by the methods, includes at or about or at least about $1 \times 10^6$, $5 \times 10^6$, $1 \times 10^7$, $5 \times 10^7$, $1 \times 10^8$ or $5 \times 10^8$ of the cells.

In some of any such embodiments, said input composition in the cavity contains at least at or about $1 \times 10^7$ of said cells, at least at or about $2 \times 10^7$ of said cells, $3 \times 10^7$ of said cells, at least at or about $4 \times 10^7$ of said cells, at least at or about $5 \times 10^7$ of said cells, at least at or about $6 \times 10^7$ of said cells, at least at or about $7 \times 10^7$ of said cells, at least at or about $8 \times 10^7$ of said cells, at least at or about $9 \times 10^7$ of said cells, at least at or about $1 \times 10^8$ of said cells, at least at or about $2 \times 10^8$ of said cells, at least at or about $3 \times 10^8$ of said cells or at least at or about $4 \times 10^8$ of said cells.

In some embodiments, the internal surface area of the cavity is at least at or about $1 \times 10^9$ µm² or $1 \times 10^{10}$ µm², and/or the length of the side wall in the direction extending from the end wall is at least about 5 cm and/or at least about 8 cm; and/or the internal cavity has a radius of at least about 2 cm at at least one cross-section.

In some embodiments, the input composition includes at least or about 1 infectious unit (IU) per one of the cells, at least or about 2 IU per one of the cells, at least or about 3 IU per one of the cells, at least or about 4 IU per one of the cells, at least or about 5 IU per one of the cells, at least or about 10 IU per one of the cells, at least or about 20 IU per one of the cells, at least or about 30 IU per one of the cells, at least or about 40 IU per one of the cells, at least or about 50 IU per one of the cells, or at least or about 60 IU per one of the cells. In some embodiments, the input composition includes at or about 1 infectious unit (IU) per one of the cells, at or about 2 IU per one of the cells, at or about 3 IU per one of the cells, at or about 4 IU per one of the cells, at or about 5 IU per one of the cells, at or about 10 IU per one of the cells, at or about 20 IU per one of the cells, at or about 30 IU per one of the cells, at or about 40 IU per one of the cells, at or about 50 IU per one of the cells, or at or about 60 IU per one of the cells.

In some embodiments, the average liquid volume or maximum liquid volume of the input composition, composition with viral vector particles and cells, and/or any liquid composition present in the cavity during the incubation is no more than about 10, 5, or 2.5 milliliters (mL) per square inch of the internal surface area of the cavity during the incubation. In some embodiments, the maximum total volume of such liquid composition present in the cavity at any one time during the incubation is no more than 2 times, no more than 10 times, no more than 100 times, no more than 500 times or no more than 1000 times the total volume of the cells. In some embodiments, the total volume of cells is the total volume of a pellet of the cells. In some embodiments, the total volume of cells is the volume of a monolayer of the cells, such as a monolayer of cells present on the internal surface in the cavity during rotation of the centrifugal chamber.

In some embodiments, the liquid volume of the input composition occupies all or substantially all of the volume of the internal cavity during at least a portion of the incubation. In other embodiments, during at least a portion of the incubation, the liquid volume of the input composition occupies only a portion of the volume of the internal cavity, the volume of the cavity during this at least a portion further comprising a gas, which is taken into the cavity, e.g., via said at least one opening or another opening, prior to or during the incubation.

In some of any such embodiments, the liquid volume of said input composition present in said cavity during said rotation is between or between about 0.5 mL per square inch of the internal surface area of the cavity (mL/sq.in) and 5 mL/sq.in, 0.5 mL/sq.in. and 2.5 mL/sq.in., 0.5 mL/sq.in. and 1 mL/sq.in., 1 mL/sq.in. and 5 mL/sq.in., 1 mL/sq.in. and 2.5 mL/sq.in. or 2.5 mL/sq.in. and 5 mL/sq.in.

In some of any such embodiments, the maximum total liquid volume of said input composition present in said cavity at any one time during said incubation is no more than 2 times, no more than 10 times, or no more than 100 times, the total volume of said cells in said cavity or the average volume of the input composition over the course of the incubation is no more than 2, 10, or 100 times the total volume of cells in the cavity.

In some of any such embodiments, the maximum volume of said input composition present in said cavity at any one time during said incubation or the average volume over the course of the incubation is no more than at or about 2 times, 10 times, 25 times, 50 times, 100 times, 500 times, or 1000 times the volume of a monolayer of said cells formed on the inner surface of said cavity during rotation of said chamber at a force of at or about 2000 g at an internal surface of the side wall.

In some of any such embodiments, the liquid volume of the input composition is no more than 20 mL, no more than 40 mL, no more than 50 mL, no more than 70 mL, no more than 100 mL, no more than 120 mL, no more than 150 mL or no more than 200 mL.

In some of any such embodiments, during at least a portion of the incubation in the chamber or during the rotation of the chamber, the liquid volume of the input composition occupies only a portion of the volume of the internal cavity of the chamber, the volume of the cavity during said at least a portion or during said rotation further comprising a gas, said gas taken into said cavity via said at least one opening, prior to or during said incubation.

In some embodiments, the centrifugal chamber includes a movable member, whereby intake of gas into the centrifugal chamber effects movement of the movable member to increase the volume of the internal cavity of the chamber, thereby decreasing the total liquid volume of said input composition present in said cavity during rotation of said centrifugal chamber per square inch of the internal surface area of the cavity compared to the absence of gas in the chamber.

In some embodiments, the number of cells in the cavity during the incubation is at or about the number of the cells sufficient to form a monolayer on the internal surface of the cavity during rotation of the centrifugal chamber at a force of at or about 2000 g and/or is no more than 1.5 times or 2 times such a number of the cells.

In some of any such embodiments, the number of said cells in said input composition is at or about the number of said cells sufficient to form a monolayer on the surface of said cavity during rotation of said centrifugal chamber at a force of at or about 2000 g at an internal surface of the side wall; and/or the number of said cells in said input composition is no more than 1.5 times or 2 times the number of said cells sufficient to form a monolayer on the surface of said cavity during rotation of said centrifugal chamber at a force of at or about 2000 g at an internal surface of the side wall.

In some embodiments, the centrifugation is for a duration of between 120 and 7200 seconds, such as between 120 and 3600 seconds, including values inclusive or within the range, such as whole-minute values inclusive or within the range.

In some embodiments, the methods include a) providing to an internal cavity of a centrifugal chamber that has an internal surface area of at least at or about $1 \times 10^9$ μm$^2$ or at least at or about $1 \times 10^{10}$ μm$^2$; i) an input composition including cells and viral particles containing a recombinant viral vector, wherein: the number of cells in the input composition is at least $1 \times 10^7$ cells, and the viral particles are present in the input composition at at least at or about 1 infectious unit (IU) per one of said cells, and the input composition contains a liquid volume that is less than the maximum volume of the internal cavity of the centrifugal chamber; and ii) gas, at a volume that is up to the remainder of the maximum volume of the internal cavity of the centrifugal chamber; and b) incubating the input composition, wherein at least a portion of the incubation is carried out in said internal cavity of said centrifugal chamber while effecting rotation of said centrifugal chamber; and wherein the method generates an output composition containing a plurality of the cells transduced with the viral vector.

In some embodiments, the number of cells is at least or about $50 \times 10^6$ cells; $100 \times 10^6$ cells; or $200 \times 10^6$ cells; and/or the viral particles are present at at least 1.6 IU/cell, 1.8 IU/cell, 2.0 IU/cell, 2.4 IU/cell, 2.8 IU/cell, 3.2 IU/cell or 3.6 IU/cell, 4.0 IU/cell, 5.0 IU/cell, 6.0 IU/cell, 7.0 IU/cell, 8.0 IU/cell, 9.0 IU/cell or 10.0 IU/cell.

In some of any such embodiments, the liquid volume of the input composition is less than or equal to 200 mL, less than or equal to 100 mL or less than or equal to 50 mL or less than or equal to 20 mL. In some of any such embodiments, the volume of gas is up to 200 mL, up to 180 mL, up to 140 mL or up to 100 mL.

In some of any such embodiments, said rotation is at a relative centrifugal force at an internal surface of the side wall of the cavity or at a surface layer of the cells of at least at or about 1000 g, 1500 g, 2000 g, 2400 g, 2600 g, 2800 g, 3000 g, 3200 g or 3600 g.

In some embodiments, the methods are for large-scale processing.

In some embodiments, the composition in the cavity (e.g., input composition) includes at least 50 mL, at least 100 mL, or at least 200 mL, liquid volume, and/or at least or about 1 million cells per cm$^2$ of the internal surface area of the cavity during at least a portion of said incubation.

In some embodiments, the maximum liquid volume of the input composition present in the cavity at any one time during said incubation is no more than at or about 2 times, 10 times, 25 times, 50 times, 100 times, 500 times, or 1000 times the volume of a monolayer of said cells formed on the inner surface of said cavity during rotation of said chamber, e.g., at a force, e.g., effective force, of at or about 2000 g.

In some embodiments, the rotation of the chamber during at least a portion of the incubation is at a force of greater than at or about 200 g, greater than at or about 300 g, or greater than at or about 500 g, such as greater than at or about 1000 g, 1500 g, 2000 g, 2500 g, 3000 g, or 3200 g, at an internal wall of the cavity of the centrifugal chamber and/or a layer, e.g., surface layer, of the cells. In some embodiments, the force is at least at or about 1000 g, 1500 g, 2000 g, or 2500 g, 3000 g or 3200 g. In some embodiments, the force is at or about 2100 g, 2200 g or 3000 g.

In some embodiments, the methods include incubating an input composition containing cells and viral particles containing a recombinant viral vector, at least a portion of said incubating being carried out under rotating conditions, thereby generating an output composition containing a plurality of the cells transduced with the viral vector, wherein said input composition contains greater than or about 20 mL, 50 mL, at least 100 mL, or at least 150 mL in volume, and/or said input composition comprises at least $1 \times 10^8$ cells; and said rotating conditions comprise a relative centrifugal force on a surface layer of the cells of greater than about 1500 g.

In some embodiments of the methods, at least 25% or at least 50% of said cells in the output composition are transduced with said viral vector; and/or at least 25% or at least 50% of said cells in the output composition express a product of a heterologous nucleic acid contained within said viral vector.

In some of any such embodiments, said incubation is carried out in a cavity of a centrifugal chamber and the number of said cells in said input composition is at or about the number of said cells sufficient to form a monolayer or a bilayer on the inner surface of said cavity during said rotation.

In some embodiments, said centrifugal chamber includes an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity, In some embodiments, said centrifugal chamber further includes a movable member and said internal cavity is a cavity of variable volume defined by said end wall, said substantially rigid side wall, and said movable member, said movable member being capable of moving within the chamber to vary the internal volume of the cavity.

In some of any such embodiments, the input composition in said cavity contains a liquid volume of at least 20 mL or at least 50 mL and at or about 1 million cells per cm$^2$ of the internal surface area of the cavity during at least a portion of said incubation.

In some of any such embodiments, a further portion of the incubation is carried out outside of the centrifugal chamber and/or without rotation, said further portion carried out subsequent to the at least a portion carried out in the chamber and/or with rotation.

In some of any such embodiments, the at least a portion of the incubation carried out in the cavity of the centrifugal chamber and/or the further portion of the incubation is effected at or at about 37° C.±2° C.

In some of any such embodiments, the incubation further includes transferring at least a plurality of the cells to a container during said incubation and said further portion of the incubation is effected in the container. In some embodiments, the transferring is performed within a closed system, wherein the centrifugal chamber and container are integral to the closed system.

In some of any such embodiments, the incubation is carried out for a time between at or about 1 hour and at or about 96 hours, between at or about 4 hours and at or about 72 hours, between at or about 8 hours and at or about 48 hours, between at or about 12 hours and at or about 36 hours, between at or about 6 hours and at or about 24 hours, between at or about 36 hours and at or about 96 hours, inclusive; or the further portion of the incubation is carried out for a time between at or about 1 hour and at or about 96 hours, between at or about 4 hours and at or about 72 hours, between at or about 8 hours and at or about 48 hours, between at or about 12 hours and at or about 36 hours, between at or about 6 hours and at or about 24 hours, between at or about 36 hours and at or about 96 hours, inclusive.

In some of any such embodiments, the incubation or further portion of the incubation is carried out for a time that is no more than 48 hours, no more than 36 hours or no more than 24 hours; or the further portion of the incubation is carried out for a time that is no more than 48 hours, no more than 36 hours or no more than 24 hours.

In some of any such embodiments, the incubation is performed in the presence of a stimulating agent; and/or the further portion of the incubation is performed in the presence of a stimulating agent.

In some of any such embodiments, the incubation is carried out for a time that is no more than 24 hours; the cells in the composition have not been subjected to a temperature of greater than 30° C. for more than 24 hours; and/or the incubation is not performed in the presence of a stimulating agent.

In some of any such embodiments, the stimulating agent is an agent capable of inducing proliferation of T cells, CD4+ T cells and/or CD8+ T cells.

In some of any such embodiments, the stimulating agent is a cytokine selected from among IL-2, IL-15 and IL-7.

In some of any such embodiments, the output composition containing transduced cells contains at least 1×10$^7$ cells or at least 5×10$^7$ cells.

In some of any such embodiments, the output composition containing transduced cells contains at least 1×10$^8$ cells, 2×10$^8$ cells, 4×10$^8$ cells, 6×10$^8$, 8×10$^8$ cells or 1×10$^9$ cells.

In some of any such embodiments, the cells are T cells. In some embodiments, the T cells are unfractionated T cells, isolated CD4+ T cells and/or isolated CD8+ T cells.

In some of any such embodiments, the method results in integration of the viral vector into a host genome of one or more of the at least a plurality of cells and/or into a host genome of at least at or about 20% or at least at or about 30% or at least at or about 40% of the cells in the output composition.

In some of any such embodiments, at least 2.5%, at least 5%, at least 6%, at least 8%, at least 10%, at least 20%, at least 25%, at least 30%, at least 40%, at least 50%, or at least 75% of said cells in said input composition are transduced with said viral vector by the method; and/or at least 2.5%, at least 5%, at least 6%, at least 8%, at least 10%, at least 20%, at least 25%, at least 30%, at least 40%, at least 50%, or at least 75% of said cells in said output composition are transduced with said viral vector; and/or at least 2.5%, at least 5%, at least 6%, at least 8%, at least 10%, at least 20%, at least 25%, at least 30%, at least 40%, at least 50%, or at least 75% of said cells in said output composition express a product of a heterologous nucleic acid contained within said viral vector.

Particular embodiments include methods of transduction carried out by incubating an input composition comprising cells and viral vector particles under rotating conditions, whereby a plurality of the cells are inoculated for transduction with the viral vector, wherein the input composition includes a total volume greater than 50 mL, such as at least 100 mL, or at least 150 mL in volume, and/or said input composition comprises at least 1×10$^8$ cells; and the rotating conditions comprise centrifugal force of greater than about 1500 g. In some such embodiments, the incubation is carried out in a cavity of a centrifugal chamber and the number of said cells in said input composition is at or about the number of said cells sufficient to form a monolayer on the inner surface of the cavity during the rotation. In some such embodiments, at least 25% or at least 50% of said cells are transduced with the viral vector.

In some embodiments, the methods result in at least 2.5%, at least 5%, at least 6%, at least 8%, at least 10%, at least 20%, at least 25%, at least 30%, at least 40%, at least 50%, or at least 75% of said cells in said input composition being transduced with the viral vector, and/or produce an output composition in which at least 10%, at least 25%, at least 30%, at least 40%, at least 50%, or at least 75% of the cells are transduced with the vector and/or express a recombinant product encoded by the vector. In some embodiments, transduction efficiency is expressed for a particular input amount or relative amount of virus. For example, in some embodiments, such efficiencies are achieved by the methods for an input composition comprising a virus at a ratio of about 1 or about 2 IU per cells.

In some embodiments, among all the cells in said output composition produced by the methods, the average copy number of the recombinant viral vector is no more than about 10, no more than about 5, no more than about 2.5, or no more than about 1.5. In some embodiments, among the cells in the output composition that contain the recombinant viral vector, the average copy number of the vector is no more than about 5, no more than about 2, no more than about 1.5, or no more than about 1.

In some of any such embodiments, among all the cells in said output composition that contain the recombinant viral vector or into which the viral vector is integrated, the average copy number of said recombinant viral vector is no more than about 10, no more than about 5, no more than about 2.5, or no more than about 1.5; or among the cells in the output composition, the average copy number of said vector is no more than about 2, no more than about 1.5, or no more than about 1.

In some embodiments, the centrifugal chamber is integral to a closed system, for example, where the closed system includes the chamber and at least one tubing line operably linked to the at least one opening via at least one connector, such that liquid and gas are permitted to move between said cavity and said at least one tubing line in at least one configuration of the system. The at least one tubing line typically includes a series of tubing lines. The at least one connector typically includes a plurality of connectors. The closed system may further include at least one container operably linked to the series of tubing lines, such that the at least one connection permits liquid and/or gas to pass between the at least one container and the at least one opening via the series of tubing lines.

The at least one connector may include one or more connectors selected from the group consisting of valves, luer ports, and spikes, e.g., a rotational valve, such as a stopcock or multirotational port, and/or an aseptic connector.

The at least one container may include one or more bags, vials, and/or syringes, and may include container(s) designated as a diluent container, a waste container, a product collection container, output container, and/or an input container.

In some embodiments, the at least one container includes at least one input container including the virus and/or cells (which may be a single input container comprising the virus and cells or two input containers comprising the virus and cells, respectively), a waste container, a product container, and at least one diluent or wash solution-containing container, each connected to said cavity via said series of tubing lines and the at least one opening.

In some of any such embodiments, at least one container further includes a container that contains a gas prior to and/or during at least a point during said incubation and/or the closed system further includes a microbial filter capable of taking in gas to the internal cavity of the centrifugal chamber and/or the closed system contains a syringe port for effecting intake of gas.

The methods in some embodiments further include, prior to and/or during the incubation, effecting intake of the input composition into said cavity. The intake may include flow of liquid from the at least one input container into the cavity through said at least one opening. The intake may include intake of virus from one input container and input of cells from another, to produce the input composition for incubation.

In some embodiments, the method includes, prior to and/or during said incubation, providing or effecting intake of gas into said cavity under sterile conditions, said intake being effected by (a) flow of gas from the container that includes gas, (b) flow of gas from an environment external to the closed system, via the microbial filter, or (c) flow of gas from a syringe connected to the system at the syringe port.

In some embodiments, the effecting intake of the gas into the internal cavity of the centrifugal chamber is carried out simultaneously or together with the effecting intake of the input composition to the internal cavity of the centrifugal chamber.

In some of any such embodiments, the input composition and gas are combined in a single container under sterile conditions outside of the chamber prior to said intake of said input composition and gas into the internal cavity of the centrifugal chamber.

In some embodiments, the effecting of the intake of the gas is carried out separately, either simultaneously or sequentially, from the effecting of the intake of the input composition into said cavity.

In some of any such embodiments, the intake of gas is effected by permitting or causing flow of the gas from a sterile closed container containing the gas, an external environment through a microbial filter, or a syringe containing said gas.

In some of any such embodiments, the gas is air.

In some embodiments of the provided process methods, the incubation is part of a continuous process, where the method further includes, during at least a portion of the incubation, effecting continuous intake of said input composition into the cavity, typically during rotation of the chamber, and during a portion of the incubation, effecting continuous expression (i.e. outtake) of liquid from said cavity through said at least one opening, typically during rotation of the chamber. The continuous intake and outtake in some embodiments occur simultaneously.

In some embodiments, the method includes during a portion of said incubation, effecting continuous intake of gas into said cavity during rotation of the chamber; and/or during a portion of said incubation, effecting continuous expression of gas from said cavity.

In some embodiments, the method includes the expression of liquid and the expression of gas from said cavity, where each is expressed, simultaneously or sequentially, into a different container.

In some of any such embodiments, at least a portion of the continuous intake and the continuous expression occur simultaneously.

In some embodiments, the incubation is part of a semi-continuous process, such as one in which the method further includes effecting intake of the input composition into the cavity through the at least one opening, conducting all or part of the incubation, such as the centrifugation, and then effecting expression of liquid from the cavity, and then repeating the process, whereby another input composition is taken in to the cavity, followed by centrifugation, followed by expression. The process can be iterative and include several more rounds of intake, processing, and expression.

In some of any such embodiments, the incubation is part of a semi-continuous process, the method further including prior to said incubation, effecting intake of said input composition, and optionally gas, into said cavity through said at least one opening; subsequent to said incubation, effecting expression of liquid and/or optionally gas from said cavity; effecting intake of another input composition including cells and said viral particles containing a recombinant viral vector, and optionally gas, into said internal cavity; and incubating said another input composition in said internal cavity, wherein the method generates another output composition containing a plurality of cells of the another input composition that are transduced with said viral vector.

In some of any such embodiments, said providing or said intake of the input composition into the cavity includes intake of a single composition including the cells and the viral particles containing the recombinant viral vector; or intake of a composition including the cells and a separate composition containing the viral particles containing the recombinant viral vector, whereby the compositions are mixed, effecting intake of the input composition.

The intake may include intake of a single composition containing the cells and the virus; or intake of a composition containing the cells and a separate composition containing the virus, whereby the compositions are mixed, effecting intake of the input composition. In some embodiments of the continuous or semi-continuous process, at least $1 \times 10^8$ cells or at least $1 \times 10^9$ cells or at least $1 \times 10^{10}$ cells or more are processed in total, over the multiple rounds or continuous process.

In some embodiments, the method includes effecting rotation of the centrifugal chamber prior to and/or during said incubation and effecting expression of liquid from the cavity into said waste container following the incubation; effecting expression of liquid from the at least one diluent container into said cavity via the at least one opening and effecting mixing of the contents of the cavity; and effecting expression of liquid from said cavity into the product container, thereby transferring cells transduced with the viral vector into the product bag.

In some embodiments, the method further includes carrying out other processing steps, or at least a portion of one or more other processing steps, within the same chamber and/or closed system. In some embodiments, the one or more processing steps can includes processes in which the cells are isolated, such as separated or selected, stimulated, and formulated within the same chamber and/or closed system. In some cases, the one or more further processing steps also can include washing cells, suspending cells and/or diluting or concentrating cells, which can be carried out prior to or subsequent to any one or more of the processing steps for isolating, such as separating or selecting, stimulating, transducing and/or formulating the cells. In some embodiments, the one or more other processing steps can be carried out prior to, simultaneously with or subsequent to the incubation of cells with the viral vector particles in the methods of transduction. In some embodiments, the one or more further processing steps, or a portion of the one or more further processing steps, can be carried out in a cavity of a centrifugal chamber that is the same or different as a cavity of a centrifugal chamber employed in the incubation of cells with the viral vector particles.

Among the provided processing methods, including isolation, e.g. selection, methods, stimulation methods, formulation methods and other processing methods, are those carried out according to any of the embodiments as described above.

For example, in some embodiments, the method further includes (a) washing a biological sample (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) containing cells in a cavity of a chamber, prior to the incubation for isolating, e.g. selecting cells, and/or prior to the incubation for incubating cells with viral vector particles, (b) isolating, e.g. selecting, the cells from a sample (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) in a cavity prior to the incubation of such cells with viral vector particles and/or (c) stimulating cells in a cavity prior to and/or during the incubation of such cells with viral vector particles, e.g., by exposing cells to stimulating conditions, thereby inducing cells of the input composition to proliferate. In some embodiments, the isolating includes immunoaffinity-based selection.

In some of any such embodiments, the method includes (a) washing a biological sample containing said cells in an internal cavity of a centrifugal chamber prior to said incubation; and/or (b) isolating said cells from a biological sample, wherein at least a portion of the isolation step is performed in an internal cavity of a centrifugal chamber prior to said incubation; and/or (c) stimulating cells prior to and/or during said incubation, said stimulating including exposing said cells to stimulating conditions, thereby inducing cells of the input composition to proliferate, wherein at least a portion of the step of stimulating cells is performed in an internal cavity of a centrifugal chamber.

In some embodiments, the methods may further include isolation, e.g., selection, of the cells in the chamber, e.g., by immunoaffinity based selection. In some embodiments, the isolation, e.g. selection, of cells is carried out prior to the incubation of cells with the viral vector particles in the methods of transduction, whereby the isolated, such as selected, cells are the cells present in the input composition and/or incubated with the viral vector particles. In some embodiments, the isolation, e.g., selection, includes incubation of cells with a selection reagent, such as an immunoaffinity reagent. In some embodiments, at least a portion of the isolation, e.g. selection, step, such as incubation of cells with a selection reagent, e.g. an immunoaffinity reagent, is carried out in the cavity of a chamber, which, in some cases, can include rotation of the chamber, for example, for mixing of the reagent and cells.

In some embodiments, the methods may further include stimulating cells prior to, during and/or subsequent to the incubation of cells with the viral vector particles, in which at least all or a portion of the stimulation can be carried out in a cavity of a centrifugal chamber. In some embodiments, the stimulating conditions may include incubation of cells in the presence of an agent capable of activating one or more intracellular signaling domains of one or more components of a TCR complex, such as a primary agent that specifically binds to a member of a TCR complex, e.g., CD3, and a secondary agent that specifically binds to a T cell costimulatory molecule, e.g., CD28, CD137 (4-1-BB), OX40, or ICOS, including antibodies such as those present on the surface of a solid support, such as a bead. In some embodiments, at least a portion of the stimulation, such as incubation of cells in the presence of a stimulating condition, is carried out in the cavity of a chamber, which, in some cases, can include rotation of the chamber, for example, for mixing of the reagent and cells.

In some of any such embodiments, the method includes formulating cells, such as cells produced or generated in accord with the provided methods, including cell transduced by the method, in a pharmaceutically acceptable buffer in an internal cavity of a centrifugal chamber, thereby producing a formulated composition. In some embodiments, the methods further include effecting expression of the formulated composition to one or a plurality of containers. In some embodiments, the methods include the effecting of expression of the formulated composition includes effecting expression of a number of the cells present in a single unit dose to one or each of said one or a plurality of containers.

In some of any such embodiments, each of said a cavity of a centrifugal chamber is the same or different as a cavity of a centrifugal employed in one or more of the other steps and/or in the process of incubating and/or rotating an input composition containing cells and viral particles.

In some of any such embodiments, each of said centrifugal chambers is integral to a closed system, said closed system including said chamber and at least one tubing line operably linked to the at least one opening via at least one connector, whereby liquid and gas are permitted to move between said cavity and said at least one tubing line in at least one configuration of said system.

The cells processed by the methods typically are primary cells, such as cells obtained from a subject, typically a human. The cells may be derived from a subject to which the therapy is to be administered, such as one having a disease or condition targeted by a recombinant molecule expressed by a vector transduced, e.g., a recombinant antigen receptor such as a chimeric antigen receptor or transgenic TCR. Alternatively, the cells may be from a different subject. Thus, the methods encompass processing for autologous and allogeneic transfer. The cells may include suspension cells, e.g., white blood cells, e.g., T cells, such as isolated $CD8^+$ T cells, or isolated $CD4^+$ T cells or subsets thereof, or NK cells.

In some embodiments, during the incubation, the centrifugal chamber is associated with a sensor, for example, a sensor capable of monitoring the position of the movable member, and control circuitry, such as circuitry capable of receiving and transmitting information to and from the sensor, causing movement of said movable member, and/or that is further associated with a centrifuge and thus is capable of causing rotation of the chamber during said incubation.

In some embodiments, the chamber contains the movable member and during the incubation is located within a centrifuge and associated with a sensor capable of monitoring the position of the movable member, and control circuitry capable of receiving and transmitting information from the sensor and causing movement of the movable member, intake and expression of liquid to and from said cavity via said one or more tubing lines, and rotation of the chamber via the centrifuge.

In some embodiments, the chamber, control circuitry, centrifuge, and/or sensor are housed within a cabinet, e.g., during the incubation.

In some embodiments of any of the viral transfer, e.g., transduction methods, the recombinant viral vector encodes a recombinant receptor, which is thereby expressed by cells of the output composition. In some embodiments, the recombinant receptor is a recombinant antigen receptor, such as a functional non-T cell receptor, e.g., a chimeric antigen receptor (CAR), or a transgenic T cell receptor (TCR). In some embodiments, the recombinant receptor is a chimeric receptor containing an extracellular portion that specifically binds to a ligand and an intracellular signaling portion containing an activating domain and a costimulatory domain.

In some of any such embodiments, the cells include primary human T cells obtained from a human subject and prior to the incubation with viral vector particles and/or prior to completion of the transduction and/or, where the method includes formulation, prior to the formulation, the primary human T cells have not been present externally to the subject at a temperature of greater than 30° C. for greater than 1 hour, greater than 6 hours, greater than 24 hours, or greater than 48 hours or prior to the incubation and/or prior to the completion of the transduction, and/or where the method includes formulation, prior to the formulation, the primary human T cells have not been incubated in the presence of an antibody specific for CD3 and/or an antibody specific for CD28 and/or a cytokine, for greater than 1 hour, greater than 6 hours, greater than 24 hours, or greater than 48 hours.

Provided herein are methods for isolation, e.g. selection, of cells including (a) incubating a selection reagent and primary cells in an internal cavity of a centrifugal chamber under mixing conditions, whereby a plurality of the primary cells bind to said selection reagent and (b) separating the plurality of the primary cells from another one or more of the primary cells based on binding to the selection reagent, thereby enriching the primary cells based on binding to the selection reagent, wherein the centrifugal chamber is rotatable around an axis of rotation and the internal cavity has a maximum volume of at least 50 mL, at least 100 mL, or at least 200 mL. In some embodiments, the methods for isolation, e.g. selection, occur in a closed system. In some embodiments, prior to the step of separating the plurality of cells, the cells incubated with the selection reagent, are expressed from or transferred out of the chamber, but maintained in the closed system. In some embodiments, optionally, subsequent to incubation with the selection reagent and prior to separating the cells, the method further includes one or more washing steps, which in some cases, can be performed in the cavity of the chamber in accord with the provided methods. In some embodiments, the step of separating the cells can be effecting using a solid support, such as using an immunoaffinity-column, including those for magnetic separation, which can be contained in the closed system.

Provided herein are methods for stimulation of cells, including incubating a stimulation agent and primary cells under conditions whereby the stimulation agent binds to a molecule expressed by a plurality of the primary cells and the plurality of the cells are activated or stimulated, wherein at least a portion of the incubation is carried out in an internal cavity of a centrifugal chamber under mixing conditions, where the centrifugal chamber is rotatable around an axis of rotation and the internal cavity has a maximum volume of at least 50 mL, at least 100 mL, or at least 200 mL.

In some embodiments, the methods of stimulation are performed as part of a process that includes transducing cells, whereby all or a part of such process is performed in a centrifugal chamber and/or as part of the same closed system. In some embodiments, the primary cells that are stimulated with a stimulation agent include or are cells obtained following isolation, e.g. selection, of cells from a biological sample, such as in accord with the provided methods. In some embodiments, at least a portion of the stimulation is carried out simultaneously or during the incubation of cells with the viral vector particles, such that the primary cells include or are cells present in the input composition and/or are cells in which transduction has occurred or is initiated. In some embodiments, at least a portion of the stimulation is carried out prior to the incubation of cells with the viral vector particles, such that the cells incubated with the viral vector particles are stimulated cells, which, in some cases, includes proliferating cells.

In some embodiments, at least a portion of the one of more other processing steps of the method, including isolation, e.g. selection, stimulation, washing and/or formulation, that is carried out in a chamber includes where the chamber includes an end wall, a substantially rigid side wall extending from said end wall, and at least one opening, wherein at least a portion of the side wall surrounds the internal cavity and the at least one opening is capable of permitting intake of liquid into the internal cavity and expression of liquid from the cavity.

Provided herein are compositions containing transduced cells produced by the methods of any of the above embodiments. In some of any such embodiments, the composition contains cells that are primary cells and/or human cells and/or include white blood cells, and/or T cells, and/or NK cells. In some of any such embodiments, the composition contains at least $5\times10^7$ cells, $1\times10^8$ cells, $2\times10^8$ cells, $4\times10^8$ cells, $6\times10^8$ cells, $8\times10^8$ cells or $1\times10^9$ cells. In some of any such embodiments, the composition contains a therapeutically effective number of cells for use in adoptive T cell therapy. In some of any such embodiments, the cells are T cells and subsequent to transduction, the cells in the composition are not subjected to cell expansion in the presence of a stimulating agent and/or the cells are not incubated at a temperature greater than 30° C. for more than 24 hours or the composition does not contain a cytokine or the composition does not contain a stimulating agent that specifically binds to CD3 or a TCR complex.

Provided herein are compositions containing at least $1\times10^7$ or at least $5\times10^7$ T cells, at least a plurality of which are transduced with a recombinant viral vector, where subsequent to transduction, the cells in the composition have not been subjected to cell expansion in the presence of a stimulating agent and/or the cells have not been incubated at a temperature greater than 30° C. for more than 24 hours and/or at least 30, 40, 50, 60, 70, or 80% of the T cells in the composition contain high surface expression of CD69 or TGF-beta-II. In some embodiments, the composition contains at least $1\times10^8$ cells, $2\times10^8$ cells, $4\times10^8$ cells, $6\times10^8$, $8\times10^8$ cells or $1\times10^9$ cells.

In some of any such embodiments, the T cells are unfractionated T cells, isolated CD8+ T cells, or isolated CD4+ T cells.

In some of any such embodiments, at least 2.5%, at least 5%, at least 6%, at least 8%, at least 10%, at least 20%, at least 25%, at least 30%, at least 40%, at least 50%, or at least 75% of said cells in said composition are transduced with the viral vector.

In some of any such embodiments, the viral vector encodes a recombinant receptor and transduced cells in the composition express the recombinant receptor. In some embodiments, the recombinant receptor is a recombinant antigen receptor. In some embodiments, the recombinant antigen receptor is a functional non-T cell receptor. In some embodiments, the functional non-T cell receptor is a chimeric antigen receptor (CAR). In some embodiments, the recombinant receptor is a chimeric receptor containing an extracellular portion that specifically binds to a ligand and an intracellular signaling portion containing an activating domain and a costimulatory domain. In some embodiments, the recombinant antigen receptor is a transgenic T cell receptor (TCR).

In some of any such embodiments, among all the cells in the composition, the average copy number of the recombinant viral vector is no more than about 10, no more than 8, no more than 6, no more than 4, or no more than about 2, or among the cells in the composition transduced with the recombinant viral vector, the average copy number of said vector is no more than about 10, no more than 8, no more than 6, no more than 4, or no more than about 2.

In some of any such embodiments, the composition contains a pharmaceutically acceptable excipient.

Provided herein are methods of treatment, including administering to a subject having a disease or condition the composition of any of the above embodiments. In some embodiments, the transduced T cells in the composition exhibit increased or longer expansion and/or persistence in the subject than transduced T cells in a composition in which, subsequent to transduction, the cells in the composition have been subjected to cell expansion in the presence of a stimulating agent and/or the cells have been incubated at a temperature greater than 30° C. for more than 24 hours.

In some of any such embodiments, the recombinant receptor, chimeric antigen receptor or transgenic TCR specifically binds to an antigen associated with the disease or condition. In some embodiments, the disease or condition is a cancer, an autoimmune disease or disorder, or an infectious disease.

Provided herein are compositions containing at least $1\times10^7$ cells and at least at or about 1 infectious unit (IU) per cell of viral particles containing a recombinant viral vector. In some embodiments, the cells contain at least or about $50\times10^6$ cells, $100\times10^6$ cells, or $200\times10^6$ cells, and/or said viral particles are present in the composition in an amount that is at least 1.6 IU/cell, 1.8 IU/cell, 2.0 IU/cell, 2.4 IU/cell, 2.8 IU/cell, 3.2 IU/cell, 3.6 IU/cell, 4.0 IU/cell, 5.0 IU/cell, 6.0 IU/cell, 7.0 IU/cell, 8.0 IU/cell, 9.0 IU/cell or 10.0 IU/cell.

In any of such embodiments, the liquid volume of the composition is less than or equal to 220 mL, less than or equal to 200 mL, less than or equal to 100 mL, less than or equal to 50 mL or less than or equal to 20 mL.

In some of any such embodiments, the cells are primary cells. In some of any such embodiments, the cells are human cells. In some of any such embodiments, the cells include suspension cells, the cells include white blood cells and/or the cells include T cells or NK cells. In some embodiments, the cells are T cells and the T cells are unfractionated T cells, isolated CD8+ T cells, or isolated CD4+ T cells.

In some of any such embodiments, the viral vector encodes a recombinant receptor. In some embodiments, the recombinant receptor is a recombinant antigen receptor. In some embodiments, the recombinant antigen receptor is a functional non-T cell receptor. In some embodiments, the functional non-T cell receptor is a chimeric antigen receptor (CAR). In some embodiments, the recombinant receptor is a chimeric receptor containing an extracellular portion that specifically binds to a ligand and an intracellular signaling portion containing an activating domain and a costimulatory domain. In some embodiments, the recombinant antigen receptor is a transgenic T cell receptor (TCR).

Provided herein are centrifugal chambers rotatable around an axis of rotation, including an internal cavity containing the composition of any of the above embodiments.

Provided herein are centrifugal chambers rotatable around an axis of rotation, containing an internal cavity containing (a) a composition containing at least $5\times10^7$ primary T cells transduced with a recombinant viral vector and/or (b) a composition containing at least $5\times10^7$ primary T cells and viral particles containing a recombinant viral vector.

In some of any such embodiments, the chamber further contains an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity.

In some of any such embodiments, said composition in said cavity contains at least $1\times10^8$ cells, $2\times10^8$ cells, $4\times10^8$ cells, $6\times10^8$ cells, $8\times10^8$ cells or $1\times10^9$ of the cells.

In some of any such embodiments, the T cells are unfractionated T cells, isolated CD8+ T cells, or isolated CD4+ T cells.

In some of any such embodiments of the chamber, at least 2.5%, at least 5%, at least 6%, at least 8%, at least 10%, at least 20%, at least 25%, at least 30%, at least 40%, at least 50%, or at least 75% of said cells in said composition are transduced with a viral vector.

In some of any such embodiments of the chamber, the viral vector encodes a recombinant receptor and cells in the composition express the recombinant receptor. In some embodiments, the recombinant receptor is a recombinant antigen receptor. In some embodiments, the recombinant antigen receptor is a functional non-T cell receptor. In some embodiments, the functional non-T cell receptor is a chimeric antigen receptor (CAR). In some embodiments, the recombinant receptor is a chimeric receptor containing an extracellular portion that specifically binds to a ligand and an intracellular signaling portion containing an activating domain and a costimulatory domain. In some embodiments, the recombinant antigen receptor is a transgenic T cell receptor (TCR).

In some of any such embodiments of the chamber, among all the cells in the composition, the average copy number of said recombinant viral vector is no more than about 10, no more than 8, no more than 6, no more than 4, or no more than about 2 or among the cells in the composition transduced with the recombinant viral vector, the average copy number of said vector is no more than about 10, no more than 8, no more than 6, no more than 4, or no more than about 2.

Provided herein are centrifugal chambers rotatable around an axis of rotation, including an internal cavity containing the composition of any of the above embodiments. In some embodiments, the chamber further contains a volume of gas up to the maximum volume of the internal cavity of the chamber. In some embodiments, the gas is air.

In some of any such embodiments of the chamber, the chamber is rotatable around an axis of rotation and includes an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity. In some embodiments the side wall is curvilinear. In some embodiments the side wall is generally cylindrical.

In some of any such embodiments of the chamber, said at least one opening includes an inlet and an outlet, respectively capable of permitting said intake and expression or said at least one opening includes a single inlet/outlet, capable of permitting said intake and said expression. In some of any such embodiments of the chamber, aid at least one opening is coaxial with the chamber and is located in the end wall.

In some of any such embodiments, the chamber further includes a movable member and said internal cavity is a cavity of variable volume defined by said end wall, said substantially rigid side wall, and said movable member, said movable member being capable of moving within the chamber to vary the internal volume of the cavity. In some embodiments, the movable member is a piston and/or the movable member is capable of axially moving within the chamber to vary the internal volume of the cavity.

In some of any such embodiments, the internal surface area of said cavity is at least at or about $1\times10^9$ µm², the internal surface area of said cavity is at least at or about $1\times10^{10}$ µm², the length of said rigid wall in the direction extending from said end wall is at least about 5 cm, the length of said rigid wall in the direction extending from said end wall is at least about 8 cm and/or the cavity contains a radius of at least about 2 cm at at least one cross-section.

In some of any such embodiments of the chamber, the liquid volume of said composition present in said cavity is between or between about 0.5 mL per square inch of the internal surface area of the cavity (mL/sq.in) and 5 mL/sq.in, 0.5 mL/sq.in. and 2.5 mL/sq.in., 0.5 mL/sq.in. and 1 mL/sq.in., 1 mL/sq.in. and 5 mL/sq.in., 1 mL/sq.in. and 2.5 mL/sq.in. or 2.5 mL/sq.in. and 5 mL/sq.in. In some of any such embodiments, the liquid volume of said composition present in said cavity is at least 0.5 mL/sq.in., 1 mL/sq.in., 2.5 mL/sq.in., or 5 mL/sq.in.

Provided herein are closed systems containing the centrifugal chamber of any of the above embodiments. In some of any such embodiments of the closed system, the centrifugal chamber is capable of rotation at a speed up to 8000 g, wherein the centrifugal chamber is capable of withstanding a force of 500, 1000, 1500, 2000, 2500, 3000 or 3200 g, without substantially yielding, bending, or breaking or otherwise resulting in damage of the chamber and/or while substantially holding a generally cylindrical shape under such force.

BRIEF DESCRIPTION OF THE DRAWINGS

FIG. 2 shows transduction efficiency calculated as percentage of CD3$^+$ T Cells with surface expression of a CAR encoded by a viral vector following incubation under the indicated conditions as described in Example 2.

DETAILED DESCRIPTION

Figure 1A:
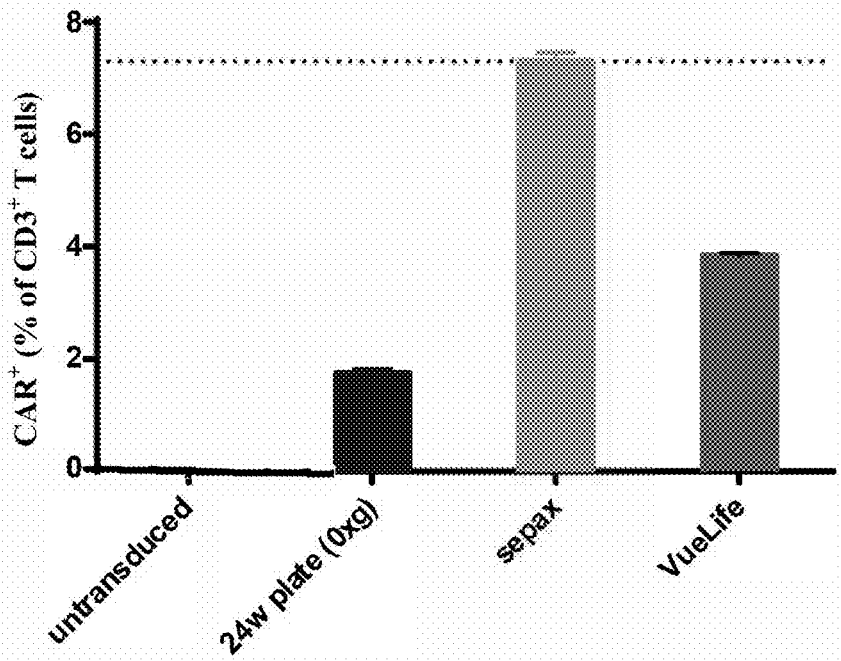
FIG. 1A shows transduction efficiency calculated as percentage of CD3$^+$ T cells with surface expression of a chimeric antigen receptor (CAR) encoded by a viral vector, following incubation under various conditions as described in Example 1.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods of Cell Processing and Associated Systems, Kits, and Devices

Provided are methods for processing cells, for example, to generate compositions of cells for use in adoptive cell therapy. The methods include those for transferring recombinant viral vectors to the cells, such as by viral transduction. The viral vectors generally encode recombinant molecules to be expressed in the cells, e.g., for use in cell therapy. Processing steps of the methods can also or alternatively include all or a portion of cell washing, dilution, selection, isolation, separation, cultivation, stimulation, packaging, and/or formulation. The methods generally allow for the processing, e.g., selection or separation and/or transduction, of cells on a large scale (such as in compositions of volumes greater than at or about 50 mL). One or more of the cell processing steps generally are carried out in the internal cavity of a centrifugal chamber, such as a substantially rigid chamber that is generally cylindrical in shape and rotatable around an axis of rotation, which can provide certain advantages compared to other available methods. In some embodiments, all processing steps are carried out in the same centrifugal chamber. In some embodiments, one or more processing steps are carried out in different centrifugal chambers, such as multiple centrifugal chambers of the same type.

The provided methods offer various advantages compared with available methods for cell processing, including for transduction and selection, particularly those for large-scale cell processing. Certain available methods have not been entirely satisfactory, for example, due to less than optimal efficacy, accuracy, reproducibility, cost and time expenditure, risk of error, complexity, and need for user handling and biosafety facilities. In some embodiments, the provided methods are suitable for large-scale and/or clinical-grade cell production, while still providing desirable features otherwise available only with small-scale production methods, and offering additional advantages not provided by available methods. For example, the methods for cell transduction and/or affinity-based selection offer advantages compared with available methods performed in flexible plastic bags or plastic multi-well plates.

In some embodiments, the centrifugal chamber and/or its internal cavity in which the cells are processed is surrounded or defined at least in part by rigid or substantially rigid material. Incubation in a cavity bound by such materials, such as hard plastic, permits centrifugation under certain conditions, such as forces higher than those that may be used with bags used in other large-scale cell processing methods. For example, in some embodiments, the chamber and cavity withstand centrifugation at a force, e.g., a relative centrifugal force, of least at or about 500 g, 1000 g, 1500 g, 2000 g, 2500 g, 3000 g or 3200 g, as measured for example at an internal or external wall of the chamber or cavity, or at one or more cell, such as layer of cells, without substantially yielding, bending, or breaking or otherwise resulting in damage of the chamber or cavity holding the cells, such that the chamber and/or cavity substantially hold their shape under such force.

Accordingly, the chamber and/or its internal cavity typically are surrounded by all or a portion of a rigid or semi-rigid side wall, such as one made of hard plastic, which holds its shape under the centrifugal force applied. The side wall generally is curvilinear, e.g., cylindrical or generally cylindrical, and typically extends from one or two end walls of the chamber, the internal side of one or both of which may also define the boundaries of the internal cavity. The end walls in some embodiments are also made of rigid materials, and in some embodiments may include more flexible materials. In some embodiments, while a wall is made of rigid material or substantially rigid material, it may nonetheless be lined and/or coated with flexible material and/or contain small portions which are more flexible, so long as the cavity as a whole maintains its overall shape during the conditions of the methods.

The centrifugal chamber generally is rotatable around an axis of rotation, and the cavity typically is coaxial with the chamber. In some embodiments, the centrifugal chamber further includes a movable member, such as a piston, which generally is capable of movement (e.g., axial movement) within the chamber, to vary the volume of the cavity. Thus, in particular embodiments, the internal cavity is bound by the side wall and end wall of the chamber and the movable member, and has a variable volume that may be adjusted by moving the movable member. The movable member may be made of rigid, substantially or generally rigid, flexible materials, or combinations thereof.

The chamber generally also includes one or more opening(s), such as one or more inlet, one or more outlet, and/or one or more inlet/outlet, which can permit intake and expression of liquid and/or gas to and from the cavity. In some cases, the opening can be an inlet/outlet where both intake and expression of the liquid and/or gas occurs. In some cases, the one or more inlets can be separate or different from the one or more outlets. The opening or openings may be in one of the end walls. In some embodiments, liquid and/or gas is taken into and/or expressed from the cavity by movement of the movable member to increase and/or decrease the cavity's volume. In other embodiments, liquid and/or gas may be taken into and/or expressed from the cavity through a tubing line or other channel that is or is placed in connection with the opening, for example, by placing the line or channel in connection with and control of a pump, syringe, or other machinery, which may be controlled in an automated fashion.

In some embodiments, the chamber is part of a closed system, such as a sterile system, having various additional components such as tubing lines and connectors and caps, within which processing steps occur. Thus, in some embodiments, the provided methods and/or steps thereof are carried out in a completely closed or semi-closed environment, such as a closed or semi-closed sterile system, facilitating the production of cells for therapeutic administration to subjects without the need for a separate sterile environment, such as a biosafety cabinet or room. The methods in some embodiments are carried out in an automated or partially automated fashion.

In some embodiments, the chamber is associated with a centrifuge, which is capable of effecting rotation of the chamber, such as around its axis of rotation. Rotation may occur before, during, and/or after the incubation in one or more of the processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal. One exemplary chamber is depicted within exemplary closed systems depicted in FIG. 5, FIG. 7 or FIG. 11.

The processing steps of the methods (e.g., the steps carried out in whole or in part in the chamber) may include any one or more of a number of cell processing steps, alone or in combination. In particular embodiments, the processing steps include transduction of the cells with viral vector particles containing a retroviral vector, such as one encoding a recombinant product for expression in the cells, where at least a part of the incubation with the viral vector particles is performed in the chamber to initiate transduction. The methods may further and/or alternatively include other processing steps, such as steps for the isolation, separation, selection, cultivation (e.g., stimulation of the cells, for example, to induce their proliferation and/or activation), washing, suspension, dilution, concentration, and/or formulation of the cells. In some embodiments, the method includes processing steps carried out in an order in which: cells, e.g. primary cells, are first isolated, such as selected or separated, from a biological sample; resulting isolated or selected cells are stimulated in the presence of a stimulation reagent; stimulated cells are incubated with viral vector particles for transduction; and transduced cells are formulated in a composition. In some embodiments, the stimulation is additionally or alternatively performed during at least a part of the incubation with the viral vector particles. In some cases, stimulation is additionally or alternatively carried out after incubation of cells with the viral vector particles. In some cases, the methods do not include a step of stimulating the cells. In some embodiments, the method can include one or more processing steps from among washing, suspending, diluting and/or concentrating cells, which can occur prior to, during or simultaneous with or subsequent to one or more of the isolation, such as separation or selection, stimulation, transduction and/or formulation steps. All or a portion of each of the processing steps may be performed in a closed system, such as in a centrifugal chamber. In aspects of the methods, the processes need not be performed in the same closed system, such as in the same centrifugal chamber, but can be performed under a different closed system, such as in a different centrifugal chamber; in some embodiments, such different centrifugal chambers are at the respective points in the methods placed in association with the same system, such as placed in association with the same centrifuge. In some embodiments, all processing steps are performed in a closed system, in which all or a portion of each one or more processing step is performed in the same or a different centrifugal chamber.

In some embodiments, the methods provide the ability to transduce the cells at a higher transduction efficiency compared with available methods, e.g., by carrying out all or a part of transduction at higher centrifugal forces/speeds, and/or by allowing easy, automated, and/or independent control or adjustment of various parameters, such as volume or amount of reagents, speed, and/or temperature. In some embodiments, the methods increase efficacy and/or reduce variability (increasing reproducibility), e.g., by streamlining and/or decreasing the number of user-interactions and/or handling steps, such as by providing automated or semi-automated control of the various steps.

In some embodiments, by virtue of carrying out one or more, e.g., all or a portion of all, of the processing steps within a closed system, such as a sterile closed system, the provided methods allow for the large-scale preparation of cells for clinical use without exposing the cells to non-sterile conditions and without the use of a separate sterile room or cabinet. In some embodiments, the cells are isolated, separated or selected, stimulated, transduced, washed, and formulated within the closed system, e.g., in an automated fashion. In some embodiments, the methods are advantageous in that they are streamlined, e.g., require fewer steps, less user handling or intervention, e.g., by being carried out in a single, closed system and/or in an automated fashion.

For example, in some embodiments, the methods provide improvement over methods for processing cells for use in clinical applications, which may require transduction in bags in a centrifuge or plate, by mixing viral vector particles and cells at appropriate ratios in a biosafety cabinet, followed by transportation of the plate or bag to the centrifuge for transduction or other processing step, and additional steps that may also require handling. In some embodiments, the provided methods are less manual and/or labor-intensive compared to such available methods, requiring a reduced degree or quantity of handling and user interaction.

In some embodiments, the methods allow for a greater degree of process control compared with available methods. For example, the methods in some embodiments allow for the independent control of various parameters, e.g., in an automated fashion. For example, the methods may allow independent control of volume, amount, and/or concentration of various components and reagents used in and processed with the methods or various conditions used in one or more of the processes or methods. They generally permit control of the duration of one or more various steps of the methods, and/or the control of the ratio of cells in a particular incubation or composition, liquid volume, and/or surface area of the vessel being used for the processing, such as the chamber or cavity. The ability to control such parameters independently, particularly in an automated fashion and independently of one another, can allow a user to easily optimize and carry out the methods for individual conditions.

Also provided are systems, devices, and apparatuses for use with such methods, kits containing the same, and methods of use of the compositions and cells produced by the methods. For example, provided are methods of treatment and therapeutic use of the cells and compositions produced by the methods, such as in adoptive cell therapy. Also provided are pharmaceutical compositions and formulations for use in such therapies.

II. Centrifugal Chambers and Associated Systems and Devices

In some embodiments, all or part of one or more of the processing steps, such as the incubation with virus to initiate or effect transduction and/or incubation with beads for immunoaffinity-based separation and/or one or more other processing steps as described, is carried out in a centrifugal chamber. In particular, such steps and incubations generally are carried out in an internal cavity of such a chamber, which can be a same or different centrifugal chamber for each of the one or more processes.

The centrifugal chamber is generally capable of being rotated, e.g., by a centrifuge that may be associated with the chamber during the incubation. In some embodiments, the centrifuge chamber is rotatable around an axis of rotation, such as a vertical or generally or substantially vertical axis of rotation. In some embodiments, the centrifuge chamber includes an end wall and a side wall, at least a portion of which surrounds or encircles the internal cavity of the chamber. The centrifuge chamber generally also includes another end wall, from which the side wall extends in the opposite direction.

The internal cavity generally is bound on its outside by the internal sides of all or a portion of the end wall, all or a portion of the side wall, and all or a portion of another end wall of the chamber or another surface or object, such as a movable member within the chamber, such as a piston. The cavity in some aspects is hollow. In other aspects, a solid or hollow object is contained within part of the internal space of the cavity, such as a tube or channel.

In some aspects, the cavity is of variable volume, meaning that the total volume available within the cavity that may be occupied, e.g., by liquid or gas, may be varied, for example, by movement of the moveable member, e.g., a piston. In some embodiments, such movement is possible during various steps of the methods, such as during the incubation to initiate or effect the transduction or selection or steps subsequent and/or prior thereto. The movement in some embodiments may be effected in an automated fashion, such as by a pre-specified program run by virtue of circuitry and machinery associated with the chamber, such as sensors and motors sensing and controlling position of the movable member and other aspects of the process and circuitry for communicating between the sensors and one or more components.

The side wall of the chamber, or the portion thereof that surrounds the internal cavity of the chamber (and thus the shape of the cavity), typically is curvilinear, such as cylindrical, substantially cylindrical, or generally cylindrical. The term cylindrical is generally understood to those in the art to refer to a particular type of curvilinear surface, formed by the points at a fixed distance from a given line segment, deemed the axis of a cylindrical shape. "Generally cylindrical" refers to a shape or surface having a configuration that is approximately cylindrical in shape or structure, such as one that appears cylindrical to the eye or is nearly cylindrical, but allows for some degree of variability. For example, the term encompasses shapes and surfaces of which not every point is at the same distance from the axis, and permits some degree of contouring and/or tapering, so long as the shape or surface appears cylindrical and/or has a primarily cylindrical shape. It also encompasses shapes in which the majority of the shape is cylindrical, such as where the majority of an outer wall of the centrifuge chamber is cylindrical or substantially cylindrical in shape but relatively minor portions of it adopt another configuration, for example, tapering or contouring at or approaching one or more ends of the wall. In some embodiments, the portion of the side wall of the chamber that surrounds the cavity is cylindrical, whereas other portions of the wall may not be cylindrical.

In some embodiments, all or portions of the chamber and/or cavity are rigid or substantially rigid. For example, all or part of the side wall may be rigid or substantially rigid, for example to allow the chamber and cavity to withstand force, e.g., as applied during centrifugation at high speeds, for example, at a force (relative centrifugal force (RCF)) at the internal surface of the side wall of the cavity and/or at a surface layer of the cells of greater than at or about 200 g, greater than at or about 300 g, or greater than at or about 500 g, such as greater than at or about 600 g, 800 g, 1100 g, 1000 g, 1500 g, 1600 g, 2000 g, 2200 g, 2500 g, 3000 g or 3200 g; or at least at or about 600 g, 800 g, 1000 g, 1100 g, 1500 g, 1600 g 2000 g, 2200 g, 2500 g, 3000 g, or 3200 g, such as at or about 2100 g or 2200 g. In some embodiments, the RCF at the internal surface of the side wall of the cavity and/or at a surface layer of the cells is greater than at or about or is at or about 1100 g, 1200 g, 1400 g, 1600 g, 1800 g, 2000 g, 2200 g or more. In contrast, available methods for processing cells on a large scale, e.g., greater than 50 or 100 mL volume, using flexible bags, may only permit centrifugation at a relative centrifugal force of no more than 200 g, 500 g, or 1000 g. Thus, the provided methods can produce greater efficacy compared to such methods.

The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

The object, particle, or location (or average thereof) at which RCF is expressed or determined in a given case may be specified. For example, an RCF value or approximate value or range in some context herein is given for a particular portion or location within the centrifugal chamber used in such methods, such as at the internal surface of the side wall of the chamber's cavity in which the cells are processed, such as at any point along the surface of the cylindrical side wall of the cavity or at the average radial distance thereof. Similarly, the RCF value may be given for a radial distance or average radial distance within another container, such as a bag, in which cells are processed, relative to the axis of rotation. In other embodiments, the RCF is given for the location of the sample or composition as a whole or at one or more particular cells or average or layer thereof, during the rotation. For example, the value may be the RCF at a surface layer of the cells in the chamber or other container during rotation, such as at the cell surface at the interface between a liquid in which the cells are being spun and the cells themselves.

In general, the RCF is calculated by the formula $1.119 \times 10^{-5} (rpm)^2 r$ (or $1.12 \times 10\text{-}5 \times (rpm)2*r$), where r=the radius (i.e., the distance in cm of a given particle, object or substance from the axis of rotation), rpm=revolutions per minute. For example, in some embodiments, the RCF at the internal surface of the side wall of internal processing cavity in which cells are processed may be calculated using this formula, in which r is the distance between a point on the internal surface of the side wall and the axis of rotation. Alternatively, the RCF at a cell or surface layer of cells (such as the interface between the cell layer(s) and liquid during rotation) may be calculated using the formula, in which r is the distance between the cell, surface layer, and/or interface, or an average thereof. For example, in some embodiments, the radius (r) value for an RCF of the side wall may be based upon the mean of the maximum and minimum possible radii or all possible radii along the length of the side wall of the chamber. In some embodiments, the radius for an exemplary centrifugal chamber sold by Biosafe AG for use with the Sepax® system (e.g., A-200/F) is at or about 2.6 cm or at or about 2.7 cm. In such an exemplary chamber, the radius for determining RCF at the interface between the cell layer(s) and the liquid during rotation in such a chamber may be calculated by adding the exact or approximate radial distance between the internal side wall of the cavity and the chamber occupied by cells of the layer(s) during rotation. Such value may be calculated or approximated using known methods, for example, based on the diameter of one of the cells being processed and/or the average diameter among such cells, for example, during rotation of the chamber. Such value may be based on the full size of the cell but typically will take into account impact on the relative volume occupied by each cell of the rotation or force itself, which generally speaking will reduce such volume. In some examples, the approximated value is determined using the size of a nucleus of the cell (or average thereof).

Thus, RCF or average RCF during a particular spin in a particular chamber or device may be calculated for a given point or area based on the revolutions per minute (rpm) and the distance between that point and the axis of rotation using well-known methods. Revolutions per minute (rpm) may be determined for various devices and chambers using known methods, for example, using a tachometer appropriate for the particular device, system, or chamber. For example, in some embodiments a hand-held photo or laser tachometer may be used, e.g., in combination with reflective tape, in the case of a centrifuge, system, or device with a window from the environment to the chamber or cavity, such as the Sepax®, which is clear or otherwise permits the passage of light between the tachometer to the chamber. For opaque systems, other tachometers may be used such as vibrating reed type tachometers.

As is understood by those in the art, when used in the context of various vessels and containers, such as chambers, plates, tubes and bags, used in cell processing and centrifugation and materials thereof, rigid generally describes an object, portion thereof, or material which substantially holds its shape and/or volume when placed in an environment, such as under a degree of force, temperature, or other condition, in which one would ordinarily expect to be present in the course of using the object. For example, it is understood in the art that rigid centrifugal chambers and tubes such as those made of hard plastic are distinguishable from flexible vessels such as cell processing and cell culture bags, such as bags made of soft plastics and rubbers, e.g., fluoro ethylene propylene and similar materials, the shape of which changes when pressure is applied manually or by pulling in liquid or gas, causing the bag to expand. Thus, in some embodiments, rigid materials include hard plastic, metal, carbon fiber, composites, ceramics, and glass, and/or are distinguished from flexible materials such as soft rubber, silicone, and plastics used in making flexible bags, the shape and volume of which is easily changed by ordinary pressure, e.g., manual pressure or the filling of a vessel with liquid under ambient temperature or ordinary conditions.

For example, in some embodiments, the rigid centrifugal chamber and/or portion(s) or material(s) thereof, such as the rigid side wall or portion thereof that surrounds the central cavity, is able to hold its shape and/or volume and/or does not rupture or break in a way that it would no longer contain liquid or gas, under particular conditions. In some embodiments, such conditions include manual pressure, such as pressure capable of being applied by human hand. In some embodiments, such conditions include specified centrifugal forces, such as at a force (RCF), e.g., effective force, at the internal surface of the side wall of the cavity, of greater than at or about 200 g, greater than at or about 300 g, or greater than at or about 500 g, such as greater than at or about 1000 g, 1500 g, 2000 g, 2500 g, 3000 g or 3200 g; or at least at or about 1000 g, 1500 g, 2000 g, or 2500 g, 3000 g, or 3200 g, such as at or about 2100 or 2200 g. In some embodiments, the environment includes particular conditions, such as temperatures down to at or about $-80°$ C. and/or up to physiological temperatures or temperatures at which cells remain viable, and/or higher, such as temperatures of $18°$ C. to $42°$ C., such as $22°$ C. to $39°$ C., for example at least $25°$ C.$\pm 2°$ C. or $37°$ C.$\pm 2°$ C.

As is understood in the art, describing an object as rigid or substantially rigid does not exclude the possibility that any change in shape or volume of an object or material would ever occur, such as under excessive or unexpected force. For example, under excessive force or extreme environmental conditions, such as those well outside those ordinarily used in connection with the transduction methods described herein.

The chamber generally includes at least one opening, such as an inlet, an outlet, and/or an inlet/outlet, to permit substances to pass between the cavity or other portion of the chamber and other spaces. For example, such opening(s) generally are included in at least one of the walls of the chamber. The chamber generally includes at least one inlet and at least one outlet, which in some embodiments may be the same opening (inlet/outlet), through which liquid and/or gas may be taken into and expressed from the cavity. The opening is generally associated with another environment via a channel, e.g., tubing line or system of tubing lines, in some embodiments, such as via one or more connectors.

In some embodiments, the chamber is included as part of and/or integral to a system, such as a closed or partially closed system, which further includes additional components, such as tubing lines, connectors, and containers. In some embodiments, the chamber is pre-connected to one or more of the additional components, directly and/or indirectly. Such a chamber may be provided as part of a pre-assembled kit, e.g., a kit packaged for single, sterile, use in connection with the provided methods. In some embodiments, various components are packaged separately, for example, to allow for custom configurations in which a user connects and arranges the components for a particular embodiment of the processing methods.

The components typically include at least one tubing line, and generally a set or system of tubing lines, and at least one connector. Exemplary connectors include valves, ports, spikes, welds, seals, and hose clamps. The connectors and/or other components may be aseptic, for example, to permit the entire process to be carried out in a closed, sterile system, which can eliminate or reduce the need for clean rooms, sterile cabinets, and/or laminar flow systems.

In some embodiments, the at least one tubing line includes a series of tubing lines. Tubing can be made of a plastic, such as polycarbonate, and may be of various sizes and/or volumes, generally designed to permit flow of the desired liquid/gas at the appropriate rate, and connection with the chamber and/or other components. The series of tubing lines generally allows for the flow of liquids and gases between the chamber and/or one or more components of the system, such as the other containers, facilitated in some aspects by connectors. In some embodiments, the system includes tubing lines connecting each of the various components to at least one other of the components, where liquid is permitted to flow between each of the containers, such as bags, and the chamber, which may be permitted or stopped by the configuration of various connectors, such as valves, and/or clamps.

In some aspects, the connectors are such that they may be placed in or directed to alternative configurations, respectively blocking, allowing, and/or directing the flow of fluids and gases through various components, such as between various containers and through certain tubing lines connecting various components, such as rotational and gate valves. In other embodiments, certain connectors and/or other components have a single configuration which permits, directs, or blocks passage of liquid or gas, such as seals, caps, and/or open ports or channels. Various components in the system may include valves, ports, seals, and clamps. Valves can include rotational valves, such as stopcocks, rotary valves, and gate valves. Valves can be arranged in a manifold array or as a single multiport rotational valve. Ports may include Luer ports or spike ports. Seals may include O-rings, gaskets, adhesive seals, and couplings. Clamps may include pinch clamps.

Other components of a system include containers capable of holding or storing liquids and/or gases. The containers can include bags, vials, boxes, syringes, bulbs, tanks, bottles, beakers, buckets, flasks, and tubing lines. Such components can hold compositions used in and produced by the methods, including byproducts and interim products and waste. Such compositions may include liquid, including buffers, growth media, transduction media, water, diluents, washes, and/or saline, and may also include the cells, virus, and/or other agents for use in the processing steps, such as transduction. The containers also may include waste containers, and containers holding one or more output product, such as a product containing cells selected and/or transduced by one or more processing steps of the methods herein.

In some embodiments of the systems, a plurality of containers can be sterilely connected at one or more positions on the tubing line of the system. The containers can be connected simultaneously and/or sequentially during methods of cell processing in the provided embodiments. In some embodiments, the containers are detachable or removable from the connectors, such that the containers can be removed from the system and/or replaced by another container at the same position for use with the system. In some embodiments, not all connector positions of a system are connected to a container, such that the system can contain empty connectors. In some such embodiments, a closed system is maintained by operation of one or more stopcocks, valves or clamps, either manually or automatically, to close communication between a tubing line and an empty connector, e.g. port. In some embodiments, a closed system is maintained by sealing or detaching an empty connector, e.g. port.

Figure 5:
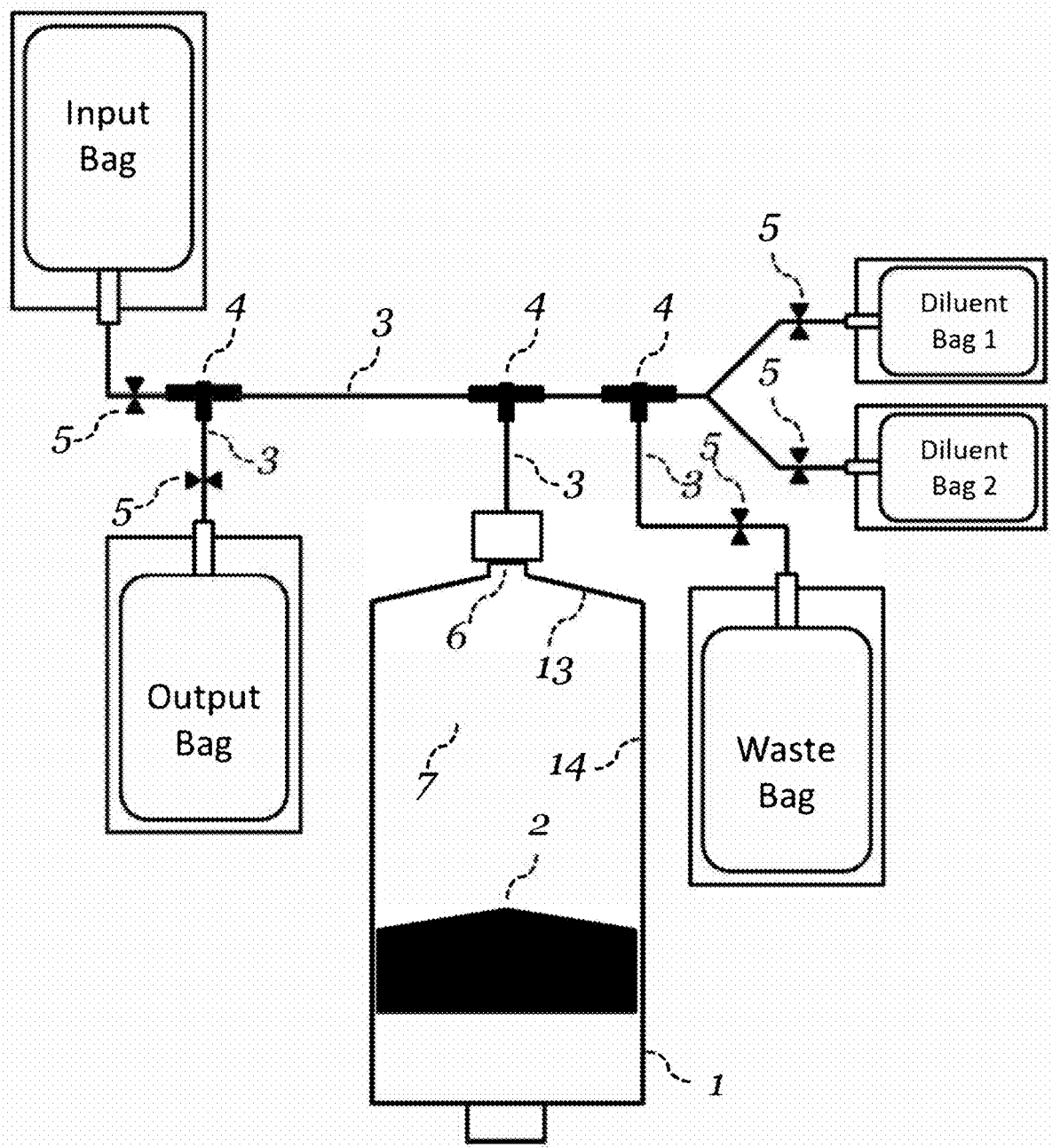
FIG. 5 provides a schematic representation of an embodiment of a closed system (processing kit) for use in embodiments of the provided methods. The depicted exemplary system includes a generally cylindrical centrifugal chamber (1), rotatable around an axis of rotation and including an end wall (13), a rigid side wall (14), and a piston (2), defining an internal cavity (7) of the chamber. The chamber further includes an inlet/outlet opening (6) to permit flow of liquid and gas in and out of the cavity in at least some configurations of the system. The opening (6) is operably linked with a series of tubing lines (3) and connectors, including stopcock valves (4) and various additional containers. Clamps (5) are also depicted.
Figure 7:
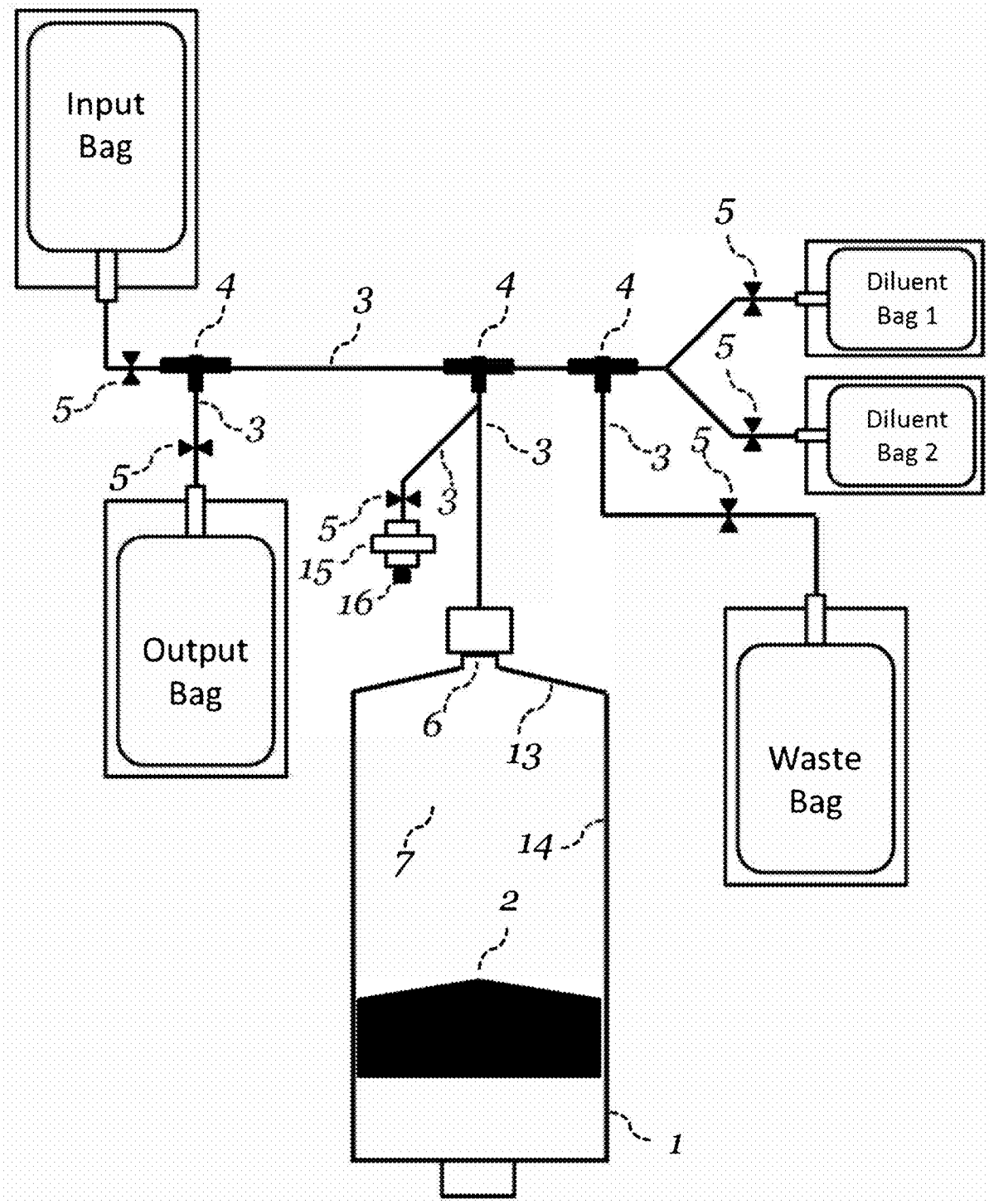
FIG. 7 provides a schematic representation of an embodiment of a closed system (processing kit) for use in embodiments of the provided methods. The depicted exemplary system includes a generally cylindrical centrifugal chamber (1), rotatable around an axis of rotation and including an end wall (13), a rigid side wall (14), and a piston (2), defining an internal cavity (7) of the chamber. The chamber further includes an inlet/outlet opening (6) to permit flow of liquid and gas in and out of the cavity in at least some configurations of the system. The opening (6) is operably linked with a series of tubing lines (3) and connectors, including stopcock valves (4), various additional containers, and an air filter (15) coupled to a removable cap (16). Clamps (5) are also depicted.
Figure 11:
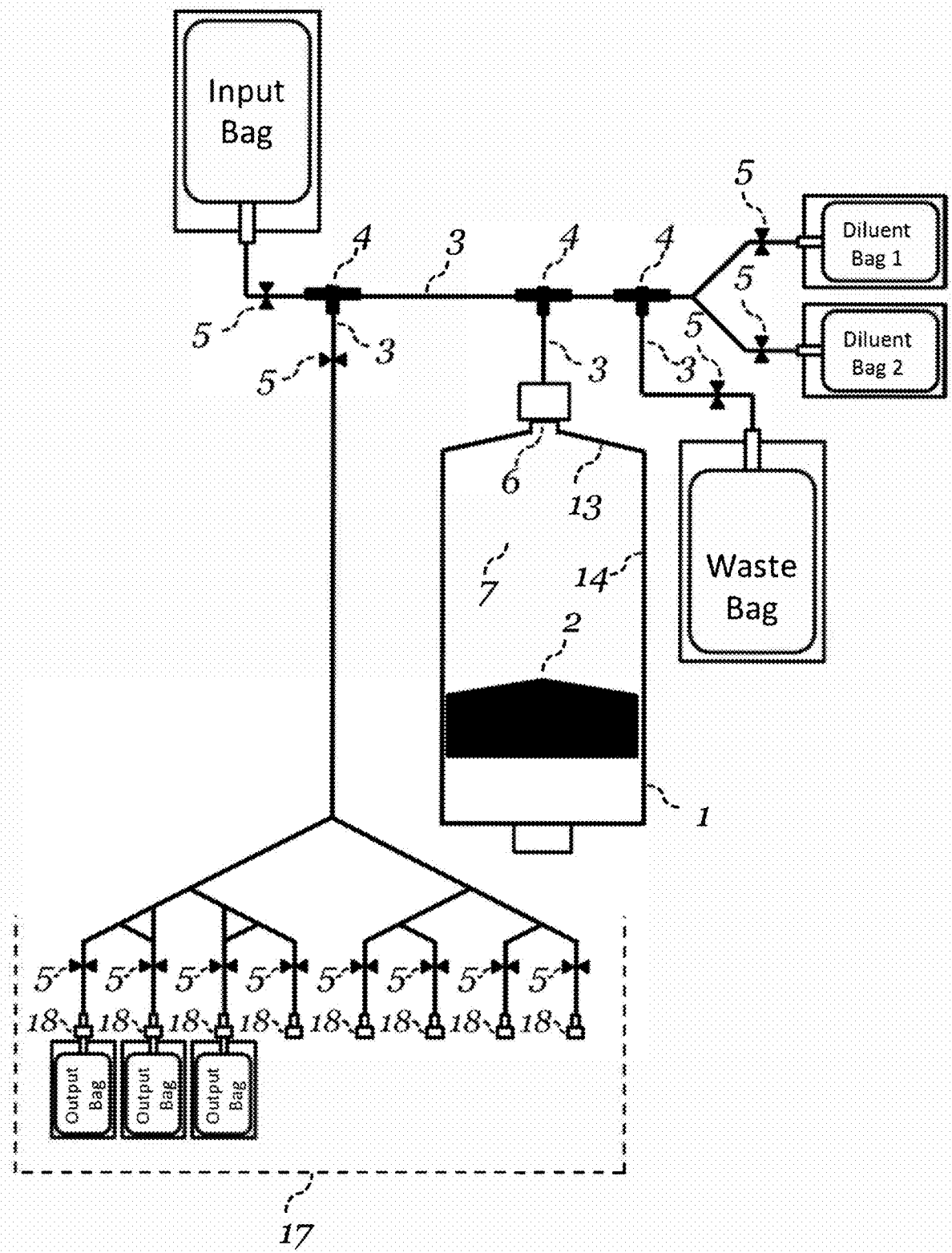
FIG. 11 provides a schematic representation of an embodiment of a closed system (processing kit) for use in embodiments of the provided methods. The depicted exemplary system includes a generally cylindrical centrifugal chamber (1), rotatable around an axis of rotation and including an end wall (13), a rigid side wall (14), and a piston (2), defining an internal cavity (7) of the chamber. The chamber further includes an inlet/outlet opening (6) to permit flow of liquid and gas in and out of the cavity in at least some configurations of the system. The opening (6) is operably linked with a series of tubing lines (3) and connectors, including stopcock valves (4) and ports (18), and various additional containers, including a plurality of output bags (17). Clamps (5) are also depicted.

In some embodiments of the systems, such as the exemplary systems depicted in FIG. 5, FIG. 7 or FIG. 11, containers can be operably connected to tubing lines, such as through a connector, at positions corresponding to an Input Bag position, Diluent Bag 1 position, a Diluent Bag 2 position, a Waste Bag position, and/or an Output Bag position. With reference to the Figures, the designation of these positions is for exemplification only, and is not meant to limit the particular type of container or content of the container that can be connected at a position. Also, in embodiments of the provided methods, not all positions of the system, such as depicted in the Figures, need to be utilized in performing the processing steps of the provided methods. In some such embodiments, a tubing line servicing an empty connector, e.g. port, can be disengaged or closed by operation of a stopcock or valve. In some embodiments, an empty connector can be sealed or detached.

In some embodiments, the system, such as a closed system, is sterile. In some embodiments, all connections of components of the system, such as between tubing line and a container via a connector, are made under sterile conditions. In some embodiments, connections are made under laminar flow. In some embodiments, connections are made using a sterile connection device that produces sterile connections, such as sterile welds, between a tubing and a container. In some embodiments, a sterile connection device effects connection under thermal condition high enough to maintain sterility, such as temperatures of at least 200° C., such as at least 260° C. or 300° C.

In some embodiments, the system may be disposable, such as a single-use kit. In some embodiments, a single-use kit can be utilized in a plurality of cycles of a process or processes, such as at least 2, 3, 4, 5 or more times, for example, in processes that occur in a continuous or a semi-continuous manner. In some embodiments, the system, such as a single-use kit, is employed for processing of cells from a single patient.

Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Depending on the particular process (e.g. dilution, wash, transduction, formulation), it is within the level of a skilled artisan to choose a particular kit that is appropriate for the process. Exemplary kits for use with such systems include, but are not limited to, single-use kits sold by BioSafe SA under product names CS-430.1, CS-490.1, CS-600.1 or CS-900.2.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

Exemplary systems for use in embodiments of the provided methods for carrying out one or more or all part of the process are depicted in FIG. 5, FIG. 7 and FIG. 11. In one exemplary embodiment as shown in FIG. 5, the centrifugal chamber (1) is at least generally cylindrical and is rotatable around an axis of rotation. The chamber includes an end wall (13) and a rigid side wall (14), and the movable member, which is a piston (2). The internal surfaces of the end wall (13), rigid side wall (14), and piston (2) collectively define the boundaries of the internal cavity (7) of the chamber. The cavity (7) is of variable volume and is coaxial with the chamber, and is designed to contain the liquid and/or gas that is included within the chamber during the processing steps. The piston (2) is axially movable within the chamber (1) to vary the volume of the internal cavity (7). The chamber further includes an inlet/outlet opening (6) to permit flow of liquid and gas in and out of the cavity in at least some configurations of the system. The opening (6) is operably linked with a series of tubing lines (3) and connectors, including stopcock valves (4), which are capable of controlling movement of fluid and/or gas between the various components of the system. The series of tubing lines (3) further are linked with various additional containers, which in the depicted configuration include bags labeled as Input Bag, Diluent Bags 1 and 2, a Waste Bag, and an Output Bag. Clamps (5) may be opened and closed to permit and block movement of fluid through the indicated portions of the series of tubing lines (3), permitting flow between various components of the system. In some embodiments, each container is operably connected to a tubing line via a port, such as a luer port or spike port. As an example, with reference to FIG. 5, at each point that a container is shown, in some aspects, the container is connected indirectly via a port.

While FIG. 5 shows connection of a container at each position or line, in an alternative embodiment, in some aspects, a container is not connected at each position or line of the system. In some embodiments of provided systems, a port is available at each position or line for connection, and a container is connected to all positions or lines or less than all positions or lines. In some embodiments, not all connector positions of a system are connected to a container, such that the system can contain empty connectors at each position or line.

In some embodiments, the system, such as the system shown in FIG. 5, can include a sterile or microbial filter. Exemplary of such a system is shown in FIG. 7, which depicts a filter (15). In some embodiments, the filter includes a filtration membrane having a pore size that blocks passage of microbial organisms, such as bacteria or viruses. In some embodiments, the pore size is between 0.1 µm to 0.45 µm, such as between 0.1 µm to 0.22 µm, such as about or 0.20 µm. In some embodiments, the membrane is composed of nitrocellulose (cellulose nitrate), cellulose acetate, regenerated cellulose, polyamide, polytetrafluorethylene (PTFE) or polyethersulfone (PES). In some embodiments, the filter includes a cap (16) to close or seal the membrane of the filter from exposure to the environment outside of the closed system. In some embodiments, the cap is closed or non-vented. In some embodiments, the cap is detachable. In some embodiments, the cap is fitted to the filter by a luer lock fitting. As described in more detail below, in some embodiments, the filter can be used to effect passage of gas, such as air, to and from the chamber of the system. In some such embodiments, the passage of air is maintained under sterile or microbial-free conditions.

In one embodiment, the Input Bag includes cells for processing by the provided methods, such as transduction. In one embodiment, Diluent Bag 1 includes viral vector particles containing the vector with which to transduce the cells. Thus, in some embodiments, the input composition containing the viral vector particles and cells is generated by effecting intake of fluid from the Input Bag and effecting intake of fluid from Diluent Bag 1. In some embodiments, Diluent Bag 2 contains wash solution. The Output Bag generally is designed to take in the cells following one or more of the processing steps, such as by transfer of the output composition from the cavity of the chamber to the Output Bag after incubation with viral vector particles. Thus, in some embodiments, the Output Bag contains transferred cells transduced with and/or in which transduction is initiated with the viral vector particles. In some embodiments, the processing comprises transduction of the cells with a viral vector.

In some embodiments, a multi-way manifold (17) can be used to operably connect one or a plurality of containers to the system via a plurality of ports (18) connected to a manifold of tubing lines. The multi-way manifold can contain a series of tubing lines that feed to the inlet/outlet of the chamber to permit flow between the chamber and the connected container or containers. In some such embodiments, the manifold connects a plurality of containers, such as at least 2, 3, 4, 5, 6, 7, 8 or more containers, at the same position or line on the system. In some embodiments, all ports of the multi-way manifold (17) are connected to a container, such as a bag. In some embodiments, less than all of the ports of the multi-way manifold (17) are connected to a container, such as a bag, such that a container is connected at less than the total number of port positions, for example less than 8, 7, 6, 5, 4, 3, or 2 containers, such as bags, are connected. In some embodiments, the tubing lines associated with the manifold can contain a clamp or stopcock, which can be opened or closed to control movement through the line into the container as necessary. The multi-way manifold (17) can be connected to any of the positions or lines available on the system, such to a position or line designated an input line, diluent line, wash line, waste line and/or output line.

In some embodiments, exemplary of a multi-way manifold (17) for linking a container or containers is shown in FIG. 11 for connecting one or a plurality of containers, such as one or a plurality of bags, for example one or a plurality of output Bags. As shown, in some embodiments, a multi-way manifold (17) can be connected to an output position or line, which includes a series of manifold tubing lines that each end with a connector, such as a port (18), for operable connection to a container, such as a bag. One or more of the ports, such as all of the ports or less than all of the ports, can be connected to a container. In one embodiment as exemplified in FIG. 11, up to 3 containers can be connected to each tubing line of the manifold via a port. In other embodiments, up to 1, 2, 3, 4, 5, 6, 7, or 8 containers, such as Output bags, can be connected at the output line. In some embodiments, one or a plurality of clamps (5) associated with tubing lines, such as the manifold tubing line, may be opened or closed to permit or control the movement of liquid into one or more of the plurality of Output Bags. In some embodiments, a single clamp can control movement of liquid into all Output Bags simultaneously. In some embodiments, the movement of liquid into each of the plurality of bags is separately regulated by a clamp operably connected to a tubing line associated with only one respective container, such that the movement of liquid into the respective container can be made separable from the movement of liquid into all other containers. In some embodiments, movement of liquid into each container, such as each bag, for example each Output bag, can be made to be sequential.

In some embodiments, the system is included with and/or placed into association with other instrumentation, including instrumentation to operate, automate, control and/or monitor aspects of the various processing steps performed in the system. This instrumentation in some embodiments is contained within a cabinet.

In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

The control circuitry in some aspects monitors and communicates information and instructions to and from the other instrumentation and various components of the system. In some embodiments, the cabinet contains a user interface device, comprising a display and an input device, such as a keyboard, a mouse, or a touchscreen. The user interface displays information from the control circuitry, allows the user to stop and start a process or steps, such as to effect a transduction protocol. The interface may also prompt the user to input settings for variables used by the control circuitry during a process step, such as a transduction protocol. Such variables may include volume of various solutions to be added and/or removed from the various containers and/or the cavity of the chamber, time/duration of sedimentation, centrifugation, agitation, mixing, and/or other process steps, rotational force, piston movement, and/or program selection.

The instrumentation generally further includes a centrifuge, into which the centrifuge chamber is placed in order to effect rotation of the chamber. In some embodiments, the centrifuge chamber is engaged with a rotary drive unit on the centrifuge apparatus, such that the chamber is rotatable about an axis of rotation. In some embodiments, a cover closes on top of the centrifuge chamber and holds the chamber in place. In some embodiments, the cover includes two semi-circular disks that can rotate on a hinge. An exemplary centrifuge and cover are described in U.S. Pat. No. 6,123,655 or U.S. Pat. No. 6,733,433. The centrifuge locks the centrifuge chamber into place and rotates the centrifuge chamber by contacting the chamber's sides or ends.

In some embodiments, a sensor or an array of sensors in the centrifuge can measure the rotational speed of the centrifuge chamber, the position of the movable member, or the volume contained within the internal cavity. Sensors outside of the centrifuge can detect the color and flow rate of liquid and gas flowing to and from the centrifuge chamber. Sensors can also detect an empty tubing or centrifuge chamber. Sensors include optical sensors, such as those described in U.S. Pat. Nos. 6,123,655, 6,733,433 and US 2008/0171951. In some embodiments, the information from the sensor or sensors can be received by control circuitry. Based on the information transmitted, the control circuitry, in some embodiments, can effect changes to one or more of the rotational speed of the centrifuge chamber, the position of the movable member, the volume contained in the cavity, the orientation of one or more valves, ports, seals or clamps, and other processes of the centrifuge, chamber or system.

In some embodiments, the cabinet includes a motor or array of motors. The motors can communicate information with the control circuitry, which can operate or adjust the motors.

In some embodiments, the motor or array of motors can rotate the centrifuge chamber within the centrifuge. The control circuitry can start, stop, or adjust the speed of the motors rotating the centrifuge chamber within the centrifuge.

In some embodiments, the motors or array of motors can move the movable member within the centrifuge chamber. Moving the movable member varies the volume of the internal cavity, causing the intake or expression of liquid or gas to or from the internal cavity.

In some embodiments, the motors or array of motors can operate the valves, ports, seals, and clamps described herein. The control circuitry can cause the motors to open, close, or direct fluid to or from a container or the centrifuge chamber through the series of tubing.

In some embodiments, the motor or motors is an electrical motor, pneumatic motor or hydraulic motor. In some embodiments, the cabinet includes an electrical motor for operating some aspects and a pneumatic motor for operating other aspects. In some embodiments, the cabinet includes an electrical motor for centrifugation and a pneumatic motor for controlling movement of the movable member.

III. Transfer of Viral Nucleic Acids to Cells, e.g., by Transduction

In some embodiments, the processing step(s) of the methods include those for transfer of viral particles to the cells, such as viral vectors encoding recombinant products to be expressed in the cells. The viral vector particles generally include a genome containing recombinant nucleic acids such as transgenes encoding such products. In some embodiments, the viral vector particles encode a recombinant receptor, such as a chimeric antigen receptor (CAR), whereby transduction of cells can generate recombinant receptor (e.g. CAR)-expressing cells. Transfer of the nucleic acid from the viral vector to the cells may use any of a number of known methods. Transfer is typically by transduction. Alternative methods for transferring viral vectors to cells include transposons and/or electroporation. Such processing steps can be performed in a centrifugal chamber according to embodiments of the provided methods. In some embodiments, the centrifugal chamber is integral to a closed system, such that such processing steps are performed in a closed system.

The transfer is generally carried out by transduction. The methods for viral transfer, e.g., transduction, generally involve at least initiation of transduction by incubating in a centrifugal chamber an input composition comprising the cells to be transduced and viral vector particles containing the vector, under conditions whereby cells are transduced or transduction is initiated in at least some of the cells in the input composition, wherein the method produces an output composition comprising the transduced cells.

In some embodiments, the cells for transduction and/or transduced cells contain immune cells, such as T cells, for use in adoptive immunotherapy. In some embodiments, prior to the incubation of cells with viral vector particles, the cells for transduction are obtained by methods that include isolating, such as selecting, a particular subset of cells present in a biological sample. Methods related to isolation and selection of cells for transduction, and the resulting cells, are described below. In some embodiments, prior to initiation of the processes for transduction, T cells are activated, such as by cultivation and stimulation as described below. In some embodiments, one or more of all or a part of the steps related to isolation, e.g. selection, and activation also can be carried out in the cavity of a centrifugal chamber according to provided embodiments as described below.

In some embodiments, the viral vector particles used in aspects of the transduction method are any suitable for transduction of the cells, such as an immune cell, for example a T cell. In some embodiments, the viral vector particles are retroviral vector particles, such as lentiviral vector particles or gammaretroviral vector particles. In some such embodiments, the viral vector particle contains a genome comprising a recombinant nucleic acid, i.e. a recombinant viral vector. Exemplary of such viral vector particles are described below.

The input composition (the composition that contains the viral vector particles and cells during the transduction step) may further include one or more additional agents, such as those to promote transduction efficiency, such as polycations including protamine (e.g. protamine sulfate), hexadimethrine bromide (POLYBRENE®, Abbott Laboratories Corp), and CH-296 (RETRONECTIN®, Clontech). In some embodiments, the polycation can be present in the input composition at a final concentration of 1 µg/mL to 100 µg/mL, such as 5 µg/mL to 50 µg/mL. The composition may also include media, including cell culture medium including medium designed for culture of the cell type to be processed, such as hematopoietic stem cell medium, e.g., serum free medium.

In the provided methods, all or a part of the processing steps for transduction of cells can occur in the centrifugal chamber, such as under centrifugation or rotation. In some such embodiments, the input composition containing the cells and the viral vector particles are provided to or taken into the internal cavity of the centrifugal chamber. In some embodiments, the input composition is incubated under conditions comprising rotation of the centrifugal chamber. In some embodiments, the rotation can be effected at relative centrifugal forces greater than can be achieved using flexible plastic bags or plastic multi-well plates.

Greater transduction efficiency is achieved in some embodiments in part due to the ability of the methods to carry out the transduction at a greater relative centrifugal force (RCF) compared with other methods for processing cells on large scales. For example, certain available methods for processing cells on a large scale, e.g., greater than 50 or 100 mL volume, using flexible bags, may only permit centrifugation at a relative centrifugal force of no more than 200, 500, or 1000 g. By allowing centrifugation at greater acceleration or relative force, e.g., at or about or at least at or about 1000, 1500, 2000, 2100, 2200, 2500, 3000 g, 3200 g or 3600 g, the provided methods can improve or permit co-sedimentation of virus and cells in the composition during transduction, improving the rate of virus-to-cell interactions, thereby improving transduction.

The methods generally are capable of conducting the transduction on a large scale. Thus, the input composition incubated during the transduction and/or output composition may contain at least a certain volume and/or number of cells. In some embodiments, the liquid volume of the input composition, or the liquid volume during at least a point during the incubation, is at least or greater than about 10 mL, 20 mL, 30 mL, 40 mL, 50 mL, 100 mL, 150 mL, 200 mL, 250 mL, 300 mL, 350 mL, 400 mL, 450 mL, or 500 mL. In some embodiments, the input composition, the transduced composition, and/or the total cells transduced by the methods include at least at or about $1 \times 10^5$, $1 \times 10^6$, $1 \times 10^7$, $1 \times 10^8$, $1 \times 10^9$, or $1 \times 10^{10}$ cells. In some embodiments, for at least a portion of the incubation, the vessel in which the cells are transduced, e.g., the centrifugal chamber or cavity thereof, contains at least at or about $1 \times 10^5$, $1 \times 10^6$, $1 \times 10^7$, $1 \times 10^8$, $1 \times 10^9$, or $1 \times 10^{10}$ cells. Such numbers and volume may also apply to other processing steps carried out in the system, e.g., in the cavity of the chamber, such as cell separation and/or washing steps.

In some embodiments, in describing the various processes steps in a cavity of the centrifugal chamber, including processes for transduction, such as preparation of the input composition, or other process as described in subsequent sections, reference to any volume is a target volume. In some embodiments, the exact volumes utilized in various steps (e.g. wash, dilution or formulation) can vary from a desired target volume, due to, in some aspects, dead volumes in a tubing line, priming of lines, sensitivity of a sensor, user control, and other factors associated with maintaining or monitoring a volume. The methods can permit precise control of volumes, such as by, in some aspects, inclusion of a sensor as part of the circuitry associated with the system. In some embodiments, volumes vary by no more than 10% of a desired target volume, such as no more than 9%, 8%, 7%, 6%, 5%, 4%, 3%, 2% or 1%. In some embodiments, volumes are within 2 mL or 3 mL of a target volume and/or vary by no more than 2 mL or 3 mL of a target volume.

In some embodiments, the processing steps are carried out by combining the cells and the viral vector particles to generate an input composition. In aspects of the method, the composition of cells and viral vector particles are prepared in a manner so that the resulting combined input composition has a low ratio of total liquid volume to internal surface area of the cavity of the centrifugal chamber. In some embodiments, the total liquid volume is sufficient to cover or just exceed a volume of cells present as a monolayer on the internal surface of the cavity after rotation of the centrifugal chamber, while minimizing the liquid thickness covering the cells. In some embodiments, reducing the liquid thickness can reduce the sedimentation time required for contacting of the viral vector particles with the cells because the viral vector particles have less of a distance to travel and/or are subjected to less resistance from the viscous medium.

In some embodiments, advantages such as improved transduction efficiency are due at least in part to the ability to use a relatively lower volume of liquid per volume of cells, cell number, or cell pellet size, during processes of transduction, such as during rotation, particularly compared with other methods for large-scale production.

In some embodiments, the liquid volume of the input composition (containing cells and viral vector particles) present in the vessel, e.g., cavity, during rotation is no more than about 0.5, 1, 2, 2.5, 3, 3.5, 4, 4.5, 5, 5.5, 6, 6.5, or 7 milliliters (mL) per square inch of the internal surface area of the cavity during the rotation or the maximum internal surface area of the cavity.

In particular embodiments, the average liquid volume of the input composition present in the vessel, e.g., cavity, in which transduction is initiated, such as the average of the liquid volume of all processes performed in a cycle of the method, is no more than about 0.5, 1, 2, 2.5, 3, 3.5, 4, 4.5, 5, 5.5, 6, 6.5, or 7 milliliters (mL) per square inch of the internal surface area of the cavity during the incubation or of the maximum internal surface area of the cavity. In some embodiments, the maximum liquid volume of the input composition (containing cells and viral vector particles) present in the vessel, e.g., cavity, in which transduction is initiated, such as the maximum of the liquid volume of all processes performed in a cycle of the method, is no more than about 0.5, 1, 2, 2.5, 3, 3.5, 4, 4.5, 5, 5.5, 6, 6.5, or 7 milliliters (mL) per square inch of the internal surface area of the cavity of the centrifugal chamber. In some embodiments, the liquid volume, such as the liquid volume of the input composition, present in the vessel, e.g., cavity, during rotation is no more than 50%, such as no more than 40%, no more than 30%, no more than 20% or no more than 10% of the volume of the internal surface area of the cavity during rotation or the maximum internal surface area of the cavity. In some embodiments, the remainder of the volume can be gas, such as air.

In some embodiments, the total liquid volume of the input composition (containing cells and viral vector particles) in the centrifugal chamber during incubation, such as during rotation, is at least 5 mL or at least 10 mL but is no more than 220 mL, such as no more than 200 mL. In some embodiments, the liquid volume of the input composition during incubation, such as during rotation, is no more than 100 mL, 90 mL, 80 mL, 70 mL, 60 mL, 50 mL, 40 mL, 30 mL or 20 mL. In aspects of the provided method, the input composition is prepared at such a total volume to achieve a desired concentration, amount and/or ratio of cells and viral vector particles, such as described below.

In some embodiments, the methods permit the user to control the ratio of cells to surface of the cavity, e.g., by varying the volume of the cavity and/or number of cells added. In some embodiments, this allows reduction of the layer of cells (e.g., cell pellet) on the surface of the cavity compared to other methods, particularly those available for large-scale transduction under centrifugal force, such as those carried out in centrifuge bags. In some embodiments, the ability to control the thickness of the layer of cells in the cavity of the centrifugal chamber during the transduction can lead to increased transduction efficiency under otherwise comparable conditions and/or a lack of increased copy number with increased virus transduction efficiency.

In some embodiments, the cells in the provided methods are present in the cavity in at or about a single monolayer, or no more than at or about 1.5 or 2-fold more than a single monolayer, or not substantially thicker than a monolayer, during the incubation for transduction under centrifugal force. This reduction during centrifugation can facilitate and improve interactions between the virus and cells and avoid increases in viral copy number (VCN) which can occur particularly in the context of high relative virus or infectious units (IU), for example, when outer or upper layers of cells are preferentially transduced.

In some embodiments, the input composition contains at least 1 million cells per $cm^2$ of the internal surface area of the cavity during at least a portion of said incubation, such as during rotation of the input composition in the centrifugal chamber. In some embodiments, the input composition contains at least 2 million cells per $cm^2$, 3 million cells per $cm^2$, 4 million cells per $cm^2$, 5 million cells per $cm^2$, 6 million cells per $cm^2$, 7 million cells per $cm^2$, 8 million cells per $cm^2$, 9 million cells per $cm^2$, 10 million cells per $cm^2$ or 20 million cells per $cm^2$ of the internal surface area of the cavity during at least a portion of said incubation, such as during rotation of the input composition in the centrifugal chamber. In some embodiments, the internal surface area of the cavity during at least a portion of said incubation, such as during rotation, is at least at or about $1 \times 10^9$ $\mu m^2$ or is at least at or about $1 \times 10^{10}$ $\mu m^2$.

In some embodiments, the total number of cells in the input composition during at least a portion of said incubation, such as during rotation of the input composition in the centrifugal chamber, is at least $10 \times 10^6$ cells, $20 \times 10^6$ cells, $30 \times 10^6$ cells, $40 \times 10^6$ cells, $50 \times 10^6$ cells, $60 \times 10^6$ cells, $70 \times 10^6$ cells, $80 \times 10^6$ cells, $100 \times 10^6$ cells, $200 \times 10^6$ cells, $300 \times 10^6$ cells or $400 \times 10^6$ cells.

In some embodiments, processing steps in the closed cavity of a centrifugal system also can be used to process the cells, such as activated cells, prior to transduction. In some embodiments, the processing can include dilution or concentration of the cells to a desired concentration or number. In some embodiments, the processing steps can include a volume-reduction to thereby increase the concentration of cells as desired. In some embodiments, the processing includes exchange of a medium into a medium acceptable or desired for transduction.

In some embodiments, the input composition comprises a certain ratio of copies of the viral vector particles or infectious units (IU) thereof, per total number of cells (IU/cell) in the input composition or total number of cells to be transduced. For example, in some embodiments, the input composition includes at or about or at least at or about 1, 2, 3, 4, 5, 10, 15, 20, 30, 40, 50, or 60 IU of the viral vector particles per one of the cells.

In certain embodiments, the ability to use a higher IU in the present methods provides advantages compared to other methods. Under otherwise identical conditions, use of a higher IU/cell ratio generally leads to a higher transduction efficiency, or does so up to a certain upper level of IU/cell at which the corresponding increase in efficiency may plateau. Nonetheless, with certain available methods, increasing the IU/cell and thus the transduction efficiency also leads to an increase in vector copy number (VCN), which can present safety risks and may not meet regulatory standards.

In some embodiments, with the provided methods, average VCN among transduced cells in the output composition, such as cells containing the viral vector or cells expressing a molecule encoded by the viral vector, does not increase with an increase in IU/cell in the input composition. In some embodiments, in the provided methods, the average VCN among transduced cells decreases with an increased IU/cell ratio in the input composition.

In some embodiments, the titer of viral vector particles is between or between about $1\times10^6$ IU/mL and $1\times10^8$ IU/mL, such as between or between about $5\times10^6$ IU/mL and $5\times10^7$ IU/mL, such as at least $6\times10^6$ IU/mL, $7\times10^6$ IU/mL, $8\times10^6$ IU/mL, $9\times10^6$ IU/mL, $1\times10^7$ IU/mL, $2\times10^7$ IU/mL, $3\times10^7$ IU/mL, $4\times10^7$ IU/mL, or $5\times10^7$ IU/mL.

In some embodiments, the input composition contains a concentration of viral vector particles during at least a portion of said incubation, such as during rotation of the input composition in the centrifugal chamber, that has a certain ratio of copies of the viral vector particles or infectious units (IU) thereof, per total number of cells (IU/cell) in the input composition or total number of cells to be transduced per total liquid volume of the input composition present during at least a portion of said incubation, such as during rotation, i.e. IU/cell/mL. In some embodiments, the input composition includes at least 0.01 IU, 0.05 IU, 0.1 IU, 0.5 IU or 0.1 IU of the viral vector particles per one of the cells per mL of the liquid volume of the input composition during at least a portion of said incubation, such as during rotation.

In some embodiments, the step of creating the input composition (cells and viral vector particles) can be performed in the centrifugal chamber. In some embodiments, the step of creating the input composition is performed outside the centrifugal chamber. Thus, the term "input composition" is not meant to imply that the entire composition is taken into the respective vessel, e.g., tube, bag, or cavity, at once, or to exclude the pulling in of parts of the composition from different vessels or lines. Input compositions may include those formed by pulling in two different compositions into the chamber's cavity and mixing the two, thereby creating the input composition.

The input composition may be taken into or otherwise transferred to the vessel in which the incubation, such as rotation, takes place from the same container or from more than one separate containers. For example, the input composition may be taken into the chamber by pulling in a composition containing the cells and another composition containing the viral vector particles, which may be done sequentially or simultaneously. Alternatively, the input composition containing the viral vector particles and cells is taken into the cavity or other vessel in which the transduction is to be carried out.

In some embodiments, where the transduction is carried out in the internal cavity of the centrifugal chamber, this is achieved by allowing only a certain portion of the cavity to include the liquid input composition. This may be achieved, for example, by pulling in air or gas into a portion of the cavity, and/or by including one or more solid object in a space within the cavity, such as an internal space. In some embodiments, this can minimize or reduce the total liquid volume of said input composition present in said cavity during incubation, such as during rotation, of said centrifugal chamber per square inch of the internal surface area of the cavity compared to the absence of gas in the cavity and/or absence of one or more solid objects in the space of the cavity. In this way, compared with other methods, in which diffusion of virus through a large volume of liquid compared to volume of cells may limit efficacy of transduction, the provided methods can be advantageous. Thus, whereas in some embodiments, the input composition occupies all or substantially all of the volume of the internal cavity during at least a portion of the incubation, in some embodiments, during at least a portion of the incubation, the input composition occupies only a portion of the volume of the internal cavity during said incubation.

In some such embodiments, the volume of the cavity during this at least a portion of the incubation may further include a gas taken into said cavity by the one or more opening, e.g., inlet, in the cavity, such as prior to or during said incubation. In some embodiments of the method, the air is sterilized or is sterile air. In some embodiments, the air is free of or substantially free of microbial contaminants or other potentially pathogenic agents.

In some embodiments, providing or taking in gas, such as air, can be effected in any manner that permits passage of air into the internal cavity of the centrifugal chamber, such as, in some aspects, without compromising the sterility of the closed system. In some embodiments, gas, such as air, can be added to a container under sterile conditions, and the container can be sterilely connected at a position on the system for transfer into the chamber. In some embodiments, the addition of gas, such as air, to the container, such as a bag, is effected under laminar flow conditions, such as in a biological safety cabinet or hood. In some such embodiments, the gas, such as air, is added to the container together with a liquid volume, such as a liquid volume containing a composition of cells and/or a liquid volume containing a composition of viral vector particles. Hence, in some embodiments, providing or taking in gas, such as air, into the internal cavity of the chamber occurs together or simultaneously with the providing or intake of one or both of the cells or viral vector particles that make up the input composition.

In some embodiments, the providing or taking in gas, such as air, into the chamber, is achieved using a syringe that can be attached to any luer lock associated with the system, and, that is operably connected to the internal cavity of the centrifugal chamber. In some embodiments, air is transferred into the syringe under sterile conditions, such as under laminar flow. In some embodiments, the syringe is a sterile syringe, such as, in some aspects, a syringe containing a movable plunger that is not exposed to the surrounding non-sterile environment. In some embodiments, the syringe contains a filter at its end to effect sterile transfer of gas, such as air, into the internal cavity of the chamber.

In some embodiments, providing or taking in gas, such as air, into the internal cavity of the chamber is achieved by the use of a filter operably connected to the internal cavity of the chamber via a sterile tubing line. In some such embodiments, the filter is a sterile or microbial filter as described with reference to an exemplary system, such as in some aspects, a filter as exemplified in FIG. 7. In some embodiments, a device is connected to the filter, such as via a luer lock connection, to transfer the air. In some such embodiments, the device is a syringe, pump, or other infusion device. In some embodiments, the gas is air, and the intake of air through the filter is directly from the surrounding environment. In some embodiments, the filter contains a cap, such as a non-vented cap, that is removable or detachable to control transfer of air into filter as desired.

Hence, in some embodiments, the methods include providing or taking in a liquid input composition and a volume of gas, such as air, into the internal cavity of the chamber. The volume of gas, such as air, that is provided or taken in is a function of the volume of composition containing cells and composition containing viral vector particles that make up the input composition. In some embodiments, the volume of gas is the difference between the total volume of the internal cavity and the liquid volume of the input composition. In some embodiments, the total volume of gas and liquid is no more than 200 mL, such that the volume of gas provided or taken in to the internal cavity is the difference between 200 mL and the liquid volume of the input composition (cells and viral vector particles).

In an exemplary aspect of the provided methods, the method of transduction includes providing to an internal cavity of a closed centrifugal chamber system, in which the internal cavity has a surface area of at least at or about $1 \times 10^9$ µm² or at least at or about $1 \times 10^{10}$ µm², a composition containing at least or about $50 \times 10^6$ cells in a volume that is no more than 100 mL. In some embodiments, the cell composition contains at least or about $100 \times 10^6$ cells or at least or about $200 \times 10^6$ cells in a volume that is no more no more than 50 mL, 40 mL, 30 mL, 20 mL, 10 mL or 5 mL. In some embodiments, prior to providing the cells to the internal cavity, the composition of cells are diluted or concentrated to a volume of no more than 100 mL, such as no more no more than 50 mL, 40 mL, 30 mL, 20 mL, 10 mL or 5 mL. In addition to the cell composition, the method also includes providing, in some aspects, a composition containing viral vector particles in an amount that is at least 1 IU/cell in a volume so that the total liquid volume, including from the composition containing cells, is less than the maximum volume of the internal cavity of the centrifugal chamber, such as no more than 200 mL, thereby generating the input composition. In some embodiments, the composition containing viral vector particles is provided in an amount that is at least 1.6 IU/cell, 1.8 IU/cell, 2.0 IU/cell, 2.4 IU/cell, 2.8 IU/cell, 3.2 IU/cell or 3.6 IU/cell. In some embodiments, the total liquid volume of the input composition is less than 100 mL, less than 90 mL, less than 80 mL, less than 60 mL, less than 40 mL, less than 20 mL. Optionally, the method also can include providing gas, such as air up to the total volume of the internal cavity, for example, so that the total volume occupied in the internal cavity of the centrifugal chamber is up to or about 200 mL.

In some embodiments, the composition containing cells and composition containing viral vector particles, and optionally air, can be combined or mixed prior to providing the compositions to the cavity. In some embodiments, the composition containing cells and composition containing viral vector particles, and optionally air, are provided separately and combined and mixed in the cavity. In some embodiments, a composition containing cells, a composition containing viral vector particles, and optionally air, can be provided to the internal cavity in any order. In any of such some embodiments, a composition containing cells and viral vector particles is the input composition once combined or mixed together, whether such is combined or mixed inside or outside the centrifugal chamber and/or whether cells and viral vector particles are provided to the centrifugal chamber together or separately, such as simultaneously or sequentially.

In some embodiments, intake of the volume of gas, such as air, occurs prior to the incubation, such as rotation, in the transduction method. In some embodiments, intake of the volume of gas, such as air, occurs during the incubation, such as rotation, in the transduction method.

In some embodiments, the liquid volume of the cells or viral vector particles that make up the input composition, and optionally the volume of air, can be a predetermined volume. The volume can be a volume that is programmed into and/or controlled by circuitry associated with the system.

In some embodiments, intake of the input composition, and optionally gas, such as air, is controlled manually, semi-automatically and/or automatically until a desired or predetermined volume has been taken into the internal cavity of the chamber. In some embodiments, a sensor associated with the system can detect liquid and/or gas flowing to and from the centrifuge chamber, such as via its color, flow rate and/or density, and can communicate with associated circuitry to stop or continue the intake as necessary until intake of such desired or predetermined volume has been achieved. In some aspects, a sensor that is programmed or able only to detect liquid in the system, but not gas (e.g. air), can be made able to permit passage of gas, such as air, into the system without stopping intake. In some such embodiments, a non-clear piece of tubing can be placed in the line near the sensor while intake of gas, such as air, is desired. In some embodiments, intake of gas, such as air, can be controlled manually.

In aspects of the provided methods, the internal cavity of the centrifuge chamber is subjected to high speed rotation. In some embodiments, rotation is effected prior to, simultaneously, subsequently or intermittently with intake of the liquid input composition, and optionally air. In some embodiments, rotation is effected subsequent to intake of the liquid input composition, and optionally air. In some embodiments, rotation is by centrifugation of the centrifugal chamber at a relative centrifugal force at the inner surface of side wall of the internal cavity and/or at a surface layer of the cells of at or about or at least at or about 800 g, 1000 g, 1100 g, 1500, 1600 g, 1800 g, 2000 g, 2200 g, 2500 g, 3000 g, 3500 g or 4000 g. In some embodiments, rotation is by centrifugation at a force that is greater than or about 1100 g, such as by greater than or about 1200 g, greater than or about 1400 g, greater than or about 1600 g, greater than or about 1800 g, greater than or about 2000 g, greater than or about 2400 g, greater than or about 2800 g, greater than or about 3000 g or greater than or about 3200 g.

In some embodiments, the method of transduction includes rotation or centrifugation of the input composition, and optionally air, in the centrifugal chamber for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes. In some embodiments, the input composition, and optionally air, is rotated or centrifuged in the centrifugal chamber for greater than 5 minutes, but for no more than 60 minutes, no more than 45 minutes, no more than 30 minutes or no more than 15 minutes.

In some embodiments, the method of transduction includes rotation or centrifugation of the input composition, and optionally air, in the centrifugal chamber for between or between about 10 minutes and 60 minutes, 15 minutes and 60 minutes, 15 minutes and 45 minutes, 30 minutes and 60 minutes or 45 minutes and 60 minutes, each inclusive, and at a force at the internal surface of the side wall of the internal cavity and/or at a surface layer of the cells of at least or greater than or about 1000 g, 1100 g, 1200 g, 1400 g, 1500 g, 1600 g, 1800 g, 2000 g, 2200 g, 2400 g, 2800 g, 3200 g or 3600 g.

In some embodiments, the method includes effecting expression from the internal cavity of the centrifugal chamber an output composition, which is the resulting composition of cells incubated with viral vector particles under conditions that include rotation or centrifugation in the centrifugal chamber in any of the above embodiments as described. In aspects of the method, the output composition includes cells transduced with, or in which transduction has been initiated with, a viral vector. In some embodiments, the expression of the output composition is to an output bag that is operably linked as part of a closed system with the centrifugal chamber. In some embodiments, expression of the output composition is subsequent to the rotation or centrifugation. In some embodiments, expression of the output composition is simultaneous with or partly simultaneous with the rotation or centrifugation, such as in a semi-continuous or continuous process.

In some embodiments, the gas, such as air, in the cavity of the chamber is expelled from the chamber. In some embodiments, the gas, such as air, is expelled to a container that is operably linked as part of the closed system with the centrifugal chamber. In some embodiments, the container is a free or empty container. In some embodiments, the air, such as gas, in the cavity of the chamber is expelled through a filter that is operably connected to the internal cavity of the chamber via a sterile tubing line. In some embodiments, the air is expelled using manual, semi-automatic or automatic processes. In some embodiments, air is expelled from the chamber prior to, simultaneously, intermittently or subsequently with expressing the output composition containing incubated cells and viral vector particles, such as cells in which transduction has been initiated or cells have been transduced with a viral vector, from the cavity of the chamber.

In some embodiments, the transduction and/or other incubation is performed as or as part of a continuous or semi-continuous process. In some embodiments, a continuous process involves the continuous intake of the cells and viral vector particles, e.g., the input composition (either as a single pre-existing composition or by continuously pulling into the same vessel, e.g., cavity, and thereby mixing, its parts), and/or the continuous expression or expulsion of liquid, and optionally expelling of gas (e.g. air), from the vessel, during at least a portion of the incubation, e.g., while centrifuging. In some embodiments, the continuous intake and continuous expression are carried out at least in part simultaneously. In some embodiments, the continuous intake occurs during part of the incubation, e.g., during part of the centrifugation, and the continuous expression occurs during a separate part of the incubation. The two may alternate. Thus, the continuous intake and expression, while carrying out the incubation, can allow for a greater overall volume of sample to be processed, e.g., transduced.

In some embodiments, the incubation is part of a continuous process, the method including, during at least a portion of the incubation, effecting continuous intake of said input composition into the cavity during rotation of the chamber and during a portion of the incubation, effecting continuous expression of liquid and, optionally expelling of gas (e.g. air), from the cavity through the at least one opening during rotation of the chamber.

In some embodiments, the semi-continuous incubation is carried out by alternating between effecting intake of the composition into the cavity, incubation, expression of liquid from the cavity and, optionally expelling of gas (e.g. air) from the cavity, such as to an output container, and then intake of a subsequent (e.g., second, third, etc.) composition containing more cells and other reagents for processing, e.g., viral vector particles, and repeating the process. For example, in some embodiments, the incubation is part of a semi-continuous process, the method including, prior to the incubation, effecting intake of the input composition into the cavity through said at least one opening, and subsequent to the incubation, effecting expression of fluid from the cavity; effecting intake of another input composition comprising cells and the viral vector particles into said internal cavity; and incubating the another input composition in said internal cavity under conditions whereby said cells in said another input composition are transduced with said vector. The process may be continued in an iterative fashion for a number of additional rounds. In this respect, the semi-continuous or continuous methods may permit production of even greater volume and/or number of cells.

In some embodiments, a portion of the transduction incubation is performed in the centrifugal chamber, which is performed under conditions that include rotation or centrifugation.

In some embodiments, the method includes an incubation in which a further portion of the incubation of the cells and viral vector particles is carried out without rotation or centrifugation, which generally is carried out subsequent to the at least portion of the incubation that includes rotation or centrifugation of the chamber. In some such embodiments, the further incubation is effected under conditions to result in integration of the viral vector into a host genome of one or more of the cells. It is within the level of a skilled artisan to assess or determine if the incubation has resulted in integration of viral vector particles into a host genome, and hence to empirically determine the conditions for a further incubation. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In some embodiments, the further incubation is carried out in the centrifuge chamber, but without rotation. In some embodiments, the further incubation is carried out outside of the centrifuge chamber. In some embodiments, the further incubation is effected at temperatures greater than room temperature, such as greater than or greater than about 25° C., such as generally greater than or greater than about 32° C., 35° C. or 37° C. In some embodiments, the further incubation is effected at a temperature of at or about 37° C.±2° C., such as at a temperature of at or about 37° C. In some embodiments, the further incubation is for a time between or about between 1 hour and 48 hours, 4 hours and 36 hours, 8 hours and 30 hours or 12 hours and 24 hours, inclusive.

In some embodiments, the further incubation occurs in a closed system. In some embodiments, after expression of the output composition from the chamber, such as into a container (e.g. bag), the container containing the output composition is incubated for a further portion of time. In some embodiments, the container, such as bag, is incubated at a temperature of at or about 37° C.±2° C. for a time between or about between 1 hour and 48 hours, 4 hours and 36 hours, 8 hours and 30 hours or 12 hours and 24 hours, inclusive.

In some embodiments, the methods effect transduction of a certain number or percentage of the cells in the input and/or output (transduced) composition, or subset thereof. For example, in some embodiments, at least 2.5%, at least 5%, at least 6%, at least 8%, at least 10%, at least 20%, at least 25%, at least 30%, at least 40%, at least 50%, or at least 75% of the total cells (or of a particular target cell type, such as T cells) in the input composition and/or in the output (e.g., transduced) composition, are transduced with said viral vector and/or express the recombinant gene product encoded thereby. In some embodiments, the methods of transduction result in an output composition in which at least 2.5%, at least 5%, at least 6%, at least 8%, at least 10%, at least 20%, at least 25%, at least 30%, at least 40%, at least 50%, or at least 75% of the total cells, such as T cells, in the composition are transduced with the viral vector and/or express the recombinant gene product encoded thereby.

In some embodiments, the methods are capable of achieving such at least a particular transduction efficiency under certain conditions. For example, in some embodiments, where the input composition includes the virus and cells at a ratio of from or from about 1 infectious unit (IU) per one of the cells to 10 IU per one of the cells, such as at or about 1infectious units (IU) per one of the cells, or at or about 2 IU per one of the cells, or at or about 5 IU per one of the cells, or at or about 10 IU per one of the cells, the method is capable of producing a transduced composition in which at least 10%, at least 25%, at least 30%, at least 40%, at least 50%, or at least 75% of the cells in said transduced composition generated by the method comprise, e.g., have been transduced with, the recombinant viral vector. Transduction of the cells may be detected by detecting the presence of recombinant nucleic acid, e.g., transgene, included in the vector or product thereof in the cell. In some embodiments, the product is detected on the surface of the cell, indicating the cell has been successfully transduced. In some embodiments, detection of transduction involves detection of a transduction marker, such as another transgene or product included for the purposes of marking transduced cells, and/or other selection marker.

In some embodiments, the output composition resulting from the transduction methods includes a particular average or mean number of copies of the transduced vector per cell (vector copy number (VCN)). VCN may be expressed in terms of the number of copies in a single cell. Alternatively, it may be expressed as an average number over a total cell population or composition, such as the output or transduced composition (including any non-transduced cells within the composition, which would not include any copies of the vector). Alternatively, VCN may be expressed in terms of average copy number only among the transduced cells. In some embodiments, among all the cells in the transduced or output composition produced by the methods, the average VCN is no more than at or about 10, 5, 4, 2.5, 1.5, or 1. In some embodiments, among the cells in the transduced or output composition that contain the recombinant viral vector or express the recombinant gene product, the average VCN is no more than at or about 4, 3, 2, 2.5, 1.5, or 1.

Also provided are compositions produced by any of the above methods. In some embodiments, the compositions contain at least $1\times10^7$ cells or $5\times10^7$ cells, such as at least $1\times10^8$ cells, $2\times10^8$ cells, $4\times10^8$ cells, $6\times10^8$, $8\times10^8$ cells or $1\times10^9$ cells, in which at least a plurality of cells are transduced with the recombinant viral vector. In some embodiments, the cells are T cells.

In some embodiments, by practice of the methods provided herein, it is possible to produce an output composition containing a plurality of transduced cells in high number, such as, in some aspects, a number that can achieve a therapeutically effective dosage of T cells for use in adoptive immunotherapy. In some embodiments, this can be achieved not only because of the ability to transduce cells on a large scale, but also, in some aspects, by repeating the process in a continuous or semi-continuous manner.

In contrast, existing methods in the art in which transduction is performed on a smaller scale, such as in plates, requires large scale expansion of the cells after transduction in order to achieve numbers of cells necessary to obtain a therapeutically effective dosage. Expansion of cells, such as T cells, with one or more stimulating agents can activate the cells and/or alter the phenotype of the cells, such as by resulting in the generation of effector cells with an exhausted T cell phenotype. For example, activation or stimulation of T cells can result in a change in differentiation or activation state of T cells that may result and/or lead to reduced persistence in vivo when genetically engineered cells are administered to a subject. Among changes in differentiation state that may occur include, in some cases, loss of a naïve phenotype, loss of memory T cell phenotypes, and/or the generation of effector cells with an exhausted T cell phenotype. Exhaustion of T cells may lead to a progressive loss of T cell functions and/or in depletion of the cells (Yi et al. (2010) Immunology, 129:474-481). T cell exhaustion and/or the lack of T cell persistence is a barrier to the efficacy and therapeutic outcomes of adoptive cell therapy; clinical trials have revealed a correlation between greater and/or longer degree of exposure to the antigen receptor (e.g. CAR)-expressing cells and treatment outcomes.

In some embodiments, in the methods provided herein it is not necessary to stimulate and/or activate cells subsequent to transduction to the same extent as is necessary in other known methods in the art. In some embodiments, subsequent to transduction, the cells in the composition are not subject to expansion in the presence of a stimulating agent (e.g. a cytokine, such as IL-2) and/or are not incubated at a temperature greater than or about 30° C. or greater than or about 37° C. for more than 24 hours. In some embodiments, at least 30%, 40%, 50%, 60%, 70%, 80%, or 90% of the T cells in the composition and/or transduced T cells in the output composition comprise high surface expression of CD69 or TGF-beta-II. In some embodiments, at least 30%, 40%, 50%, 60%, 70%, 80%, or 90% of the T cells or transduced T cells in the composition comprise no surface expression of CD62L and/or comprise high expression of CD25, ICAM, GM-CSF, IL-8 and/or IL-2.

In some embodiments, engineered cells, such as cells transduced with the viral vectors encoding recombinant products to be expressed in the cells, of the output composition produced by the above method, or by a method that includes a further processing step, such as to generate a formulated composition, exhibit increased persistence when administered in vivo to a subject. In some embodiments, the persistence of a provided cells, such as receptor, e.g., CAR, -expressing cells, in the subject upon administration is greater as compared to that which would be achieved by alternative methods of transduction, such as those involving administration of cells genetically engineered by methods involving smaller scale transduction in which T cells are activated and/or stimulated to expand prior to and/or subsequent to transduction to achieve a number of cells that is a therapeutically effective dose. For example, in some aspects, the persistence of provided cells, such as cells produced by the provided methods, is greater as compared to that which would be achieved by administration of a population of genetically engineered recombinant receptor (e.g. CAR)-expressing in which at least 30%, 40%, 50%, 60%, 70%, 80%, or 90% have a lower level of expression of CD69 or TGF-beta II. In some embodiments, the persistence of provided cells, such as cells produced by the provided methods, is greater compared to that which would be achieved by administration of a population of genetically engineered recombinant receptor (e.g. CAR)-expressing in which at least 30%, 40%, 50%, 60%, 70%, 80%, or 90% exhibit surface expression of CD62L and/or comprise low surface expression of CD25, ICAM, GM-CSF, IL-8 and/or IL-2.

In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

In some embodiments, by minimizing T cell activation and/or stimulation, the provided embodiments can result in genetically engineered T cells that are more potent for use in adoptive immunotherapy methods, due, in some aspects, to increased persistence. In some embodiments, the increased potency and/or increased persistence of the provided cells, such as cells produced by any of the provided methods, permits methods of administering cells at lower dosages. Such methods can minimize toxicity that can occur from adoptive immunotherapy methods.

Other Cell Processing Events

In some embodiments, in addition to and/or alternatively to the transduction steps, the processing methods of the provided methods include other processing steps and methods, such as for the isolation, separation, selection, cultivation (e.g., stimulation of the cells, for example, to induce their proliferation and/or activation), washing, suspension, dilution, concentration, and/or formulation of the cells. In some embodiments, at least a portion of one or more other processing steps and/or at least a portion of a plurality of the steps are carried out in whole or in part within the cavity of a centrifugal chamber, such as the same or different centrifugal chamber as used in the methods of transduction. In some embodiments, all or a portion of such one or more other processing steps are carried out in the closed system containing a centrifugal chamber, such as in a sterile closed system.

In some embodiments, the methods include one or more of (a) washing a biological sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) in a cavity of a chamber, (b) isolating, e.g. selecting, from the sample a desired subset or population of cells (e.g., CD4+ or CD8+ T cells) in a cavity of a chamber, for example, by incubation of cells with a selection or immunoaffinity reagent for immunoaffinity-based separation; c) incubating the isolated, such as selected cells, with viral vector particles, such as in accord with methods described above and d) formulating the transduced cells, such as in a pharmaceutically acceptable buffer, cryopreservative or other suitable medium. In some embodiments, the methods can further include (e) stimulating cells in a cavity of a chamber by exposing cells to stimulating conditions, thereby inducing cells to proliferate. In some embodiments, the step of stimulating the cells is performed prior to, during and/or subsequent to the incubation of cells with viral vector particles. In some embodiments, one or more further step of washing or suspending step, such as for dilution, concentration and/or buffer exchange of cells, can also be carried out prior to or subsequent to any of the above steps.

Thus, in some embodiments, the methods carry out one, more, or all steps in the preparation of cells for clinical use, e.g., in adoptive cell therapy, without exposing the cells to non-sterile conditions and without the need to use a sterile room or cabinet. In some embodiments of such a process, the cells are isolated, separated or selected, stimulated, transduced, washed, and formulated, all within a closed system. In some embodiments, the methods are carried out in an automated fashion. In some embodiments, one or more of the steps is carried out apart from the centrifugal chamber system.

Samples

In some embodiments, the processing steps include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some examples, cells from the circulating blood of a subject are obtained, e.g., by apheresis or leukapheresis. The samples may contain lymphocytes, including T cells, monocytes, granulocytes, B cells, other nucleated white blood cells, red blood cells, and/or platelets.

In some embodiments, the provided methods include processing, in whole or in part, one or more of the samples in a closed system, such as in a centrifugal chamber. In some embodiments, the processing step can involve washing of the sample, e.g., blood cell-containing sample, from the subject, e.g., to remove the plasma fraction and/or replacing the cells in an appropriate buffer or media for subsequent processing steps and/or performing a density-based cell separation methods, such as in the preparation of white blood cells from peripheral blood by lysing the red blood cells and centrifugation through a Percoll or Ficoll gradient. Exemplary of such processing steps can be performed using a centrifugal chamber in conjunction with one or more systems associated with a cell processing system, such as a centrifugal chamber produced and sold by Biosafe SA, including those for use with the Sepax® or Sepax 2® cell processing systems.

Affinity-Based Selection

The processing steps (e.g., carried out in the centrifugal chamber) may include isolation of cells from mixed populations and/or compositions, such as using one of various selection steps including density-based or other physical property-based separation methods and affinity-based selection. In some embodiments, the methods include selection in which all or a portion of the selection is carried out in the internal cavity of the centrifugal chamber, for example, under centrifugal rotation. In some embodiments, incubation of cells with selection reagents, such as immunoaffinity-based selection reagents, is performed in a centrifugal chamber. Such methods can offer certain advantages compared to other available selection methods.

For example, immunoaffinity-based selection can depend upon a favorable energetic interaction between the cells being separated and the molecule specifically binding to the marker on the cell, e.g., the antibody or other binding partner on the solid surface, e.g., particle. In certain available methods for affinity-based separation using particles such as beads, particles and cells are incubated in a container, such as a tube or bag, while shaking or mixing, with a constant cell density-to-particle (e.g., bead) ratio to aid in promoting energetically favored interactions. Such approaches may not be ideal for use with large-scale production, for example, in that they may require use of large volumes in order to maintain an optimal or desired cell-to-particle ratio while maintaining the desired number of cells. Accordingly, such approaches can require processing in batch mode or format, which can require increased time, number of steps, and handling, increasing cost and risk of user error.

In some embodiments, by conducting such selection steps or portions thereof (e.g., incubation with antibody-coated particles, e.g., magnetic beads) in the cavity of the centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

The incubation with a selection reagent or reagents, e.g., as part of selection methods which may be performed in the chamber cavity, include using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immuno-affinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the further selection is performed outside of the centrifugal chamber. In some embodiments, the separation is performed in the same closed system in which the centrifugal chamber is present and in which the incubation of cells with the selection reagent was performed. In some embodiments, after incubation with the selection reagents, incubated cells, including cells in which the selection reagent has bound, are expressed from the centrifugal chamber, such as transferred out of the centrifugal chamber, into a system for immunoaffinity-based separation of the cells. In some embodiments, the system for immunoaffinity-based separation is or contains a magnetic separation column. In some embodiments, prior to separation, one or more other processing steps can be performed in the chamber, such as washing.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In any of such examples, at least a portion of the further selection or selection steps is performed in a centrifugal chamber, which includes incubation of cells with a selection reagent, as described above.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, CD3+, CD28+ T cells can be positively selected using CD3/CD28 conjugated magnetic beads (e.g., DYNABEADS® M-450 CD3/CD28 T Cell Expander, and/or ExpACT® beads).

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker-high) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+T helper cells may be sorted into naïve, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, or CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, N.J.).

In some aspects, the incubated sample or composition of cells to be separated is incubated with a selection reagent containing small, magnetizable or magnetically responsive material, such as magnetically responsive particles or microparticles, such as paramagnetic beads (e.g., such as Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. Many well-known magnetically responsive materials for use in magnetic separation methods are known, e.g., those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 also may be used.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotech, Auburn, Calif.). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the processing steps include expression from the centrifugal chamber of cells incubated with one or more selection reagents. In some embodiments, the cells can be expressed subsequent to and/or continuous with one or more washing steps, which can, in some aspects, be performed in the centrifugal chamber.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

Freezing and Cryopreservation

In some embodiments, the cells, such as selected cells, are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively.

In some embodiments, the cells, such as selected cells, can be transferred to cryopreservation media using a centrifugal chamber in conjunction with one or more systems associated with a cell processing system, such as a centrifugal chamber produced and sold by Biosafe SA, including those for use with the Sepax® or Sepax 2® cell processing systems. In some embodiments, transfer to cryopreservation medium is associated with one or more processing steps that can involve washing of the sample, e.g., selected cell sample, such as to remove the selection media and/or replacing the cells in an appropriate cryopreservation buffer or media for subsequent freezing.

In some embodiments, the cells are frozen, e.g., cryopreserved, either before, during, or after said methods for processing. In some embodiments, the freeze and subsequent thaw step removes granulocytes and, to some extent, monocytes in the cell population. The cells are generally then frozen to −80° C. at a rate of 1° per minute and stored in the vapor phase of a liquid nitrogen storage tank.

Cultivation and Stimulation

In some embodiments, the processing steps (e.g., those carried out in the chamber and/or closed system) include cultivation, stimulation and/or activation of cells, such as by incubation and/or culture of cells. For example, in some embodiments, provided are methods for stimulating the isolated cells, such as selected cell populations. In some embodiments, the processing steps include incubation of a composition containing the cells, such as selected cells, where at least a portion of the incubation is in a centrifugal chamber and/or other vessel, e.g., under stimulating conditions. The incubation may be prior to or in connection with genetic engineering, such as genetic engineering resulting from embodiments of the transduction method described above. In some embodiments, the stimulation results in activation and/or proliferation of the cells, for example, prior to transduction.

In some embodiments, the processing steps include incubations of cells, such as selected cells, in which the incubation steps can include culture, cultivation, stimulation, activation, and/or propagation of cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell, such as agents suitable to deliver a primary signal, e.g., to initiate activation of an ITAM-induced signal, such as those specific for a TCR component, and/or an agent that promotes a costimulatory signal, such as one specific for a T cell costimulatory receptor, e.g., anti-CD3, anti-CD28, or anti-41-BB, for example, bound to solid support such as a bead, and/or one or more cytokines. Among the stimulating agents are anti-CD3/anti-CD28 beads (e.g., DYNABEADS® M-450 CD3/CD28 T Cell Expander, and/or ExpACT® beads). Optionally, the expansion method may further comprise the step of adding anti-CD3 and/or anti CD28 antibody to the culture medium. In some embodiments, the stimulating agents include IL-2 and/or IL-15, for example, an IL-2 concentration of at least about 10 units/mL. In some embodiments, incubation is carried out in accordance with techniques such as those described in U.S. Pat. No. 6,040,177 to Riddell et al., Klebanoff et al. (2012) J Immunother. 35(9):651-660, Terakura et al. (2012) Blood. 1:72-82, and/or Wang et al. (2012) J Immunother. 35(9):689-701.

In some embodiments, the T cells are expanded by adding to the composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions generally include a temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, at least a portion of the incubation with one or more stimulating conditions or stimulatory agents, such as any described above, is performed in a centrifugal chamber. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the total duration of the incubation with the stimulating agent is from or from about 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some cases, the total duration of the incubation in the centrifugal chamber is from or from about 5 minutes to 6 hours, such as 30 minutes to 3 hours, for example, at least or about at least 30 minutes, 60 minutes, 120 minutes or 180 minutes. In some cases, a further portion of the incubation can be performed outside of the centrifugal chamber.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, cells are incubated in a centrifugal chamber with a cell stimulating agent or agents that is/are a cell-binding agent, such as an antigen-binding reagent, such as antibody, that is able to induce intracellular signaling and/or cell proliferation. In some embodiments, cells are incubated with, including mixed with, anti-CD3/anti-CD28 beads in a centrifugal chamber according to aspects of processes in the provided methods.

In some embodiments, the processing steps include expression from the centrifugal chamber of cells incubated, such as mixed with, one or more stimulatory conditions or stimulating agents. In some embodiments, one or more other additional processing steps can be performed in the chamber, such as washing, which can be prior to, subsequent to and/or continuous with the stimulating incubation. In some embodiments, washing is performed prior to stimulation, such as on selected or thawed cells, to remove and replace media with a medium suitable for stimulation and cultivation of cells.

In some embodiments, expressed cells from the centrifugal chamber that have been incubated, such as mixed with, one or more stimulatory conditions or stimulating agents, are further incubated outside of the chamber. In some embodiments, the further incubation is effected at temperatures greater than room temperature, such as greater than or greater than about 25° C., such as generally greater than or greater than about 32° C., 35° C. or 37° C. In some embodiments, the further incubation is effected at a temperature of at or about 37° C.±2° C., such as at a temperature of at or about 37° C. In some embodiments, the further incubation is for a time between or about between 12 hours and 96 hours, such as at least or at least about 12 hours, 24 hours, 36 hours, 48 hours, 72 hours or 96 hours.

In some embodiments, the further incubation occurs in a closed system. In some embodiments, after expression from the chamber of the cells incubated, such as mixed, with one or stimulatory conditions or stimulating agents, such as into a container (e.g. bag), the container containing the cells is incubated for a further portion of time. In some embodiments, the container, such as bag, is incubated at a temperature of at or about 37° C.±2° C. for a time between or about between 1 hour and 48 hours, 4 hours and 36 hours, 8 hours and 30 hours or 12 hours and 24 hours, inclusive.

Formulation

In some embodiments, the process steps (e.g. carried out in the centrifugal chamber and/or closed system) may include formulation of cells, such as formulation of genetically engineered cells resulting from the provided transduction processing steps and/or one or more other processing steps as described. In some embodiments, the provided methods associated with formulation of cells include processing transduced cells, such as cells transduced and/or expanded using the processing steps described above, in a closed system, such as in or associated with a centrifugal chamber.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution.

In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired.

In some embodiments, the processing includes adding a volume of a formulation buffer to transduced and/or expanded cells. In some embodiments, the volume of formulation buffer is from or from about 10 mL to 1000 mL, such as at least or about at least or about or 50 mL, 100 mL, 200 mL, 300 mL, 400 mL, 500 mL, 600 mL, 700 mL, 800 mL, 900 mL or 1000 mL.

Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems.

In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as a bag that is operably linked as part of a closed system with the centrifugal chamber. In some embodiments, the container, such as bag, is connected to a system at an output line or output position as exemplified in the exemplary systems depicted in FIG. 5 or FIG. 7.

In some embodiments, the closed system, such as associated with a cell processing system, such as centrifugal chamber, includes a multi-port output kit containing a multi-way tubing manifold associated at each end of a tubing line with a port to which one or a plurality of containers can be connected for expression of the formulated composition. In some aspects, a desired number or plurality of output containers, e.g., bags, can be sterilely connected to one or more, generally two or more, such as at least 3, 4, 5, 6, 7, 8 or more of the ports of the multi-port output. For example, in some embodiments, one or more containers, e.g., bags can be attached to the ports, or to fewer than all of the ports. Thus, in some embodiments, the system can effect expression of the output composition into a plurality of output bags.

In some aspects, cells can be expressed to the one or more of the plurality of output bags in an amount for dosage administration, such as for a single unit dosage administration or multiple dosage administration. For example, in some embodiments, the output bags may each contain the number of cells for administration in a given dose or fraction thereof. Thus, each bag, in some aspects, may contain a single unit dose for administration or may contain a fraction of a desired dose such that more than one of the plurality of output bags, such as two of the output bags, or 3 of the output bags, together constitute a dose for administration.

Thus, the containers, e.g., bags, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags, individually comprises a unit dose of the cells. Thus in some embodiments, each of the containers comprises the same or approximately or substantially the same number of cells. In some embodiments, the unit dose includes less than about $1\times10^8$, less than about $5\times10^7$, less than about $1\times10^6$ or less than about $5\times10^5$ of cells, per kg of the subject to be treated and/or from which the cells have been derived. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each bag is 10 mL to 100 mL, such as at least or about at least 20 mL, 30 mL, 40 mL, 50 mL, 60 mL, 70 mL, 80 mL, 90 mL or 100 mL.

In some embodiments, one or more of the plurality of output bags can be used for testing, such as for assessing transduction efficiency. For example, the transduction efficiency in some aspects may be assessed by measuring the level of expression of a recombinant protein, such as a heterologous protein, encoded by a nucleic acid contained in the genome of the viral vector particle following transduction using embodiments of the provided methods. Thus, in some embodiments, the expression level of recombinant molecules may be assessed by any of a number of well-known methods such as detection by affinity-based methods, e.g., immunoaffinity-based methods, e.g., in the context of cell surface proteins, such as by flow cytometry. In some aspects, the cells contained in one or more of the plurality of containers, e.g., bags, is tested for the expression level of recombinant molecules by detection of a transduction marker and/or reporter construct. In other embodiments, expression is assessed using a nucleic acid encoding a truncated surface protein included within the vector as a marker.

In some embodiments, all or substantially all of a plurality of containers to which cells are expressed contain the same number of cells and in the same or substantially the same concentration. In some embodiments, prior to expressing cells into one of a plurality of containers, the tubing lines are primed.

IV. Cells and Compositions

Among the cells to be used in the methods, such as the processing steps, e.g., the transfer of viral nucleic acids, e.g., transduction, are cells, cell populations, and compositions.

The cells generally are mammalian cells, and typically are human cells. In some embodiments, the cells are derived from the blood, bone marrow, lymph, or lymphoid organs. In some aspects, the cells are cells of the immune system, such as cells of innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some embodiments, the methods include isolating cells from the subject, preparing, processing, culturing, and/or engineering them, and re-introducing them into the same subject, before or after cryopreservation, which, in some aspects, can be achieved in a closed system using one or more of the provided processing steps.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

V. Viral Vector Particles, Viral Vectors, and Encoded Recombinant Products

The transduction methods generally involve transduction with viral vectors, such as those encoding recombinant products to be expressed in the cells. The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Vectors include viral vectors, such as retroviral vectors, for example lentiviral or gammaretroviral vectors, having a genome carrying another nucleic acid and capable of inserting into a host genome for propagation thereof.

In some embodiments, a viral vector is transferred to a cell in a vehicle that is a viral vector particle, which includes a virion that encapsulates and/or packages a viral vector genome. In some such embodiments, the genome of the viral vector typically includes sequences in addition to the nucleic acid encoding the recombinant molecule that allow the genome to be packaged into the virus particle.

In some embodiments, the viral vector contains a recombinant nucleic acid, such as a nucleic acid encoding a recombinant and/or heterologous molecule, such as a recombinant or heterologous protein. In some embodiments, such as in aspects of the provided methods, transduction with the viral vectors produces an output composition, cells of which have been transduced and express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cells being transduced and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, recombinant nucleic acids are transferred into cells using recombinant virus or viral vector particles, such as, e.g., vectors derived from simian virus 40 (SV40), adenoviruses, adeno-associated virus (AAV). In some embodiments, recombinant nucleic acids are transferred into cells, such as T cells, using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

The viral vectors generally include recombinant nucleic acids such as transgenes encoding recombinant products to be expressed by the cells. Recombinant products include recombinant receptors, including antigen receptors such as functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, *Nature Reviews Clinical Oncology*, 10, 267-276 (2013); Wang et al. (2012) *J. Immunother.* 35(9): 689-701; and Brentjens et al., *Sci Transl Med.* 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine,* 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. In some aspects, the T cell costimulatory molecule is CD28 or 41BB.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

In some contexts, overexpression of a stimulatory factor (for example, a lymphokine or a cytokine) may be toxic to a subject. Thus, in some contexts, the viral vector introduces into the cell gene segments that cause the cells to be susceptible to negative selection in vivo, such as upon administration in adoptive immunotherapy. For example, in some aspects, following transduction of the cells with such gene segments, the cells are eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

Among additional nucleic acids that may be included in the viral vector for transduction and expression in the cells are those encoding products that improve the efficacy of therapy, such as by promoting viability and/or function of transferred cells; provide a genetic marker for selection and/or evaluation of the cells, such as to assess in vivo survival or localization, and/or improve safety, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

VI. Therapeutic Methods and Compositions

In some aspects, the products of the methods are used in methods of treatment, e.g., therapeutic methods, such as for administrating the cells and compositions to subjects in adoptive cell therapy. Also provided are such methods and uses of cells processed and produced by the methods, and pharmaceutical compositions and formulations for use therein. The provided methods generally involve administering the cells or compositions, e.g., output composition and/or formulated compositions, to subjects.

In some embodiments, the cells express recombinant receptors, such as CARs, or other antigen receptors, such as transgenic TCRs, e.g., those transferred in the transduction methods provided herein. Such cells generally are administered to subjects having a disease or condition specifically recognized by the receptor. In one embodiment, the cells express a recombinant receptor or a chimeric receptor, such as an antigen receptor, e.g. a CAR or a TCR, that specifically binds to a ligand associated with the disease or condition or expressed by a cell or tissue thereof. For example, in some embodiments, the receptor is an antigen receptor and the ligand is an antigen specific for and/or associated with the disease or condition. The administration generally effects an improvement in one or more symptoms of the disease or condition and/or treats or prevents the disease or condition or a symptom thereof. Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, antigen associated with the disease or disorder that is targeted by the cells or compositions is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EphA2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-AL mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the cells or compositions are administered in an amount that is effective to treat or prevent the disease or condition, such as a therapeutically effective or prophylactically effective amount. Thus, in some embodiments, the methods of administration include administration of the cells and compositions at effective amounts. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, and following isolation and processing the cells are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells, by multiple bolus administrations of the cells, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence.

Once the cells are administered to the subject (e.g., human), the biological activity of the cell populations in some aspects is measured by any of a number of known methods. Parameters to assess include specific binding of the cells to antigen, in vivo, e.g., by imaging, or ex vivo, e.g., by ELISA or flow cytometry. In certain embodiments, the ability of the cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In certain embodiments, the cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 111 (1995), and U.S. Pat. No. 5,087,616.

Also provided are pharmaceutical compositions or formulations for use in such methods, which in some embodiments are formulated in connection with the provided processing methods, such as in the closed system in which other processing steps are carried out, such as in an automated or partially automated fashion.

In some embodiments, the cells and compositions are administered to a subject in the form of a pharmaceutical composition or formulation, such as a composition comprising the cells or cell populations and a pharmaceutically acceptable carrier or excipient.

The term "pharmaceutical formulation" refers to a preparation which is in such form as to permit the biological activity of an active ingredient contained therein to be effective, and which contains no additional components which are unacceptably toxic to a subject to which the formulation would be administered.

The pharmaceutical compositions in some embodiments additionally comprise other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

Among the processing steps may include formulating such compositions.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be constructed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

VII. Exemplary Embodiments

Among the embodiments provided herein are:

1. A transduction method, comprising incubating, in an internal cavity of a centrifugal chamber, an input composition comprising cells and viral particles containing a recombinant viral vector, wherein
said centrifugal chamber is rotatable around an axis of rotation and comprises an end wall, a substantially rigid side wall extending from said end wall, and at least one opening, at least a portion of said side wall surrounding said internal cavity and said at least one opening being capable of permitting intake of liquid into said internal cavity and expression of liquid from said cavity;
the centrifugal chamber is rotating around said axis of rotation during at least a portion of the incubation; and
the method generates an output composition comprising a plurality of the cells transduced with the viral vector.

2. A transduction method, comprising incubating, in an internal cavity of a centrifugal chamber, an input composition comprising cells and a viral particle containing a recombinant viral vector,
said centrifugal chamber being rotatable around an axis of rotation and comprising an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity, wherein:
the centrifugal chamber is rotating around the axis of rotation during at least a portion of the incubation;
the total liquid volume of said input composition present in said cavity during rotation of said centrifugal chamber is no more than about 5 mL per square inch of the internal surface area of the cavity; and
the method generates an output composition comprising a plurality of the cells transduced with the viral vector.

3. The method of embodiment 1 or embodiment 2, wherein said rotating comprises rotation at a relative centrifugal force (RCF) at an internal surface of the side wall of the cavity and/or at a surface layer of the cells of greater than at or about 200 g, greater than at or about 300 g, or greater than at or about 500 g.

4. The method of any of embodiments 1-3, wherein said rotating comprises rotation at a relative centrifugal force at an internal surface of the side wall of the cavity and/or at a surface layer of the cells that is:
at or about 600 g, 800 g, 1000 g, 1100 g, 1600 g, 2000 g, 2100 g, 2200 g, 2500 g or 3000 g; or
at least at or about 600 g, 800 g, 1000 g, 1100 g, 1600 g, 2000 g, 2100 g, 2200 g, 2500 g or 3000 g.

5. The method of any of embodiments 1-4, wherein said rotating comprises rotation at a relative centrifugal force at an internal surface of the side wall of the cavity and/or at a surface layer of the cells that is between or between about 500 g and 2500 g, 500 g and 2000 g 500 g and 1600 g, 500 g an 1000 g, 600 g and 1600 g, 600 g and 1000 g, 1000 g and 2000 g or 1000 g and 1600 g, each inclusive.

6. The method of any of embodiments 1-5, wherein the at least a portion of the incubation during which the chamber is rotating is for a time that is:
greater than or about 5 minutes, greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes; or
between or between about 5 minutes and 60 minutes, 10 minutes and 60 minutes, 15 minutes and 60 minutes, 15 minutes and 45 minutes, 30 minutes and 60 minutes or 45 minutes and 60 minutes, each inclusive.

7. The transduction method of any of embodiments 1-6, wherein said centrifugal chamber further comprises a movable member and said internal cavity is a cavity of variable volume defined by said end wall, said substantially rigid side wall, and said movable member, said movable member being capable of moving within the chamber to vary the internal volume of the cavity.

8. The method of any of embodiments 1-7, wherein said side wall is curvilinear.

9. The method of embodiment 8, wherein said side wall is generally cylindrical.

10. The method of any of embodiments 7-9, wherein:
the movable member is a piston; and/or
the movable member is capable of axially moving within the chamber to vary the internal volume of the cavity.

11. The method of any of embodiments 1-10, wherein
said at least one opening comprises an inlet and an outlet, respectively capable of permitting said intake and expression; or
said at least one opening comprises a single inlet/outlet, capable of permitting said intake and said expression.

12. The method of any of embodiments 1-11, wherein said at least one opening is coaxial with the chamber and is located in the end wall.

13. The method of any of embodiments 1-12, wherein:
the internal surface area of said cavity is at least at or about $1 \times 10^9$ μm$^2$;
the internal surface area of said cavity is at least at or about $1 \times 10^{10}$ μm$^2$;
the length of said rigid wall in the direction extending from said end wall is at least about 5 cm;
the length of said rigid wall in the direction extending from said end wall is at least about 8 cm; and/or
the cavity comprises a radius of at least about 2 cm at at least one cross-section.

14. The method of any of embodiments 1-13, wherein:
the average liquid volume of said input composition present in said cavity during said incubation is no more than about 5 milliliters (mL) per square inch of the internal surface area of the cavity during said incubation;
the maximum liquid volume of said input composition present in said cavity at any one time during said incubation is no more than about 5 mL per square inch of the maximum internal surface area of the cavity;

the average liquid volume of said input composition present in said cavity during said incubation is no more than about 2.5 milliliters (mL) per square inch of the internal surface area of the cavity during said incubation; or the maximum liquid volume of said input composition present in said cavity at any one time during said incubation is no more than about 2.5 mL per square inch of the maximum internal surface area of the cavity.

15. The method of any of embodiments 1-14, wherein the liquid volume of said input composition present in said cavity during said rotation is between or between about 0.5 mL per square inch of the internal surface area of the cavity (mL/sq.in) and 5 mL/sq.in, 0.5 mL/sq.in. and 2.5 mL/sq.in., 0.5 mL/sq.in. and 1 mL/sq.in., 1 mL/sq.in. and 5 mL/sq.in., 1 mL/sq.in. and 2.5 mL/sq.in. or 2.5 mL/sq.in. and 5 mL/sq.in.

16. The method of any of embodiments 1-15, wherein:
the number of said cells in said input composition is at or about the number of said cells sufficient to form a monolayer on the surface of said cavity during rotation of said centrifugal chamber at a force of at or about 1000 g or at or about 2000 g at an internal surface of the side wall and/or at a surface layer of the cells; and/or the number of said cells in said input composition is no more than 1.5 times or 2 times the number of said cells sufficient to form a monolayer on the surface of said cavity during rotation of said centrifugal chamber at a force of at or about 1000 g or at or about 2000 g at an internal surface of the side wall and/or at a surface layer of the cells.

17. The method of any of embodiments 1-16, wherein
said input composition in the cavity comprises at least at or about $1\times10^6$ of said cells; or said input composition in the cavity comprises at least at or about $5\times10^6$ of said cells; or said input composition in the cavity comprises at least at or about $1\times10^7$ of said cells; or said input composition in the cavity comprises at least at or about $1\times10^8$ of said cells.

18. The method of any of embodiments 1-17, wherein said input composition in the cavity comprises at least at or about $1\times10^7$ of said cells, at least at or about $2\times10^7$ of said cells, at least at or about $3\times10^7$ of said cells, at least at or about $4\times10^7$ of said cells, at least at or about $5\times10^7$ of said cells, at least at or about $6\times10^7$ of said cells, at least at or about $7\times10^7$ of said cells, at least at or about $8\times10^7$ of said cells, at least at or about $9\times10^7$ of said cells, at least at or about $1\times10^8$ of said cells, at least at or about $2\times10^8$ of said cells, at least at or about $3\times10^8$ of said cells or at least at or about $4\times10^8$ of said cells.

19. The method of any of embodiments 1-18, wherein:
said input composition comprises at least at or about 1 infectious unit (IU) of viral particles per one of said cells, at least at or about 2 IU per one of said cells, at least at or about 3 IU per one of said cells, at least at or about 4 IU per one of said cells, at least at or about 5 IU per one of said cells, at least at or about 10 IU per one of said cells, at least at or about 20 IU per one of said cells, at least at or about 30 IU per one of said cells, at least at or about 40 IU per one of said cells, at least at or about 50 IU per one of said cells, or at least at or about 60 IU per one of said cells; or said input composition comprises at or about 1 infectious unit (IU) of viral particles per one of said cells, at or about 2 IU per one of said cells, at or about 3 IU per one of said cells, at or about 4 IU per one of said cells, at or about 5 IU per one of said cells, at or about 10 IU per one of said cells, at or about 20 IU per one of said cells, at or about 30 IU per one of said cells, at or about 40 IU per one of said cells, at or about 50 IU per one of said cells, or at or about 60 IU per one of said cells.

20. The method of any of embodiments 1-19, wherein:
the maximum total liquid volume of said input composition present in said cavity at any one time during said incubation is no more than 2 times, no more than 10 times, or no more than 100 times, the total volume of said cells in said cavity or the average volume of the input composition over the course of the incubation is no more than 2, 10, or 100 times the total volume of cells in the cavity.

21. The method of any of embodiments 1-20, wherein the maximum volume of said input composition present in said cavity at any one time during said incubation or the average volume over the course of the incubation is no more than at or about 2 times, 10 times, 25 times, 50 times, 100 times, 500 times, or 1000 times the volume of a monolayer of said cells formed on the inner surface of said cavity during rotation of said chamber at a force of at or about 1000 g or at or about 2000 g at an internal surface of the side wall and/or at a surface layer of the cells.

22. The method of any of embodiments 1-21, wherein the liquid volume of the input composition is no more than 20 mL, no more than 40 mL, no more than 50 mL, no more than 70 mL, no more than 100 mL, no more than 120 mL, no more than 150 mL or no more than 200 mL.

23. The method of any of embodiments 1-22, wherein the input composition occupies all or substantially all of the volume of the internal cavity during at least a portion of said incubation.

24. The method of any of embodiments 1-23, wherein, during at least a portion of the incubation in the chamber or during the rotation of the chamber, the liquid volume of the input composition occupies only a portion of the volume of the internal cavity of the chamber, the volume of the cavity during said at least a portion or during said rotation further comprising a gas, said gas taken into said cavity via said at least one opening, prior to or during said incubation.

25. The method of embodiment 24, wherein the centrifugal chamber comprises a movable member, whereby intake of gas into the centrifugal chamber effects movement of the movable member to increase the volume of the internal cavity of the chamber, thereby decreasing the total liquid volume of said input composition present in said cavity during rotation of said centrifugal chamber per square inch of the internal surface area of the cavity compared to the absence of gas in the chamber.

26. A method of transduction, comprising:
a) providing to an internal cavity of a centrifugal chamber that has an internal surface area of at least at or about $1\times10^9$ μm$^2$ or at least at or about $1\times10^{10}$
   i) an input composition comprising cells and viral particles comprising a recombinant viral vector, wherein:
      the number of cells in the input composition is at least $1\times10^7$ cells, and
      the viral particles are present in the input composition at at least at or about 1 infectious unit (IU) per one of said cells, and
      the input composition comprises a liquid volume that is less than the maximum volume of the internal cavity of the centrifugal chamber; and ii) gas at a volume that is up to the remainder of the maximum volume of the internal cavity of the centrifugal chamber; and b) incubating the input composition, wherein at least a portion of the incubation is carried out in said internal cavity of said centrifugal chamber while effecting rotation of said centrifugal chamber; and wherein the method generates an output composition comprising a plurality of the cells transduced with the viral vector.

27. The method of embodiment 26, wherein:
the number of cells is at least at or about $50 \times 10^6$ cells; $100 \times 10^6$ cells; or $200 \times 10^6$ cells; and/or
the viral particles are present at at least 1.6 IU/cell, 1.8 IU/cell, 2.0 IU/cell, 2.4 IU/cell, 2.8 IU/cell, 3.2 IU/cell or 3.6 IU/cell, 4.0 IU/cell, 5.0 IU/cell, 6.0 IU/cell, 7.0 IU/cell, 8.0 IU/cell, 9.0 IU/cell or 10.0 IU/cell.

28. The method of embodiment 26 or embodiment 27, wherein:
the liquid volume of the input composition is less than or equal to 200 mL, less than or equal to 100 mL, less than or equal to 50 mL or less than or equal to 20 mL; and/or
the liquid volume of the input composition is no more than 50%, no more than 40%, no more than 30%, no more than 20%, or no more than 10% of the volume of the internal surface area of the cavity during rotation or the maximum internal surface area of the cavity.

29. The method of any of embodiments 26-28, wherein the volume of gas is up to 200 mL, up to 180 mL, up to 140 mL or up to 100 mL.

30. The method of any of embodiments 26-29, wherein said rotation is at a relative centrifugal force at an internal surface of the side wall of the cavity or at a surface layer of the cells of at least at or about 600 g, 800 g, 1000 g, 1100 g, 1500 g, 1600 g, 2000 g, 2400 g, 2600 g, 2800 g, 3000 g, 3200 g or 3600 g.

31. A method of transduction, comprising incubating an input composition comprising cells and viral particles comprising a recombinant viral vector, at least a portion of said incubating being carried out under rotating conditions, thereby generating an output composition comprising a plurality of the cells transduced with the viral vector, wherein:
said input composition comprises greater than or about 20 mL, 50 mL, at least 100 mL, or at least 150 mL in volume, and/or said input composition comprises at least $1 \times 10^8$ cells; and
said rotating conditions comprise a relative centrifugal force on a surface layer of the cells of greater than about 800 g or greater than about 1000 g or greater than about 1500 g.

32. The method of embodiment 31, wherein:
at least 25% or at least 50% of said cells in the output composition are transduced with said viral vector; and/or
at least 25% or at least 50% of said cells in the output composition express a product of a heterologous nucleic acid comprised within said viral vector.

33. The method of embodiment 31 or embodiment 32, wherein said incubation is carried out in a cavity of a centrifugal chamber and the number of said cells in said input composition is at or about the number of said cells sufficient to form a monolayer or a bilayer on the inner surface of said cavity during said rotation.

34. The method of embodiment 33, wherein said centrifugal chamber comprises an end wall, a substantially rigid side wall extending from said end wall, and at least one opening, wherein at least a portion of said side wall surrounds said internal cavity and said at least one opening is capable of permitting intake of fluid into said internal cavity and expression of fluid from said cavity.

35. The method of embodiment 34, wherein said centrifugal chamber further comprises a movable member and said internal cavity is a cavity of variable volume defined by said end wall, said substantially rigid side wall, and said movable member, said movable member being capable of moving within the chamber to vary the internal volume of the cavity.

36. The method of any of embodiments 1-30 or 33-35, wherein the input composition in said cavity comprises a liquid volume of at least 20 mL or at least 50 mL and at or about 1 million cells per $cm^2$ of the internal surface area of the cavity during at least a portion of said incubation.

37. The method of any of embodiments 1-36, wherein a further portion of the incubation is carried out outside of the centrifugal chamber and/or without rotation, said further portion carried out subsequent to the at least a portion carried out in the chamber and/or with rotation.

38. The method of any of embodiments 1-37, wherein the at least a portion of the incubation carried out in the cavity of the centrifugal chamber and/or the further portion of the incubation is effected at or at about 37° C.±2° C.

39. The method of embodiment 37 or embodiment 38, wherein the incubation further comprises transferring at least a plurality of the cells to a container during said incubation and said further portion of the incubation is effected in the container.

40. The method of embodiment 39, wherein the transferring is performed within a closed system, wherein the centrifugal chamber and container are integral to the closed system.

41. The method of any of embodiments 37-40, wherein:
the incubation is carried out for a time between at or about 1 hour and at or about 96 hours, between at or about 4 hours and at or about 72 hours, between at or about 8 hours and at or about 48 hours, between at or about 12 hours and at or about 36 hours, between at or about 6 hours and at or about 24 hours, between at or about 36 hours and at or about 96 hours, inclusive; or
the further portion of the incubation is carried out for a time between at or about 1 hour and at or about 96 hours, between at or about 4 hours and at or about 72 hours, between at or about 8 hours and at or about 48 hours, between at or about 12 hours and at or about 36 hours, between at or about 6 hours and at or about 24 hours, between at or about 36 hours and at or about 96 hours, inclusive.

42. The method of any of embodiments 37-41, wherein:
the incubation is carried out for a time that is no more than 48 hours, no more than 36 hours or no more than 24 hours; or
the further portion of the incubation is carried out for a time that is no more than 48 hours, no more than 36 hours or no more than 24 hours.

43. The method of any of embodiments 37-41, wherein:
the incubation is performed in the presence of a stimulating agent; and/or
the further portion of the incubation is performed in the presence of a stimulating agent.

44. The method of any of embodiments 37-41, wherein:
the incubation is carried out for a time that is no more than 24 hours;
the cells in the composition have not been subjected to a temperature of greater than 30° C. for more than 24 hours; and/or the incubation is not performed in the presence of a stimulating agent.

45. The method of embodiment 43 or embodiment 44, wherein the stimulating agent is an agent capable of inducing proliferation of T cells, CD4+ T cells and/or CD8+ T cells.

46. The method of any of embodiments 43-45, wherein the stimulating agent is a cytokine selected from among IL-2, IL-15 and IL-7.

47. The method of any of embodiments 1-46, wherein the output composition containing transduced cells comprises at least at or about $1\times10^7$ cells or at least at or about $5\times10^7$ cells.

48. The method of embodiment 47, wherein the output composition containing transduced cells comprises at least at or about $1\times10^8$ cells, $2\times10^8$ cells, $4\times10^8$ cells, $6\times10^8$, $8\times10^8$ cells or $1\times10^9$ cells.

49. The method of embodiment 47 or embodiment 48, wherein the cells are T cells.

50. The method of embodiment 49, wherein the T cells are unfractionated T cells, isolated CD4+ T cells and/or isolated CD8+ T cells.

51. The method of any of embodiments 1-50, wherein the method results in integration of the viral vector into a host genome of one or more of the at least a plurality of cells and/or into a host genome of at least at or about 20% or at least at or about 30% or at least at or about 40% of the cells in the output composition.

52. The method of any of embodiments 1-51, wherein:
at least 2.5%, at least 5%, at least 6%, at least 8%, at least 10%, at least 20%, at least 25%, at least 30%, at least 40%, at least 50%, or at least 75% of said cells in said input composition are transduced with said viral vector by the method; and/or
at least 2.5%, at least 5%, at least 6%, at least 8%, at least 10%, at least 20%, at least 25%, at least 30%, at least 40%, at least 50%, or at least 75% of said cells in said output composition are transduced with said viral vector; and/or
at least 2.5%, at least 5%, at least 6%, at least 8%, at least 10%, at least 20%, at least 25%, at least 30%, at least 40%, at least 50%, or at least 75% of said cells in said output composition express a product of a heterologous nucleic acid comprised within said viral vector.

53. The method of any of embodiments 1-52, wherein, for an input composition comprising a virus at a ratio of about 1 or about 2 IU per cells, said method is capable of producing an output composition in which at least 10%, at least 25%, at least 30%, at least 40%, at least 50%, or at least 75% of the cells in said output composition generated by the method comprise said recombinant viral vector and/or express a product of a recombinant nucleic acid comprised within said vector.

54. The method of any of embodiments 1-53, wherein:
among all the cells in said output composition that contain the recombinant viral vector or into which the viral vector is integrated, the average copy number of said recombinant viral vector is no more than about 10, no more than about 5, no more than about 2.5, or no more than about 1.5; or
among the cells in the output composition, the average copy number of said vector is no more than about 2, no more than about 1.5, or no more than about 1.

55. The method of any of embodiments 1-30 and 33-54, wherein the centrifugal chamber is integral to a closed system, said closed system comprising said chamber and at least one tubing line operably linked to the at least one opening via at least one connector, whereby liquid and gas are permitted to move between said cavity and said at least one tubing line in at least one configuration of said system.

56. The method of embodiment 55, wherein:
said at least one tubing line comprises a series of tubing lines;
said at least one connector comprises a plurality of connectors; and
said closed system further comprises at least one container operably linked to said series of tubing lines, the connection permitting liquid and/or gas to pass between said at least one container and said at least one opening via the series of tubing lines.

57. The method of embodiment 55 or 56, wherein said at least one connector comprises a connector selected from the group consisting of valves, luer ports, and spikes.

58. The method of any of embodiments 55-57, wherein said at least one connector comprises a rotational valve.

59. The method of embodiment 58, wherein said rotational valve is a stopcock or multirotational port.

60. The method of any of embodiments 55-59, wherein said at least one connector comprises an aseptic connector.

61. The method of any of embodiments 56-60, wherein said at least one container comprises a container selected from the group consisting of bags, vials, and syringes.

62. The method of any of embodiments 56-61, wherein said at least one container comprises a diluent container, a waste container, a product collection container, and/or an input product container.

63. The method of any of embodiments 56-62, wherein:
said at least one container comprises at least one input container comprising said viral vector particles and said cells, a waste container, a product container, and at least one diluent container, each connected to said cavity via said series of tubing lines and said at least one opening.

64. The method of embodiment 63, wherein said method further comprises, prior to and/or during said incubation, effecting intake of said input composition into said cavity, said intake comprising flowing of liquid from said at least one input container into said cavity through said at least one opening.

65. The method of any of embodiments 56-64, wherein at least one container further comprises a container that comprises a gas prior to and/or during at least a point during said incubation and/or the closed system further comprises a microbial filter capable of taking in gas to the internal cavity of the centrifugal chamber and/or the closed system contains a syringe port for effecting intake of gas.

66. The method of embodiment 65, wherein the method comprises, prior to and/or during said incubation, providing or effecting intake of gas into said cavity under sterile conditions, said intake being effected by (a) flow of gas from the container that comprises gas, (b) flow of gas from an environment external to the closed system, via the microbial filter, or (c) flow of gas from a syringe connected to the system at the syringe port.

67. The method of embodiment 66, wherein the effecting intake of the gas into the internal cavity of the centrifugal chamber is carried out simultaneously or together with the effecting intake of the input composition to the internal cavity of the centrifugal chamber.

68. The method of embodiment 66 or embodiment 67, wherein the input composition and gas are combined in a single container under sterile conditions outside of the chamber prior to said intake of said input composition and gas into the internal cavity of the centrifugal chamber.

69. The method of embodiment 68, wherein the effecting of the intake of the gas is carried out separately, either simultaneously or sequentially, from the effecting of the intake of the input composition into said cavity.

70. The method of any of embodiments 66-69, wherein the intake of gas is effected by permitting or causing flow of the gas from a sterile closed container comprising the gas, an external environment through a microbial filter, or a syringe comprising said gas.

71. The method of any of embodiments 24-70, wherein the gas is air.

72. The method of any of embodiments 1-71, wherein the incubation is part of a continuous process, the method further comprising:
   during at least a portion of said incubation, effecting continuous intake of said input composition into said cavity during rotation of the chamber; and
   during a portion of said incubation, effecting continuous expression of liquid from said cavity through said at least one opening during rotation of the chamber.

73. The method of embodiment 72, further comprising:
   during a portion of said incubation, effecting continuous intake of gas into said cavity during rotation of the chamber; and/or
   during a portion of said incubation, effecting continuous expression of gas from said cavity.

74. The method of embodiment 73, wherein the method comprises the expression of liquid and the expression of gas from said cavity, where each is expressed, simultaneously or sequentially, into a different container.

75. The method of any of embodiments 72-74, wherein at least a portion of the continuous intake and the continuous expression occur simultaneously.

76. The method of any of embodiments 1-75, wherein the incubation is part of a semi-continuous process, the method further comprising:
   prior to said incubation, effecting intake of said input composition, and optionally gas, into said cavity through said at least one opening;
   subsequent to said incubation, effecting expression of liquid and/or optionally gas from said cavity;
   effecting intake of another input composition comprising cells and said viral particles containing a recombinant viral vector, and optionally gas, into said internal cavity; and
   incubating said another input composition in said internal cavity,
   wherein the method generates another output composition comprising a plurality of cells of the another input composition that are transduced with said viral vector.

77. The method of any of embodiments 64-76, wherein said providing or said intake of the input composition into the cavity comprises:
   intake of a single composition comprising the cells and the viral particles containing the recombinant viral vector; or
   intake of a composition comprising the cells and a separate composition comprising the viral particles containing the recombinant viral vector, whereby the compositions are mixed, effecting intake of the input composition.

78. The method of embodiment 64-77, wherein the method further comprises:
   effecting rotation of said centrifugal chamber prior to and/or during said incubation;
   effecting expression of liquid from said cavity into said waste container following said incubation;
   effecting expression of liquid from said at least one diluent container into said cavity via said at least one opening and effecting mixing of the contents of said cavity; and
   effecting expression of liquid from said cavity into said product container, thereby transferring cells transduced with the viral vector into said product container.

79. The method of any of embodiments 1-78, further comprising:
   (a) washing a biological sample comprising said cells in an internal cavity of a centrifugal chamber prior to said incubation; and/or
   (b) isolating said cells from a biological sample, wherein at least a portion of the isolation step is performed in an internal cavity of a centrifugal chamber prior to said incubation; and/or
   (c) stimulating cells prior to and/or during said incubation, said stimulating comprising exposing said cells to stimulating conditions, thereby inducing cells of the input composition to proliferate, wherein at least a portion of the step of stimulating cells is performed in an internal cavity of a centrifugal chamber.

80. The method of embodiment 79, wherein said isolating comprises carrying out immunoaffinity-based selection.

81. The method of embodiment 79 or 80, wherein said stimulating conditions comprise the presence of an agent capable of activating one or more intracellular signaling domains of one or more components of a TCR complex.

82. The method of embodiment 81, wherein said agent comprises a primary agent that specifically binds to a member of a TCR complex and a secondary agent that specifically binds to a T cell costimulatory molecule.

83. The method of embodiment 82, wherein the primary agent specifically binds to CD3; and/or
   the costimulatory molecule is selected from the group consisting of CD28, CD137 (4-1-BB), OX40, or ICOS.

84. The method of embodiment 83, wherein said primary and secondary agents comprise antibodies and/or are present on the surface of a solid support.

85. The method of any of embodiments 79-84, wherein said biological sample in (a) and/or in (b) is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

86. The method of any of embodiments 1-85, further comprising formulating cells transduced by the method in a pharmaceutically acceptable buffer in an internal cavity of a centrifugal chamber, thereby producing a formulated composition.

87. The method of embodiment 86, further comprising effecting expression of the formulated composition to one or a plurality of containers.

88. The method of embodiment 87, wherein the effecting of expression of the formulated composition comprises effecting expression of a number of the cells present in a single unit dose to one or each of said one or a plurality of containers.

89. The method of any of embodiments 79-88, wherein each of said a cavity of a centrifugal chamber is the same or different as a cavity of a centrifugal employed in one or more of the other steps and/or in the process of incubating and/or rotating an input composition containing cells and viral particles.

90. The method of any of embodiments 79-89, wherein each of said centrifugal chambers is integral to a closed system, said closed system comprising said chamber and at least one tubing line operably linked to the at least one opening via at least one connector, whereby liquid and gas are permitted to move between said cavity and said at least one tubing line in at least one configuration of said system.

91. The method of any of embodiments 1-90, wherein said cells in said input composition are primary cells.

92. The method of any of embodiments 1-91, wherein:
said cells in said input composition comprise suspension cells;
said cells in said input composition comprise white blood cells; and/or
said cells in said input composition comprise T cells or NK cells.

93. The method of any of embodiments 1-92, wherein said cells in said input composition are unfractionated T cells, isolated CD8$^+$ T cells, or isolated CD4$^+$ T cells.

94. The method of any of embodiments 1-93, wherein said cells in said input composition are human cells.

95. The method of any of embodiments 7-94, wherein, during said incubation, said centrifugal chamber is associated with a sensor, said sensor capable of monitoring the position of said movable member, and control circuitry, said circuitry capable of receiving and transmitting information to and from said sensor and causing movement of said movable member, said control circuitry further associated with a centrifuge capable of causing rotation of said chamber during said incubation.

96. The method of any of embodiments 7-95, wherein said chamber comprises said movable member and during said incubation, said centrifugal chamber is located within a centrifuge and associated with a sensor, said sensor capable of monitoring the position of said movable member, and control circuitry capable of receiving and transmitting information from said sensor and causing movement of said movable member, intake and expression of liquid and/or gas to and from said cavity via said one or more tubing lines, and rotation of said chamber via said centrifuge.

97. The method of embodiment 95 or embodiment 96, wherein said chamber, said control circuitry, said centrifuge, and said sensor are housed within a cabinet during said incubation.

98. The method of any of embodiments 1-97, wherein said recombinant viral vector encodes a recombinant receptor, which is thereby expressed by cells of the output composition.

99. The method of embodiment 98, wherein said recombinant receptor is a recombinant antigen receptor.

100. The method of embodiment 99, wherein said recombinant antigen receptor is a functional non-T cell receptor.

101. The method of embodiment 100, wherein said functional non-T cell receptor is a chimeric antigen receptor (CAR).

102. The method of embodiment 99, wherein said recombinant antigen receptor is a transgenic T cell receptor (TCR).

103. The method of embodiment 99, wherein said recombinant receptor is a chimeric receptor comprising an extracellular portion that specifically binds to a ligand and an intracellular signaling portion containing an activating domain and a costimulatory domain.

104. The method of any of embodiments 1-103, wherein:
the cells comprise primary human T cells obtained from a human subject; and
prior to said incubation and/or prior to completion of said transduction and/or, where the method includes formulation, prior to the formulation, the primary human T cells have not been present externally to the subject at a temperature of greater than 30° C. for greater than 1 hour, greater than 6 hours, greater than 24 hours, or greater than 48 hours; or
prior to said incubation and/or prior to the completion of the transduction, and/or where the method includes formulation, prior to the formulation, the primary human T cells have not been incubated in the presence of an antibody specific for CD3 and/or an antibody specific for CD28 and/or a cytokine, for greater than 1 hour, greater than 6 hours, greater than 24 hours, or greater than 48 hours.

105. A method for selection, the method comprising:
(a) incubating a selection reagent and primary cells in an internal cavity of a centrifugal chamber under mixing conditions, whereby a plurality of the primary cells bind to said selection reagent; and
(b) separating said plurality of said primary cells from another one or more of the primary cells based on binding to the selection reagent,
thereby enriching the primary cells based on binding to the selection reagent,
wherein said centrifugal chamber is rotatable around an axis of rotation and said internal cavity has a maximum volume of at least 50, at least 100, or at least 200 mL.

106. A method for stimulation of cells, the method comprising incubating a stimulation agent and primary cells under conditions whereby the stimulation agent binds to a molecule expressed by a plurality of the primary cells and said plurality of the cells are activated or stimulated, wherein
at least a portion of the incubation being carried out in an internal cavity of a centrifugal chamber under mixing conditions,
said centrifugal chamber is rotatable around an axis of rotation; and
said internal cavity has a maximum volume of at least 50, at least 100, or at least 200 mL.

107. The method of embodiment 105 or embodiment 106, wherein the chamber further comprises an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity.

108. A composition, comprising transduced cells produced by the method of any of embodiments 1-107.

109. The composition of embodiment 108, wherein said cells:
are primary cells; and/or
are human cells; and/or
comprise white blood cells; and/or
comprise T cells; and/or
comprise NK cells.

110. The composition of embodiment 108 or embodiment 109, wherein the composition comprises at least at or about $5\times10^7$ cells, $1\times10^8$ cells, $2\times10^8$ cells, $4\times10^8$ cells, $6\times10^8$, $8\times10^8$ cells or $1\times10^9$ cells.

111. The composition of any of embodiments 106-110, wherein the composition comprises a therapeutically effective number of cells for use in adoptive T cell therapy.

112. The composition of any of embodiments 106-111, wherein:
the cells are T cells; and
subsequent to transduction, the cells in the composition are not subjected to cell expansion in the presence of a stimulating agent and/or the cells are not incubated at a temperature greater than 30° C. for more than 24 hours or the composition does not contain a cytokine or the composition does not contain a stimulating agent that specifically binds to CD3 or a TCR complex.

113. A composition, comprising at least $1\times10^7$ or at least $5\times10^7$ cells T cells, at least a plurality of which are transduced with a recombinant viral vector or express a recombinant or engineered antigen receptor, wherein:
subsequent to transduction, the cells in the composition have not been subjected to cell expansion in the presence of a stimulating agent; and/or
subsequent to transduction, the cells have not been incubated at a temperature greater than 30° C. for more than 24 hours.

114. A composition, comprising at least $1\times10^7$ or at least $5\times10^7$ primary human T cells, at least a plurality of which are transduced with a recombinant viral vector or express a recombinant or engineered antigen receptor, wherein at least 30%, 40%, 50%, 60%, 70%, 80%, or 90% of the T cells in the composition comprise high expression of CD69 and/or TGF-beta-II.

115. The composition of embodiment 114, wherein said at least 30%, 40%, 50%, 60%, 70%, 80%, or 90% of the T cells in the composition comprise no surface expression of CD62L and/or comprise high expression of CD25, ICAM, GM-CSF, IL-8 and/or IL-2.

116. The composition of any of embodiments 113-115, wherein said composition comprises at least $1\times10^8$ cells, $2\times10^8$ cells, $4\times10^8$ cells, $6\times10^8$, $8\times10^8$ cells or $1\times10^9$ cells.

117. The composition of any of embodiments 109-116, wherein said T cells are unfractionated T cells, isolated CD8+ T cells, or isolated CD4+ T cells.

118. The composition of any of embodiments 108-117, wherein at least 2.5%, at least 5%, at least 6%, at least 8%, at least 10%, at least 20%, at least 25%, at least 30%, at least 40%, at least 50%, or at least 75% of said cells in said composition are transduced with the viral vector.

119. The composition of any of embodiments 108-118, wherein:
the viral vector encodes a recombinant receptor; and
transduced cells in the composition express the recombinant receptor.

120. The composition of embodiment 119, wherein said recombinant receptor is a recombinant antigen receptor.

121. The composition of embodiment 120, wherein said recombinant antigen receptor is a functional non-T cell receptor.

122. The composition of embodiment 121, wherein said functional non-T cell receptor is a chimeric antigen receptor (CAR).

123. The composition of any of embodiments 119-122, wherein said recombinant receptor is a chimeric receptor comprising an extracellular portion that specifically binds to a ligand and an intracellular signaling portion containing an activating domain and a costimulatory domain.

124. The composition of embodiment 120, wherein said recombinant antigen receptor is a transgenic T cell receptor (TCR).

125. The composition of any of embodiments 110-124, wherein:
among all the cells in the composition, the average copy number of said recombinant viral vector is no more than about 10, no more than 8, no more than 6, no more than 4, or no more than about 2; or
among the cells in the composition transduced with the recombinant viral vector, the average copy number of said vector is no more than about 10, no more than 8, no more than 6, no more than 4, or no more than about 2.

126. The composition of any of embodiments 110-125, comprising a pharmaceutically acceptable excipient.

127. An article of manufacture comprising a container or plurality of containers, the container or the plurality of containers collectively containing a composition according to any of embodiments 113-126.

128. The article of manufacture of embodiment 127, wherein the container or plurality of containers comprises two or more or three or more bags and the composition further comprises a pharmaceutically acceptable excipient.

129. A method of treatment, the method comprising administering to a subject having a disease or condition the composition of any of embodiments 110-126.

130. The method of embodiment 129, wherein the transduced T cells in the composition exhibit increased or longer expansion and/or persistence in the subject than transduced T cells in a composition in which, subsequent to transduction, the cells in the composition have been subjected to cell expansion in the presence of a stimulating agent and/or the cells have been incubated at a temperature greater than 30° C. for more than 24 hours.

131. The method of embodiment 129 or embodiment 130, wherein the recombinant receptor, chimeric antigen receptor or transgenic TCR specifically binds to an antigen associated with the disease or condition.

132. The method of any of embodiments 129-131, wherein the disease or condition is a cancer, and autoimmune disease or disorder, or an infectious disease.

133. A composition, comprising:
at least $1\times10^7$ cells; and
at least at or about 1 infectious unit (IU) per cell of viral particles comprising a recombinant viral vector.

134. The composition of embodiment 133, wherein:
said cells comprise at least or about $50\times10^6$ cells; $100\times10^6$ cells; or $200\times10^6$ cells; and/or
said viral particles are present in the composition in an amount that is at least 1.6 IU/cell, 1.8 IU/cell, 2.0 IU/cell, 2.4 IU/cell, 2.8 IU/cell, 3.2 IU/cell, 3.6 IU/cell, 4.0 IU/cell, 5.0 IU/cell, 6.0 IU/cell, 7.0 IU/cell, 8.0 IU/cell, 9.0 IU/cell or 10.0 IU/cell.

135. The composition of embodiment 133 or embodiment 134, wherein the liquid volume of the composition is less than or equal to 220 mL, less than or equal to 200 mL, less than or equal to 100 mL, less than or equal to 50 mL or less than or equal to 20 mL.

136. The composition of any of embodiments 133-135, wherein said cells are primary cells.

137. The composition of any of embodiments 133-136, wherein said cells are human cells.

138. The composition of any of embodiments 133-137, wherein:
said cells comprise suspension cells;
said cells comprise white blood cells; and/or
said cells comprise T cells or NK cells.

139. The composition of embodiment 138, wherein said cells are T cells and the T cells are unfractionated T cells, isolated CD8+ T cells, or isolated CD4+ T cells.

140. The composition of any of embodiments 133-139, wherein the viral vector encodes a recombinant receptor.

141. The composition of embodiment 140, wherein said recombinant receptor is a recombinant antigen receptor.

142. The composition of embodiment 141, wherein said recombinant antigen receptor is a functional non-T cell receptor.

143. The composition of embodiment 142, wherein said functional non-T cell receptor is a chimeric antigen receptor (CAR).

144. The composition of any of embodiments 140-143, wherein said recombinant receptor is a chimeric receptor comprising an extracellular portion that specifically binds to a ligand and an intracellular signaling portion containing an activating domain and a costimulatory domain.

145. The composition of embodiment 141, wherein said recombinant antigen receptor is a transgenic T cell receptor (TCR).

146. A centrifugal chamber rotatable around an axis of rotation, said chamber comprising an internal cavity comprising the composition of any of embodiments 110-126.

147. A centrifugal chamber rotatable around an axis of rotation, said chamber comprising an internal cavity comprising: (a) a composition containing at least $5 \times 10^7$ primary T cells transduced with a recombinant viral vector and/or (b) a composition containing at least $5 \times 10^7$ primary T cells and viral particles containing a recombinant viral vector.

148. The centrifugal chamber of embodiment 146 or 147, said chamber further comprising an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity.

149. The centrifugal chamber of embodiment 147 or 148, wherein said composition in said cavity comprises at least $1 \times 10^8$ cells, $2 \times 10^8$ cells, $4 \times 10^8$ cells, $6 \times 10^8$, $8 \times 10^8$ cells or $1 \times 10^9$ of the cells.

150. The centrifugal chamber of embodiment 147 or embodiment 148, wherein said T cells are unfractionated T cells, isolated CD8+ T cells, or isolated CD4+ T cells.

151. The centrifugal chamber of any of embodiments 147-150, wherein at least 2.5%, at least 5%, at least 6%, at least 8%, at least 10%, at least 20%, at least 25%, at least 30%, at least 40%, at least 50%, or at least 75% of said cells in said composition are transduced with a viral vector.

152. The centrifugal chamber of any of embodiments 147-151, wherein:
the viral vector encodes a recombinant receptor; and
cells in the composition express the recombinant receptor.

153. The centrifugal chamber of embodiment 151, wherein said recombinant receptor is a recombinant antigen receptor.

154. The centrifugal chamber of embodiment 153, wherein said recombinant antigen receptor is a functional non-T cell receptor.

155. The centrifugal chamber of embodiment 154, wherein said functional non-T cell receptor is a chimeric antigen receptor (CAR).

156. The centrifugal chamber of any of embodiments 151-155, wherein said recombinant receptor is a chimeric receptor comprising an extracellular portion that specifically binds to a ligand and an intracellular signaling portion containing an activating domain and a costimulatory domain.

157. The centrifugal chamber of embodiment 153, wherein said recombinant antigen receptor is a transgenic T cell receptor (TCR).

158. The centrifugal chamber of any of embodiments 147-157, wherein:
among all the cells in the composition, the average copy number of said recombinant viral vector is no more than about 10, no more than 8, no more than 6, no more than 4, or no more than 2; or
among the cells in the composition transduced with the recombinant viral vector, the average copy number of said vector is no more than about 10, no more than 8, no more than 6, no more than 4, or no more than about 2.

159. A centrifugal chamber rotatable around an axis of rotation, said chamber comprising an internal cavity comprising the composition of any of embodiments 133-145.

160. The centrifugal chamber of embodiment 159, further comprising a volume of gas up to the maximum volume of the internal cavity of the chamber.

161. The centrifugal chamber of embodiment 160, wherein said gas is air.

162. The centrifugal chamber of any of embodiments 146-161, said chamber being rotatable around an axis of rotation and comprising an end wall, a substantially rigid side wall extending from said end wall, and at least one opening, wherein at least a portion of said side wall surrounds said internal cavity and said at least one opening is capable of permitting intake of liquid into said internal cavity and expression of liquid from said cavity.

163. The centrifugal chamber of any of embodiments 146-162, wherein said side wall is curvilinear.

164. The centrifugal chamber of embodiment 163, wherein said side wall is generally cylindrical.

165. The centrifugal chamber of any of embodiments 162-164, wherein
said at least one opening comprises an inlet and an outlet, respectively capable of permitting said intake and expression; or
said at least one opening comprises a single inlet/outlet, capable of permitting said intake and said expression.

166. The centrifugal chamber of any of embodiments 162-165, wherein said at least one opening is coaxial with the chamber and is located in the end wall.

167. The centrifugal chamber of any of embodiments 162-166, wherein said centrifugal chamber further comprises a movable member and said internal cavity is a cavity of variable volume defined by said end wall, said substantially rigid side wall, and said movable member, said movable member being capable of moving within the chamber to vary the internal volume of the cavity.

168. The centrifugal chamber of embodiment 167, wherein:
the movable member is a piston; and/or
the movable member is capable of axially moving within the chamber to vary the internal volume of the cavity.

169. The centrifugal chamber of any of embodiments 162-168, wherein:
the internal surface area of said cavity is at least at or about $1 \times 10^9$ μm$^2$;
the internal surface area of said cavity is at least at or about $1 \times 10^{10}$ μm$^2$;
the length of said rigid wall in the direction extending from said end wall is at least about 5 cm;
the length of said rigid wall in the direction extending from said end wall is at least about 8 cm; and/or
the cavity comprises a radius of at least about 2 cm at at least one cross-section.

170. The centrifugal chamber of any of embodiments 159-169, wherein the liquid volume of said composition present in said cavity is between or between about 0.5 mL per square inch of the internal surface area of the cavity (mL/sq.in) and 5 mL/sq.in, 0.5 mL/sq.in. and 2.5 mL/sq.in., 0.5 mL/sq.in. and 1 mL/sq.in., 1 mL/sq.in. and 5 mL/sq.in., 1 mL/sq.in. and 2.5 mL/sq.in. or 2.5 mL/sq.in. and 5 mL/sq.in.

171. The centrifugal chamber of any of embodiments 159-169, wherein the liquid volume of said composition present in said cavity is at least 0.5 mL/sq.in., 1 mL/sq.in., 2.5 mL/sq.in., or 5 mL/sq.in.

172. A closed system, comprising the centrifugal chamber of any of embodiments 147-158 and 162-171.

173. The closed system of embodiment 172, further comprising a multi-way manifold operably connected to one or a plurality of containers.

174. The closed system, comprising the centrifugal chamber of any of embodiments 159-171.

175. The closed system of embodiment 174, further comprising a sterile filter.

176. The closed system of any of embodiments 172-175, wherein the centrifugal chamber is capable of rotation at a speed up to 8000 g, wherein the centrifugal chamber is capable of withstanding a force of up to 500 g, 600 g, 1000 g, 1100 g, 1200 g, 1400 g, 1500 g, 1600 g, 2000 g, 2500 g, 3000 g or 3200 g, without substantially yielding, bending, or breaking or otherwise resulting in damage of the chamber and/or while substantially holding a generally cylindrical shape under such force.

177. The method of embodiment 49, wherein at least at or about 30, 40, 50, 60, 70, 80, or 80% of the T cells in the output composition comprise high expression of CD69 and/or TGF-beta-II.

178. The method of embodiment 177, wherein said at least 30, 40, 50, 60, 70, 80, or 80% of the T cells in the composition comprise no surface expression of CD62L and/or comprise high expression of CD25, ICAM, GM-CSF, IL-8 and/or IL-2.

179. A method comprising
washing primary human cells; and
incubating said cells with a selection reagent under agitation conditions whereby at least a plurality of the human cells are specifically bound by the selection reagents,
wherein said washing and incubating are carried out within a closed, sterile system and at least in part in an internal cavity of a centrifugal chamber integral to the closed, sterile system.

180. The method of embodiment 179, wherein the method steps are carried out in an automated fashion based on input from a user that the method should be initiated, resulting in completion of the method steps.

181. The method of embodiment 105, 179 or 180, wherein the incubation under mixing conditions comprises effecting rotation of the chamber for at least a portion thereof.

182. The method of embodiment 181, wherein the effecting rotation for at least a portion thereof comprises effecting rotation at a plurality of periods during the incubation, said plurality of periods being separated by one or more periods of rest, at which the chamber is not rotated.

183. The method of embodiment 182, wherein one or more or all of the plurality of periods of effecting rotation is for a time that is or is about 1, 2, 3, 4, 5, 6, 7, 8, 9, or 10 seconds, such as 1 or 2 seconds and/or one or more or all of the one or more periods of rest is for a time that is or is about 3, 4, 5, 6, 7, 8, 9, or 10 or 15 seconds, such as 4, 5, 6, or 7 seconds.

184 The method of any of embodiments 105 or 179-183, wherein the incubation under mixing conditions is carried out for at least or approximately 10, 15, 20, 30, or 45 minutes, such as at or about 30 minutes.

EXAMPLES

The following examples are included for illustrative purposes only and are not intended to limit the scope of the invention.

Example 1: Viral Transduction of Primary Human T Cells in a Centrifugal Chamber

This example demonstrates transduction of isolated primary human T cells with a recombinant viral vector encoding a chimeric antigen receptor (CAR), with transduction initiated under centrifugal force in a substantially rigid cylindrical centrifugal chamber, according to an embodiment provided herein. T cells were isolated via positive selection from a human apheresis product sample.

The resulting cells were activated using an anti-CD3/CD28 reagent. For initiation of transduction, the cells were incubated with a viral particle containing a viral vector genome encoding an anti-CD19 CAR under various conditions following activation.

Under one set of conditions ("Sepax"), transduction was initiated by incubating the cells in a cavity of a centrifuge chamber (Biosafe SA, A200), under centrifugation in a Sepax® 2 processing unit (Biosafe SA). A 50 mL liquid composition containing $50 \times 10^6$ of the isolated cells was combined in a 300 mL transfer pack with 50 mL liquid stock containing the viral vector particles. Using the Sepax® system to move the piston of the chamber, the composition was pulled into the cavity of the centrifuge chamber. 100 mL air also was pulled in, thereby increasing the volume of the cavity to 200 mL and resulting in a decrease in the ratio of the volume of liquid in the cavity to the internal surface area of the cavity. The chamber was spun by ramping up to a speed of at approximately 4600 rpm on the Sepax® 2 unit, corresponding to a relative g force (relative centrifugal force (RCF)) at the internal side wall of the processing cavity of the chamber of approximately 600. The duration of the spin at this speed was 60 minutes.

For another set of conditions ("VueLife"), a composition containing $25 \times 10^6$ cells and the same stock of viral vector particles at a 1:1 volumetric ratio were incubated in 50 mL in a centrifuge bag, in a CI-50 centrifuge adapter, and spun at an approximate relative centrifugal force (RCF) on the cells of approximately 1000 g for 60 minutes. A bag with a smaller volume compared to the centrifuge chamber was used in order to permit centrifugation at a relative centrifugal force on the cell of 1000 g. Controls included an "untransduced" sample (same cell concentration incubated for the same time in a 24-well plate without virus without centrifugation and a "no-spin" control ("0xg") sample (same cell/virus concentration incubated for the same time in the same plate without centrifugation). Under each set of conditions, a polycation was included. Following spin (or comparable "no-spin" incubation), the compositions were incubated for 24 hours at 37 degrees C. to complete transduction.

Figure 1B:
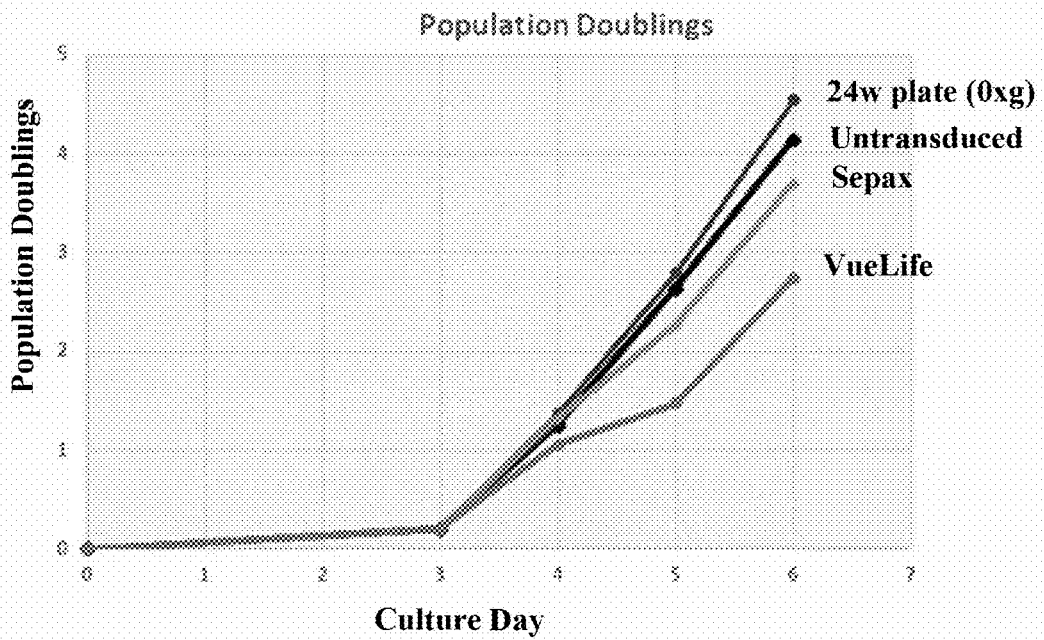
FIG. 1B shows population doublings over a six-day period during the transduction study described in Example 1.

The cells were expanded and transduction efficiency for each of the respective conditions was calculated on Day 6 post-isolation as percentage of $CD3^+$ T Cells with surface expression of the encoded CAR (as detected by flow cytometry using an antibody specific for the CAR). The results are shown in FIG. 1A. As shown, greater transduction efficiency was observed following the initiation of transduction by incubating cells in the cavity of the centrifuge chamber under rotation, as compared to in the centrifuge bag (Vue- Life®) and controls. FIG. 1B shows cell expansion (as indicated by number of population doublings) over the six-day period.

Example 2: Transduction of Primary Human T Cells in a Centrifugal Chamber at Different Ratios of Liquid Volume to Surface Area Transduction efficiency following initiation of transduction in the centrifuge chamber was assessed under various conditions, using the same number of cells and infectious units of virus, and different ratios of liquid volume to internal surface area of the chamber's cavity. Cells were generally prepared and stimulated as described in Example 1. All transduction initiation conditions used an IU:cell ratio of 2:1 and a total number of $100 \times 10^6$ cells.

For a first sample ("5.1 mL/sq.in.," referring to the 5.1:1 mL of liquid per square inch of internal cavity surface used in this condition), $100 \times 10^6$ cells, in a liquid volume of 100 mL, were combined with 100 mL of a liquid composition containing the viral vector particles. For a second sample ("2.5 mL/sq.in.," referring to 2.5 mL of liquid per square inch of cavity surface used in this condition), 50 mL of a liquid composition with the same number of cells was combined with 50 mL of a liquid composition containing the viral vector particles. In each case, a polycation was included for a final concentration during centrifugation of 10 µg/mL. The respective liquid compositions (and for the second sample, 100 mL of air) were drawn into and incubated in the liquid-holding cavity of the chamber. In each case, the chamber was spun (by ramping up) in the Sepax® 2 processing unit at an rpm of approximately 4600, corresponding to an RCF at the internal cavity side wall of approximately 600 g for 60 minutes. The samples then were incubated for an additional 24 hours at 37 degrees, for completion of transduction.

The cells were expanded and transduction efficiency calculated on Day 6 post-isolation, by determining the percentage of $CD3^+$ T Cells with surface expression of the CAR, detected as described above. The results are shown in FIG. 2. As shown, for initiation of transduction in the centrifugal chamber using the same number of cells and infectious units of virus, a greater transduction efficiency was observed when using a lower ratio of liquid volume of the composition in the cavity to the internal surface area of the cavity.

Example 3: Transduction of Primary Human T Cells in a Centrifugal Chamber

Another study compared transduction efficiency under various conditions, including transduction in a centrifugal chamber according to embodiments of the provided methods, using various ratios of liquid volume to cavity surface area. Human T cells were isolated from an apheresis product and stimulated as described above.

Following the stimulation, $80 \times 10^6$ cells were incubated under varying conditions, including for transduction with a viral vector encoding a CAR. A polycation was included in all samples.

For conditions under which transduction was initiated in the centrifuge chamber, $80 \times 10^6$ cells were incubated with virus containing the vector in the cavity of the chamber, at a ratio of 2 IU virus per cell. The incubation was carried out while centrifuging the chamber using the Sepax® 2 Processing system at an RCF at the internal side wall of the cavity of approximately 600 g for 60 minutes. Under one set of conditions ("Sepax (0.1 IU/cell/mL)," with 0.5 mL liquid volume per square inch of internal cavity surface), for centrifugation, the cells and virus were pulled into the cavity of the chamber in a total liquid volume of 20 mL; 180 mL of air also was pulled into the cavity. Under another set of conditions ("Sepax (0.01 IU/cell/mL)," with 5.1 mL liquid volume per square inch of internal cavity surface), the same number of cells and infectious units of virus were pulled in in a 200 mL liquid volume.

Under separate conditions, "1000 g in plate," transduction of cells was initiated in the presence of virus (2 IU/cell) in a 24-well plate, with centrifugation at an RCF on the cells of approximately 1000 g for 60 minutes. An "untransduced" negative control (incubation in a 24-well plate without virus or centrifugation) and a "no spin" control (incubation with virus at a ratio of 2 infectious units (IU) per cell without centrifugation in the same 24-well plate) also were used. Cells were incubated for 24 hours at 37 degrees C. to complete transduction.

Figure 3:
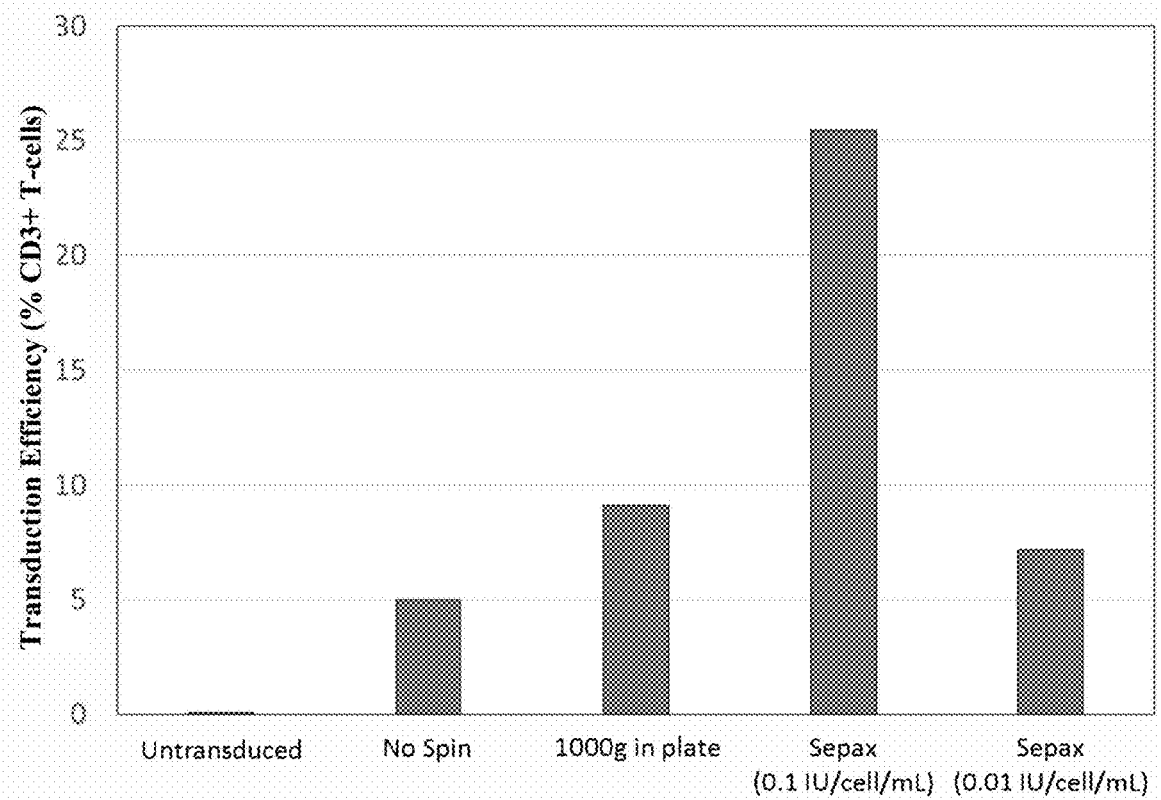
FIG. 3 shows transduction efficiency calculated as percentage of CD3$^+$ T Cells with surface expression of a CAR encoded by a viral vector following incubation under various conditions as described in Example 3.

Cells were expanded and transduction efficiency for each sample calculated as percent of $CD3^+$ cells expressing the CAR on their surface, as described in Examples 1 and 2. The results are shown in FIG. 3. As shown, transduction was observed following initiation of transduction under rotation in the centrifuge chamber and in the 24-well plate as compared to the control conditions. For transduction initiation in the centrifuge chamber, greater transduction efficiency was observed with a lower ratio of liquid volume to internal surface area of the chamber cavity.

Figure 4:
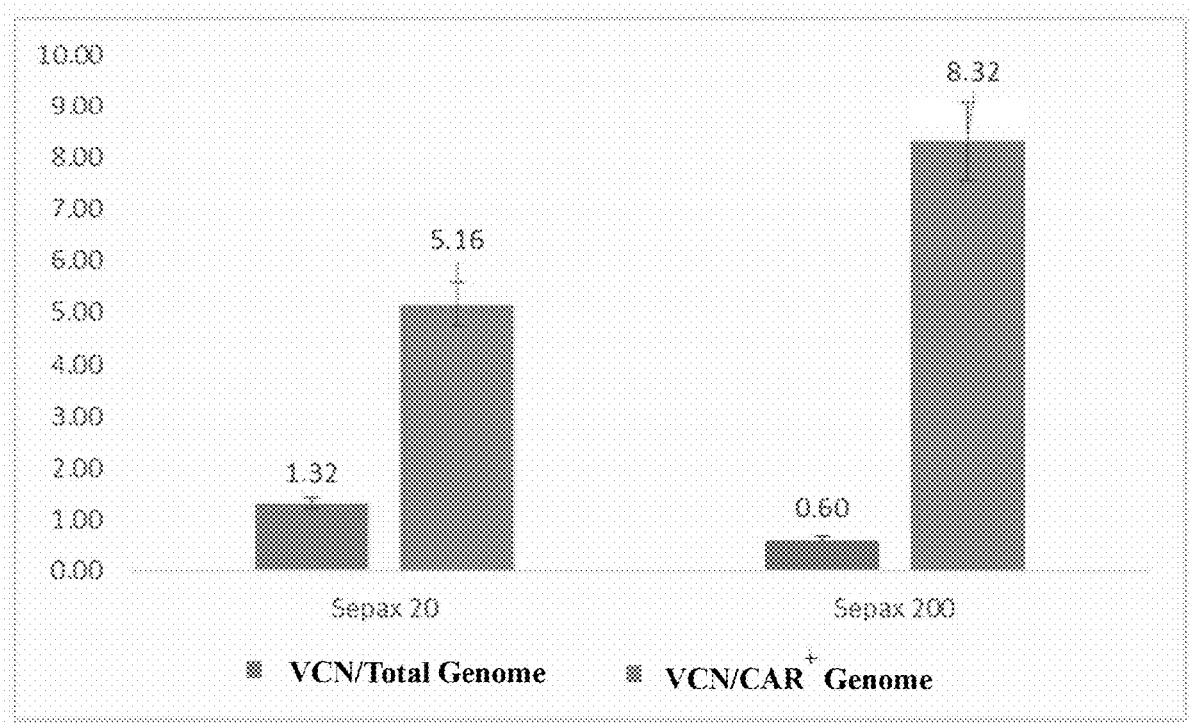
FIG. 4 shows mean vector copy number (VCN) of a viral vector in indicated cell populations following transduction under various conditions as described in Example 4.

Example 4: Assessment of Vector Copy Number (VCN) Following Transduction in a Centrifugal Chamber Copy number of the integrated viral vector (VCN) was assessed following transduction initiated under certain conditions in the study described in Example 3. VCN per cell was determined for the SGF-derived retroviral vector by real-time quantitative PCR (RT-qPCR). Mean VCN was determined by qPCR specific for viral genome among all cells in the composition following transduction ("VCN/cell"), and separately among the transduced cells (cells expressing the transgene) alone ("VCN/$CAR^+$"). The results are presented in FIG. 4. In the graph shown in FIG. 4, the label "Sepax 20" refers to a 20 mL liquid volume used in the chamber cavity during transduction initiation; the results so-labeled are from the same study and condition labeled as "Sepax (0.1 IU/cell/mL)" in Example 3 (for which transduction efficiency was determined to be 25%). Similarly, the label "Sepax 200" refers to a 200 mL liquid volume used in the chamber cavity during transduction initiation; the results so-labeled are from the same study and conditions labeled as "Sepax (0.01 IU/cell/mL)" in Example 3 (for which the transduction efficiency was determined to be 7%). As shown, when transduction was initiated by initiating transduction of cells in the cylindrical, substantially rigid centrifuge chamber under rotation, increased transduction efficiency was not associated with increased vector copy number. In this study, the conditions producing increased transduction efficiency also produced decreased mean vector copy number per cell.

Example 5: Transduction Using a Sepax® 2 Processing System

In an exemplary process, T cells are transduced with a viral vector particle in an automated fashion in a centrifugal chamber integral to a single-use system and the Sepax® 2 processing system (Biosafe SA). The chamber is integral to a sterile, disposable closed system, which is a single-use processing kit sold by Biosafe SA for use in regenerative medicine. The kit is configured to include a series of tubing lines connecting the chamber to a series of containers, with a general configuration shown in FIG. 5 and/or FIG. 7. The chamber (1) includes an end wall (13) including an inlet/outlet opening (6), a rigid side wall (14), and a piston (2), which collectively define an internal cavity (7) of the chamber. The system is configured to include various containers labeled: Output Bag, Waste Bag, Input Bag, and two diluent bags (Diluent Bag 1 and Diluent Bag 2), and various connectors, including stopcocks, and valves. Clamps (5) are included for blocking flow between different portions of the system via the tubing lines. In some embodiments, the system includes a male luer lock sterile filter (15) with female luer lock cap (16), through which gas, e.g., air, may be drawn in a sterile manner, when the cap is released/removed. The system is placed in association with the Sepax® 2 processing unit, including a centrifuge and cabinet for housing components.

In the exemplary process, the Input Bag contains a composition containing the cells to be transduced. Diluent Bag 1 contains viral vector particles, polycation, and medium. In some embodiments, air is included in the bag with the vector particles. For example, in an alternative embodiment, a container with air and/or additional medium may be connected at this position instead of and/or in addition to the virus composition.

A user indicates to the processing unit via a user interface that a new program is to be run and inputs various parameters into the system, including an Initial Volume (between 20-900 mL), a Final Volume (between 20-220 mL), an Intermediate Volume (between 10-100 mL), a Dilution Volume (between 50-220 mL), a g-force (between 100-1600 or between 200-3200 g) (RCF at the internal side wall of the processing cavity of the chamber)), and a Sedimentation Time (between 120 and 3600 seconds). The user indicates to the system that the process should be initiated, inputs identification information for the subject from which cells are derived, and indicates to the system that input is complete, which prompts the system to carry out a test of the closed system kit.

With all respective stopcock valves in the closed position, clamps blocking movement of fluid between the tubing lines and Diluent Bag 1, Waste Bag, Input Bag, and Output Bag (for collection of the product containing the cells), respectively, are opened and an automated program initiated by communication with the system by the user.

In response, the system causes, in an automated fashion, movement of liquid and/or gas between the various components of the closed system by causing opening and closing of the valves and movement of the piston to vary the volume of the cavity. It causes repositioning of a stopcock to permit flow between the Input Bag and the internal cavity of the chamber, via the inlet/outlet opening and lowering of the piston within the centrifugal chamber, thereby increasing the volume of the cavity and drawing a volume (the user-defined Initial Volume) of the composition of cells and viral vector particles from the Input bag to the processing cavity, via an inlet/outlet in the end wall of the chamber.

The system prompts the centrifuge to spin the chamber for 120 seconds at 500 g, prompts purging of 20 mL volume from the cavity into the Input Bag to rinse it, and drawing of the volume back into the cavity. The system prompts the centrifuge to spin the chamber for 180 seconds at 500 g, causing sedimentation. The system repositions the stopcocks to permit flow of fluid and/or gas between the cavity and the Waste Bag and effects extraction of fluid from the cavity into the Waste Bag, leaving the user-defined Intermediate Volume in the cavity.

The system causes rotation of the stopcock to block movement of fluid between the tubing and the waste bag. The system causes intake of viral vector particle-containing liquid composition and, if applicable, air (collectively, at the user-defined Diluent Volume) from Diluent Bag 1 to the cavity of the chamber. These steps collectively effect intake of an input composition containing cells to be transduced and viral vector particles and in some cases, air, into the cavity. In some embodiments, the total volume of the cavity is 200 mL, for example, including 200 mL liquid volume or including less than 200 mL liquid volume and the remainder of the cavity volume including air.

Centrifugation of the chamber is carried out for the user-defined Sedimentation Time at the user-defined g-force, resulting in initiation of transduction of cells in the input composition with viral vector particles. In an alternative embodiment, a volume of air and/or medium is pulled into the cavity from another bag at the position of Diluent Bag 1 and 2, prior to centrifugation. In an alternative embodiment, air is drawn in prior to centrifugation through the luer lock filter (15), e.g., by the user opening the clamp (5) blocking movement of fluid between the filter (15) and tubing lines and the cavity (7) and releasing the female cap (16), allowing air remaining in the chamber to pass in through the filter from the environment. In some embodiments, the movement of air is automated by the system, for example, based on an additional user-defined air input volume inputted into the system and the user indicating to the system that air may be taken in at the defined air volume. In some embodiments, air, if present, is released through the tubing line and uncapped filter (15) by a similar process following centrifugation.

When prompted by the system, the user closes the clamp blocking movement of fluid between Diluent Bag 1 and the tubing lines and opens the clamp blocking movement of fluid between Diluent Bag 2 and the tubing lines. The system causes movement of fluid from Diluent Bag 2 to the processing cavity by opening of the appropriate stopcock valve and movement of the piston to draw into the cavity a volume of fluid from Diluent Bag 2 equal to the amount required to result in a total liquid volume in the chamber equal to the user-defined Final Volume. The system then causes mixture of the fluid in the cavity for 60 seconds and then transfer of the fluid in the internal cavity to the Output Bag, which thereby contains an output composition with cells to which viral particles have bound and/or infected with the viral vector. These cells then are generally incubated for completion of transduction, for example, at 37 degrees C., for example, for 24 hours.

Example 6: Assessment of Cell Growth and Viability at Different Centrifugal Forces The effect of centrifugal force on cells during the centrifugation used to initiate transduction of cells in a chamber according to certain provided embodiments was assessed. Cell expansion and cell viability were assessed upon exposure to different centrifugal forces.

T cells were isolated and stimulated essentially as described in Example 1. At day 4, various, each individually containing the cells, were pulled into a cavity of a centrifuge chamber in a Sepax® 2 processing unit (Biosafe SA) and subjected to centrifugation at various centrifugal forces.

Specifically, samples were spun for 60 minutes in a chamber (A-200F) integral to a single-use kit using the Sepax® 2 processing system at approximately 4600 rpm, approximately 6000 rpm, and approximately 7400 rpm, respectively), which achieved an RCF at the internal surface of the side wall of the cavity of approximately 600 g 1000 g, and 1600 g, respectively. As a control, a sample of the cells was separately pulled into the centrifuge cavity, but not spun (0 g condition). In each case, after the spin (or incubation with no spin), the cells were incubated at 37° C., 5% $CO_2$, through day 10. At various points throughout the process, cell expansion (population doublings as compared with cell number at day 0) and viability were monitored. Specifically, these measurements were taken at days 0, 3, 4, 5, 6, 7, and 10. The results are shown in FIG. 6.

Figure 6A:
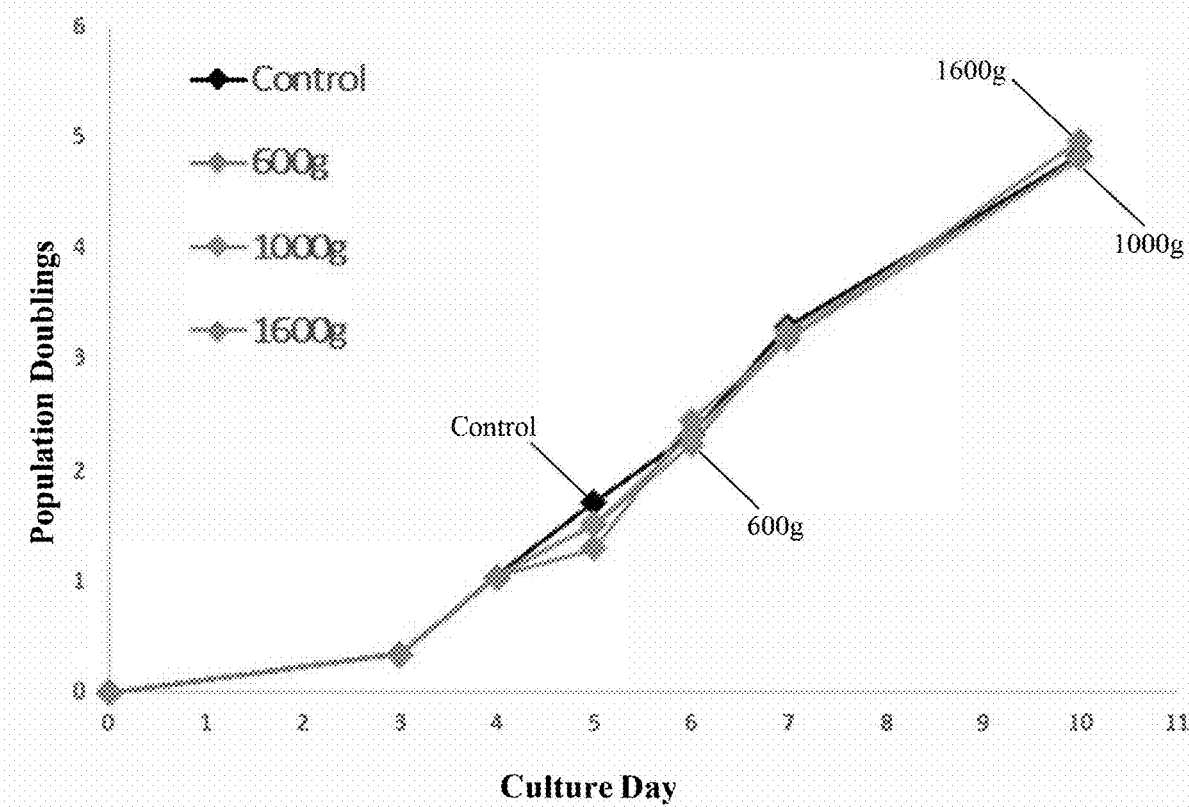
FIG. 6A shows population doublings over a ten-day period during the study described in Example 6.
Figure 6B:
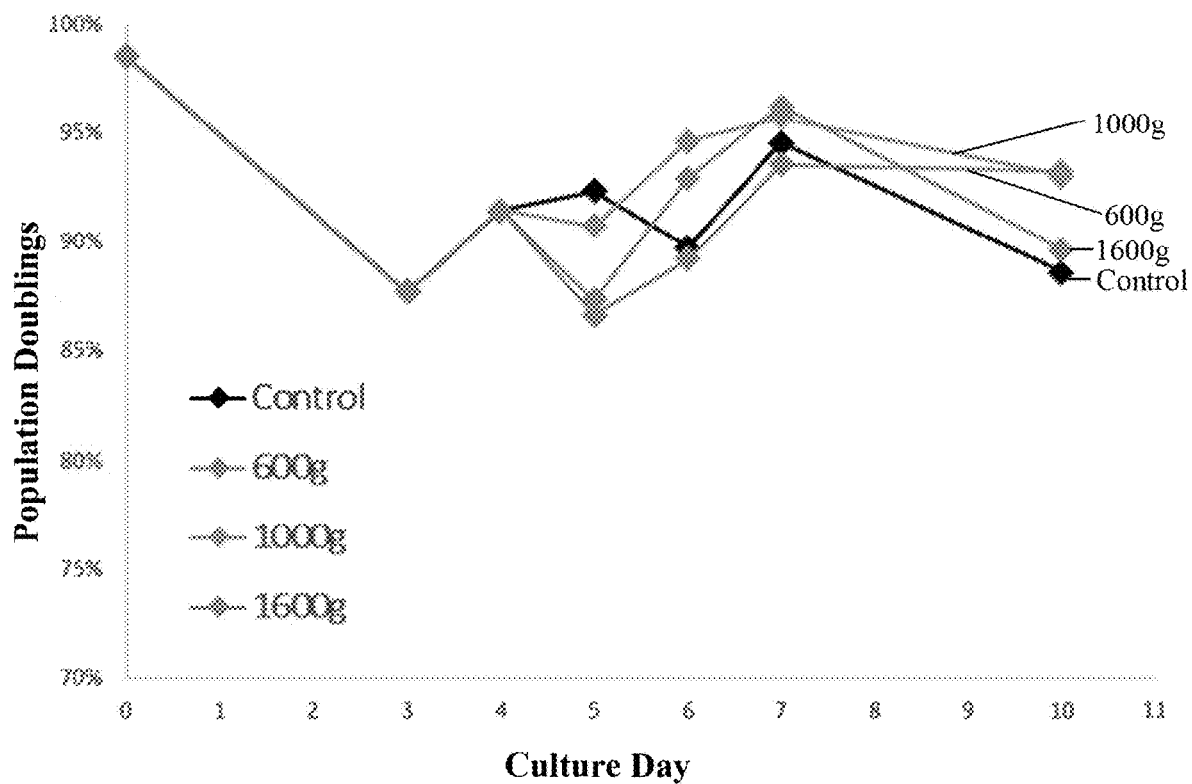
FIG. 6B shows percent viability of cells over a ten-day period during the study described in Example 6.

As shown in FIG. 6A and FIG. 6B, respectively, centrifugation at the various speeds was observed to have no substantial effect on cell expansion ("population doublings") or viability over the 10 days. The results demonstrate that the T cells could tolerate centrifugation at relative centrifugal forces of at least up to or about 1600 g, as measured at the side wall of the cavity of the chamber, corresponding to approximately the same average force on the cells at the cell surface:liquid interface, under conditions used for transduction initiation in embodiments provided herein, without detectable substantial changes in expansion or viability.

Example 7: Transduction Process Step Using Transduction Initiation in Generally Cylindrical Centrifugal Chamber This example describes the general parameters of a transduction process step that was used in the studies described in Examples 8-10. Transduction of cells with a recombinant viral vector encoding a chimeric antigen receptor (CAR) was initiated in a centrifugal chamber according to provided embodiments.

$CD4^+/CD8^+$ T cells were isolated via positive selection from a human apheresis product sample. The isolated cells were cryopreserved and thawed at 37° C. The thawed cells were activated using CD3/CD28 beads in the presence IL-2 (100 IU/mL) for 72 hours at 37° C. prior to initiation of transduction. In some cases, various aspects of the apheresis preparation, isolation, and/or activation steps also were carried out in the cavity of a centrifugal chamber according to provided embodiments, in association with the Sepax® 2 system, e.g., as described in Example 11.

In preparation for transduction, a centrifugal processing chamber (1) (A-200F), integral to a sterile, single-use disposable kit sold by Biosafe SA for regenerative medicine use, essentially as depicted in FIG. 7, was placed in association with a Sepax® 2 processing unit, which thus could provide to the chamber centrifugal force and axial displacement (permitting control of the dimensions of the internal cavity). (U.S. Pat. No. 6,733,433).

To initiate transduction, the following steps were carried out.

To generate a composition containing viral vector particles for sterile mixing with the activated cells in the centrifuge chamber, complete media (containing serum free hematopoietic cell medium supplemented with 5% human serum, and IL-2, and a polycation in an amount sufficient for a final concentration during transduction initiation of 10 μg/mL), viral vector particles at the indicated number or relative number of infectious units (IU) (for example, 1.8 IU/cell or 3.6 IU/cell), and, where applicable, air, were aseptically transferred to a centrifuge bag, which ultimately would be sterilely connected with the kit at a Diluent Bag position for intake as described below.

A culture bag containing the activated cells was sterilely connected to the single-use disposable kit via tubing line at the position of the "Input Bag" shown in FIG. 5 and FIG. 7. An automated "dilution" protocol was run on the Sepax® 2 processing unit. Thereby, through movement of the piston, the desired number of cells (as indicated in individual studies described, for example, $50 \times 10^6$, $100 \times 10^6$ or $200 \times 10^6$ cells) was transferred from the culture bag to a product bag at the "Output Bag" position shown in FIG. 5 and FIG. 7, by way of the chamber cavity.

To generate an input composition with both cells and virus (and where applicable, air) for intake into the chamber and transduction, the product bag containing the desired number of activated cells then was sterilely connected at the Input Bag position as shown in FIG. 5 and FIG. 7. The centrifuge bag containing the viral particles, media, and optionally air was sterilely connected at the position of Diluent Bag 1 shown in the figures. An automated Wash cycle was run on the Sepax® 2, facilitating drawing in of the composition containing the cells into the cavity of the chamber, spinning of the composition on the Sepax® 2 at an approximate RCF at the internal wall of the cavity of 500 g to pellet the cells, and removal of the appropriate volume of liquid required to achieve a desired volume, e.g., 10 mL. The contents of the centrifuge bag at the Diluent Bag 1 position, including the viral particles, media, polycation, and where applicable, air, then was drawn into the cavity of the chamber with the cells. This process thus effected a volume-reduction of the cell composition and combined the volume-reduced cells with the virus-containing composition and, where applicable, air. The resulting 200 mL volume (containing the cells, virus, and optionally, air) then was transferred into a centrifuge bag in the "Output Bag" position of the kit as shown in FIG. 5 and FIG. 7.

To initiate transduction, the centrifuge bag containing 200 mL of the virus, cells, and air where applicable then was removed and sterilely connected at the Input Bag position of the kit. A bag containing complete media was sterilely connected to the kit at a "Diluent Bag" position. A cell culture bag was sterilely connected to the system at the "Output Bag" position. The user indicated via the interface that an automated protocol should be run on the system for initiation of transduction. Specifically, the program caused transfer of the 200 mL volume containing cells, virus, and where indicated, air, via the tubing lines to the cavity of the chamber by movement of the piston. The program continued with centrifugation of the contents in the cavity of the chamber (total volume 200 mL) at the indicated force, to initiate transduction of cells with the viral vector particles. In some embodiments, a hand-held laser tachometer was used to verify revolutions per minute (rpm) at various set points on the Sepax® unit using known methods. Except where specifically indicated, the spin was carried out at the indicated speed for 1 hour (3600 s), with additional ramp-up and ramp-down time. Following the spin and when prompted by the system, the user closed the clamp permitting movement of fluid between the cavity and the Input Bag and opened the clamp blocking movement of fluid between the cavity and product bag at the Output Bag position. Upon input from the user, the program continued by effecting movement of liquid from the chamber to the output bag.

Where applicable, for expulsion of air, when prompted by the system, the user opened the clamp blocking movement of fluid between the chamber cavity and the filter, and the program caused expression of air via the filter.

A dilution program then was run on the Sepax® 2 system, with the clamp blocking movement of fluid between the diluent bag with the media and the chamber opened and the program causing movement (by opening of stopcock(s) and movement of the piston) of the appropriate amount of liquid from that bag to the chamber, mixing for 60 seconds, and then transfer of the fluid from the processing cavity to the output bag, the appropriate amount being that needed to achieve a user-defined Final Volume of 200 mL, given the presence of air during centrifugation, if any.

The culture bag in the Output Bag position thereby contained an output composition with cells containing bound viral particles and/or inoculated with the viral genome. The cells then were incubated in the bag for ~24 hours at 37 degrees C., 5% $CO_2$, for completion of transduction. During the transduction initiation and completion, viral vector particles inoculated cells and their genomes became integrated into the cellular genomes, as indicated by the various measures for transduction efficiency and copy number in the individual examples.

Example 8: Transduction Initiation in a Centrifugal Chamber with Constant Volume and Viral Particle Number and Different Cell Concentrations Compositions with various cell numbers and infectious units (IU) of viral particles, in constant liquid volume, were subjected to the transduction process described in Example 7. In each case, prior to transduction initiation, cells were collected, washed, isolated, cryopreserved, and activated as described in Example 11.

Example 8A

Transduction initiation and further culture to complete transduction were carried out as described in Example 7, with the following specifics.

Under two separate conditions in two separate studies, the transduction initiation process was carried out in a 70 mL total liquid volume (the remaining 130 mL volume of the cavity during spin containing air). The separate conditions were carried out on $200\times10^6$ cells and $100\times10^6$ cells, respectively. The same total number of units of viral vector particles containing vectors encoding anti-CD19 CAR were used, resulting in 1.8 IU/cell and 3.6 IU/cell for the two conditions, respectively. During the transduction program, the 3600 second spin was at approximately 7400 rpm, corresponding to an RCF of approximately 1600 g at the side wall of the processing cavity.

Figure 8A:
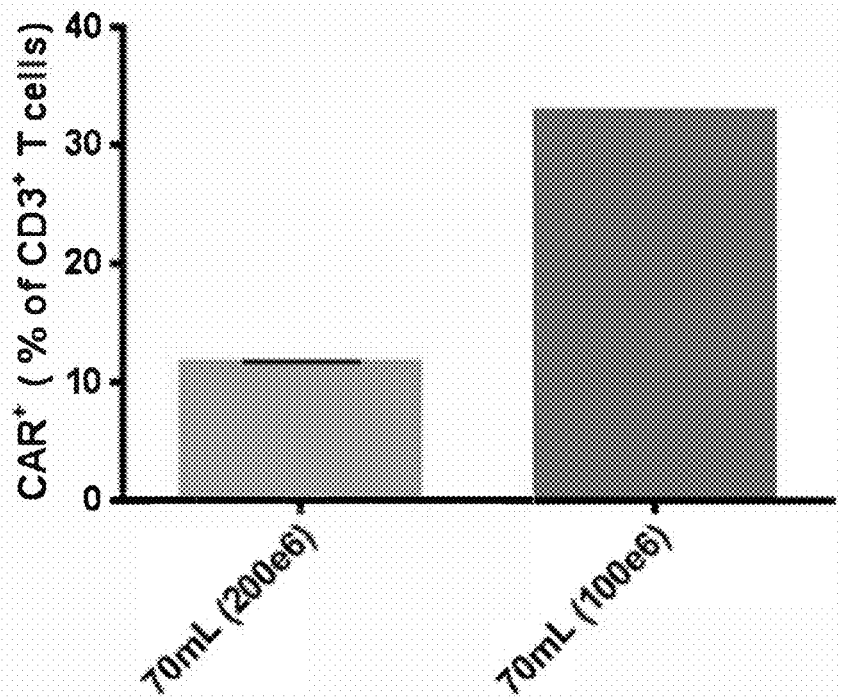
FIG. 8A shows transduction efficiency calculated as percentage of CD3$^+$ T Cells with surface expression of a CAR encoded by a viral vector following incubation under the indicated conditions as described in Example 8A.

After the ~24-hour incubation, the cells were expanded in a Bioreactor System with perfusion. Transduction efficiency for the respective compositions was calculated on Day 6 as percentage of $CD3^+$ T Cells with surface expression of the encoded CAR, detected as described in Example 1, and was compared to an untransduced population of cells as a control ("untransduced"). The results are shown in FIG. 8A. As shown, with the same total volume and total number of infectious units during incubation under rotation, a greater transduction efficiency was observed for the condition using a smaller number of $100\times10^6$ cells in the cavity during the incubation.

Example 8B

In another study, transduction initiation and further culture to complete transduction were carried out as described in Example 7, with the following specifics.

Under three separate conditions, the transduction initiation process was carried out in a 70 mL total liquid volume (the remaining 130 mL volume of the cavity during spin containing air). The separate conditions were carried out on $200\times10^6$ cells, $100\times10^6$ cells, and $50\times10^6$ cells, respectively. The same total number of units of viral vector particles containing vectors encoding anti-CD19 CAR were used, which was the number of units needed to result in 1.8 IU/cell for the condition with $200\times10^6$ cells. During the transduction program, the 3600 second spin was carried out on the Sepax® 2 system at approximately 7400 rpm, corresponding to an RCF of approximately 1600 g at the side wall of the processing cavity.

Figure 8B:
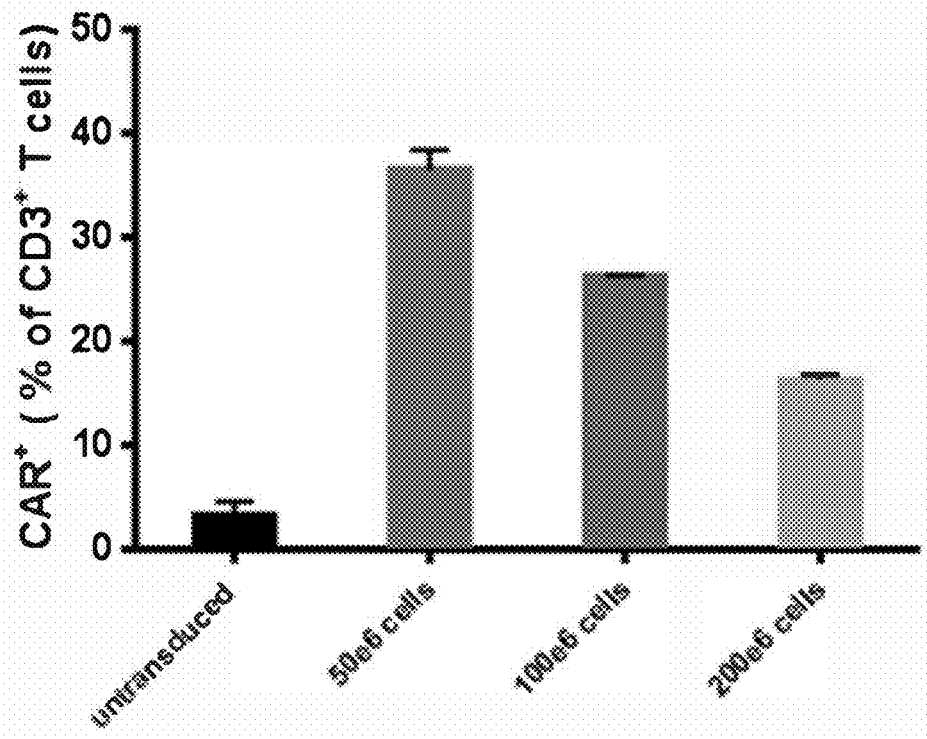
FIG. 8B shows transduction efficiency calculated as percentage of CD3$^+$ T Cells with surface expression of a CAR encoded by a viral vector following incubation under the indicated conditions as described in Example 8B.

After the ~24-hour incubation, the cells were expanded in a Bioreactor System with perfusion. Transduction efficiency for the respective compositions was calculated on Day 6 as percentage of $CD3^+$ T Cells with surface expression of the encoded CAR, detected as described in Example 1, and was compared to an untransduced population of cells as a control ("untransduced"). The results are shown in FIG. 8B. As shown, with the same total volume and total number of infectious units during incubation under rotation, a greater transduction efficiency was observed for the condition using a smaller number of $100\times10^6$ cells in the cavity during the incubation.

Figure 8C:
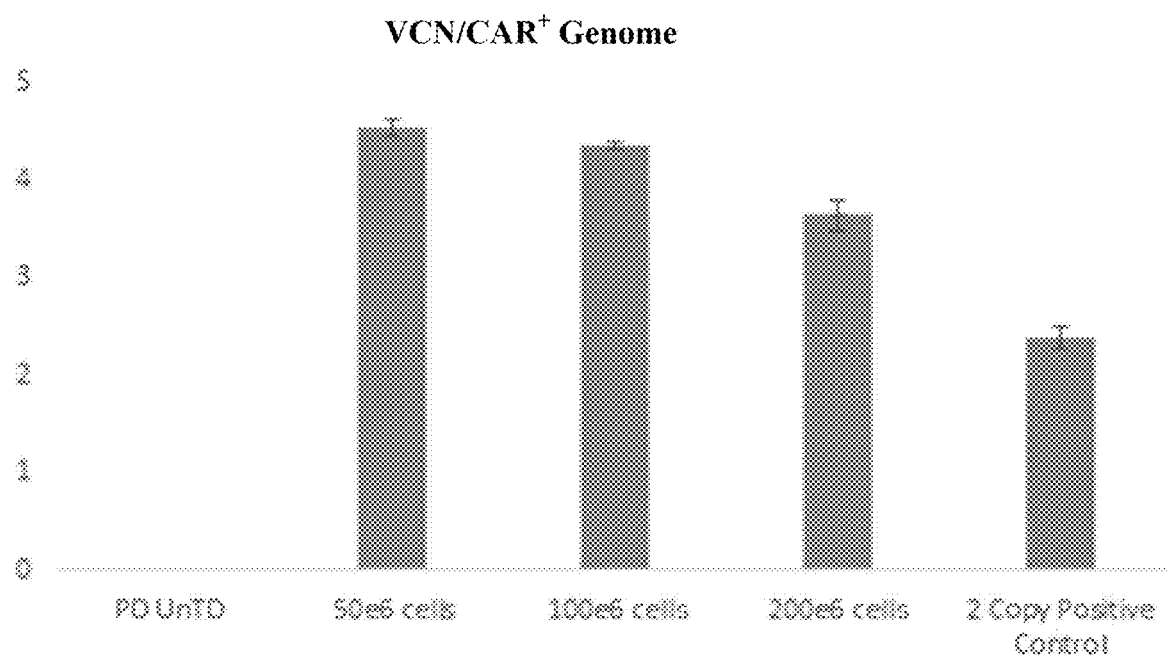
FIG. 8C shows mean vector copy number (VCN) of a viral vector in indicated cell populations following transduction under various conditions as described in Example 8B.

Vector copy number (VCN) also was assessed in transduced cells at day 6, as described in Example 4, with mean VCN determined among the transduced cells (cells containing SGF+ viral vector nucleic acid in their genome). An untransduced cell control ("PD UnTD") and positive control cells ("2 Copy Positive Control") also were assessed. The results are presented in FIG. 8C.

Example 9: Transduction Initiation in Centrifugal Chamber with Various Volumes and Units of Viral Vector Particles Compositions with increasing numbers of infectious units (IU) of viral particles and liquid volumes (with constant number ($100\times10^6$) of cells) were subjected to the transduction process described in Example 7, with the following specifics. In each case, prior to transduction initiation, cells were collected, washed, isolated, cryopreserved, and activated as described in Example 11.

In the process described in Example 7, the composition containing the viral particles, media, and air that was drawn in from the Diluent Bag position for combining with the cells via the dilution protocol, included 60, 90, and 120 mL liquid volumes, respectively, for the different conditions (with the 10 mL cell-containing composition, resulting in 70, 100, and 130 mL liquid volume, respectively, for the individual conditions), with the remaining of the 200 mL total volume pulled into the chamber for spinning being comprised of air. Each of these liquid volumes included $6\times10^6$ IU viral vector particles per mL of liquid volume, resulting in an increasing IU and IU/cell for each condition. The speed for the 3600 second spin was carried out at approximately 7400 rpm, corresponding to an RCF of approximately 1600 g at the internal wall of the cavity on the Sepax® unit. An untransduced ("mock") control also was used.

Figure 9A:
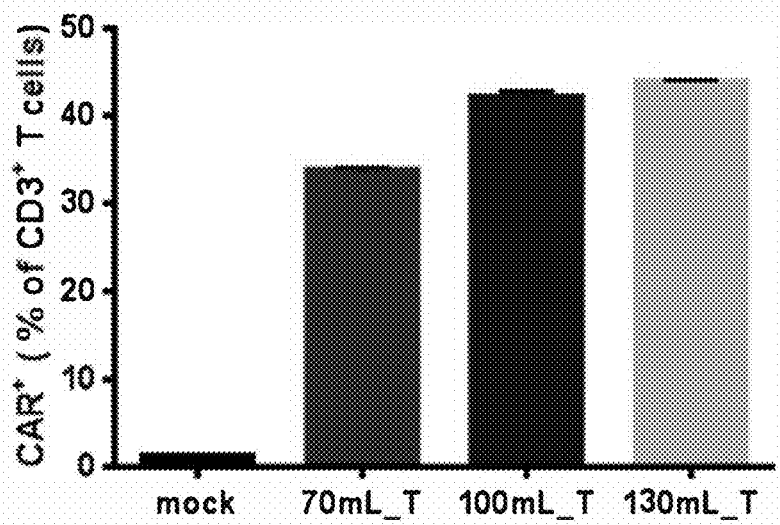
FIG. 9A shows transduction efficiency calculated as percentage of CD3$^+$ T Cells with surface expression of a CAR encoded by a viral vector following incubation under the indicated conditions as described in Example 9.

After the ~24-hour incubation, the cells were expanded in a Bioreactor System with perfusion. Transduction efficiency for the respective compositions was calculated on Day 6 as percentage of $CD3^+$ T Cells with surface expression of the encoded CAR, detected as described in Example 1. The results are shown in FIG. 9A. As shown, for the same number of cells, an increasing amount of virus with corresponding increase in volume resulted in an increased transduction efficiency in this study.

Figure 9B:
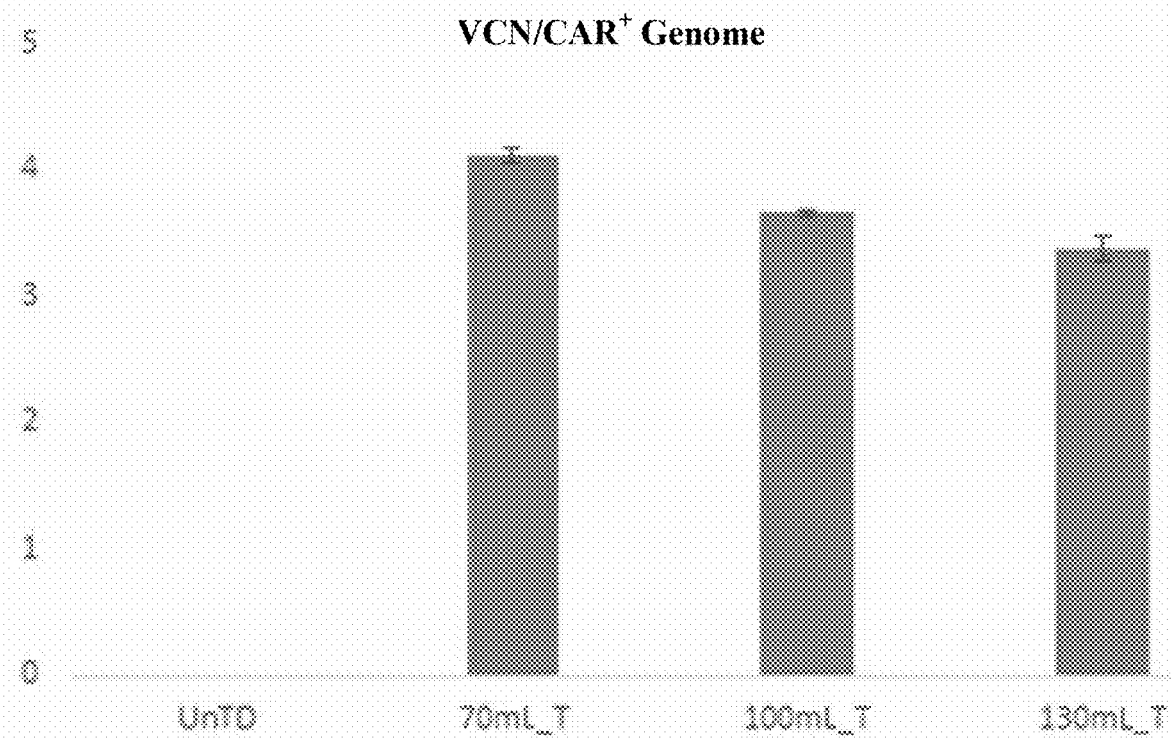
FIG. 9B shows mean vector copy number (VCN) of a viral vector in indicated cell populations following transduction under various conditions as described in Example 9.

Mean vector copy number (VCN) per transduced cell (cells expressing the transgene) also was determined at day 6 for each condition by real-time quantitative PCR (RT-qPCR) as described in Example 4. The results are presented in FIG. 9B.

Example 10: Effect of Centrifugation Time on Transduction Efficiency Using a Centrifugal Chamber 100×10$^6$ cells were subjected to transduction as described in Example 7, with various durations used for the incubation under centrifugation. Specifically, the total liquid volume used for the centrifugation in the processing cavity of the chamber was 70 mL (with the remaining 130 mL of the 200 mL total volume composed of air). Viral vector particles containing a vector encoding an anti-CD19 CAR were included in this volume at a ratio of 3.6 IU/cell. In each case, prior to transduction initiation, cells were collected, washed, isolated, cryopreserved, and activated as described in Example 11.

The spin for initiation of transduction was carried out at approximately 7400 rpm, corresponding to an approximately a 1600 g relative centrifugal force on the inner side wall of the processing chamber. The duration of the spin at this speed was 10 minutes for one condition and 60 minutes for the other.

Figure 10:
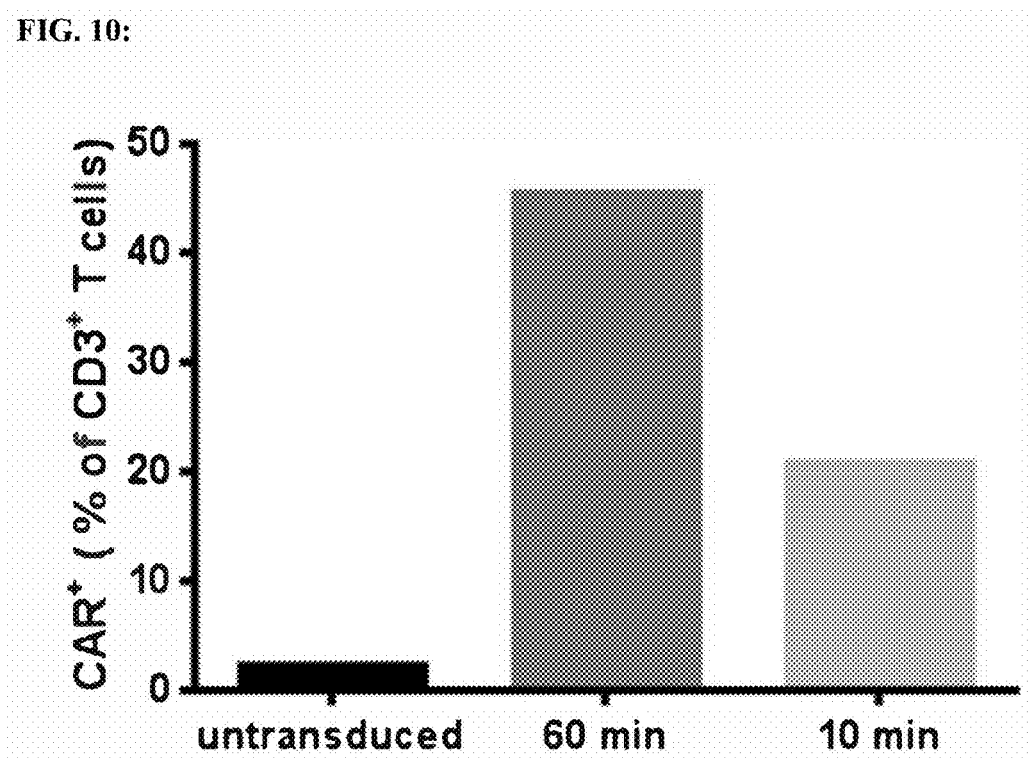
FIG. 10 shows transduction efficiency calculated as percentage of CD3$^+$ T Cells with surface expression of a CAR encoded by a viral vector following incubation under the indicated conditions as described in Example 10.

After the ~24-hour incubation, the cells were expanded in a Bioreactor System with perfusion. Transduction efficiency for the respective compositions was calculated on Day 6 as percentage of CD3$^+$ T Cells with surface expression of the encoded CAR detected as described in Example 1. An untransduced control also was assessed ("untransduced"). The results are shown in FIG. 10. As shown, in this study, greater transduction efficiency was observed following initiation of transduction of 100×10$^6$ cells in the processing cavity of the centrifuge chamber under centrifugation for 60 minutes as compared to 10 minutes.

Example 11: Preparation of Genetically Engineered Cells

This example describes an exemplary process which has been carried out to prepare, from a biological sample, genetically engineered T cells transduced with a nucleic acid encoded by a viral vector, according to certain embodiments provided herein. As described in individual examples, prior to the transduction steps carried out in studies described in various examples herein, some of the steps of this process were carried out, for example, collection, wash, cryopreservation, selection, and activation steps, as described in this example.

Various steps of the process were carried out within the processing cavity of a centrifugal chamber having a rigid, generally cylindrical side wall and a piston capable of moving within the chamber to vary the volume of the cavity (the processing cavity of a Sepax® centrifuge chamber contained within a single-use kit). Specifically, steps carried out in the chamber included cell washing, dilution/buffer-exchange, steps for affinity-based selection (e.g., incubation with immunospecific binding agents), transduction initiation, formulation, and steps for activation/expansion (e.g., incubation with stimulatory agent(s)).

1. Sample Collection and Leukapheresis

A human leukapheresis sample enriched in mononuclear cells was obtained from a whole blood sample from a subject using a leukapheresis collection system. The leukapheresis sample was stored sealed at 2-8° C., for no more than about 48 hours.

2. Leukapheresis Wash

The leukapheresis sample was sterilely transferred to a transfer pack. Cells of the leukapheresis sample were washed and resuspended in a buffer for use in affinity-based selection, the buffer containing PBS, EDTA, and human serum albumin. The wash was carried out within a sterile, single-use disposable kit sold by Biosafe SA for use in regenerative medicine, which included a centrifugal chamber (1), essentially as depicted in FIG. 7. The transfer pack containing the cells and a bag containing the buffer were sterilely connected to the kit, which was placed in association with a Sepax® 2 processing unit. The wash and resuspension were carried out using a standard cell wash protocol on the unit, with the cells retained in the processing cavity (7) of the centrifuge chamber at the end of the protocol, for subsequent incubation with reagents for affinity-based selection (see 3).

3. Affinity-Based Selection

For positive, immunoaffinity-based selection of T cells, the same automated program was continued to incubate the washed cells in the selection buffer with magnetic beads coupled to monoclonal antibodies specific for CD4 and CD8. The incubation was carried out at room temperature in the same centrifugal chamber (1) in which the cells were retained after the wash (see 2) described above. Specifically, the beads were mixed in selection buffer in a transfer pack, which then was sterilely connected at a Diluent Bag position of the single-use kit used for the wash step. A program was run on the Sepax® 2 unit which caused the bead mixture and selection buffer to be drawn into the chamber with the washed cells, and the contents of the chamber (total liquid volume 100 mL) to be mixed for 30 minutes, via a semi-continuous process. The mixing was carried out with repeated intervals, each including short duration (approximately 1 second) centrifugation at low speed (approximately 1700 rpm), followed by a short rest period (approximately 6 seconds).

At the end of the program, the Sepax® 2 unit caused pelleting of the cells and expulsion of excess buffer/beads into a bag at the Waste Bag position, washing of the pelleted cells, and resuspension in selection buffer. The wash was carried out on the Sepax® at an RCF at the internal wall of the cavity of approximately 200 g, for 180 seconds. The program caused the washed cells to be collected into a transfer pack placed at the Output Bag position in the exemplary kit shown in FIG. 7, the contents of which could be transferred via tubing lines to a column for magnetic separation, within a closed system. Thus, the cell wash and incubation with the affinity-based selection reagent was carried out entirely within the same closed, sterile system, by passing liquid and cells to and from the cavity of the centrifugal chamber. The ability to control and adjust liquid volumes and to mix the cells under rotation in the chamber allowed use of substantially less of the selection reagent per cell processed as compared to incubation in a tube with shaking or rotation.

The cells then were passed from the transfer pack, through a closed, sterile system of tubing lines and a separation column, in the presence of a magnetic field using standard methods, to separate cells that had bound to the CD4- and/or CD8-specific reagents. These magnetically-labeled cells then were collected in a transfer pack for further processing.

4. Cryopreservation

The transfer pack with the labeled, selected cells was sterilely-connected to a single-use disposable kit sold by Biosafe AS for regenerative medicine for use with the Sepax® 2 system. The kit was essentially as shown in FIG. 7, except that two ports, as opposed to one, were present at the position to which the Output Bag is attached in the exemplary system shown in FIG. 7, with a collection bag sterilely connected at each port; two ports, as opposed to one, were present at the position to which the Input Bag is connected in FIG. 7; and a single port, as opposed to two, were present at the position of Diluent Bags 1 and 2 in FIG. 7. A standard wash cycle was carried out on the Sepax® 2 unit to reduce the volume of the washed cells. A bag with cryomedia was sterilely connected to the kit and a dilution protocol run twice to transfer the cryomedia to the cell composition and expel the resulting composition into the two output cryopreservation bags. The cells in the cryopreservation bags were cryopreserved and stored in liquid nitrogen until further use.

5. Thaw and Activation

Cryopreserved cells for were thawed. The thawed cells were activated using an anti-CD3/CD28 reagent(s), generally at 37° C., for a period of time as indicated for individual studies. Prior to incubation with the reagent, the cells were washed and resuspended in complete media using the Sepax® 2 system, using a standard cell washing program and in a kit essentially as shown in FIG. 7. In the same kit, the cells were combined with the anti-CD3/28 reagent(s) in the cavity of the chamber by mixing with intervals of low-speed centrifugation and rest as described for bead incubation for selection for 30 minutes at room temperature. Following the incubation, the incubated material was transferred via the Sepax® 2 unit into an output cell culture bag, which then was incubated at 37° C. for the remainder of the activation period.

6. Transduction

Transduction was carried out in the centrifugal chamber integral to the kit, placed in association with the Sepax® processing unit, as described in Example 7, with specific details given in particular examples.

7. Expansion

In some cases, following transduction, cells were further incubated, generally at 37 degrees C., to allow for expansion.

8. Wash, Formulation

In some cases, the expanded and/or transduced cells were further washed, diluted, and/or formulated for testing, storage, and/or administration. In some examples, expanded and/or transduced cells were washed in the chamber integral to a single-use kit for use with the Sepax® 2 system, for example as described for cryopreservation. In some cases, a bag containing washed cells was sterilely connected to a kit such as shown in FIG. 7, or such a kit with a plurality of ports available for connection of containers, e.g., bags, at the Output Bag position shown in FIG. 7.

One example of such a multi-port output kit is shown in FIG. 11, which shows a plurality of ports (17), to one or more of which may be connected a container, such as a bag, for collection of output composition. The connection may be by sterile welding of the desired number of containers, depending for example, on the desired number of unit dosage form of the cells to produce by a given method. To generate the kit shown in FIG. 11, a multi-way tubing manifold with a plurality of ports (in the example shown in FIG. 11, eight) was sterilely welded to an output line of a single-use kit sold by Biosafe AS for regenerative medicine use. A desired number of plurality of output bags were sterilely connected to one or more, generally two or more, of these ports. In some examples, such bags were attached to fewer than all the ports. Clamps (5) were placed on the tubing lines preventing movement of fluid into the individual bags until desired. A bag containing the desired liquid, such as formulation, assay, and/or cryopreservation media, was sterilely connected to the kit and a dilution protocol run on the Sepax® 2 unit a plurality of times, with the user opening and closing the respective clamps leading to the appropriate number of bags, thereby generating an output composition in the desired formulation, split into the desired number of bags. In some embodiments, a single unit dose of cells was collected in each of the respected bags, in a formulation for administration to a subject, such as the subject from which the leukapheresis product was derived.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A transduction method comprising incubating, in an internal cavity of a centrifugal chamber, an input composition comprising cells and viral particles containing a recombinant viral vector, wherein:
   the centrifugal chamber comprises one or more openings comprising at least one opening that is capable of permitting intake of liquid into the internal cavity and expression of liquid from the internal cavity and at least one opening that is capable of permitting intake of gas into the internal cavity and expression of gas from the internal cavity;
   the internal cavity has variable volume, and the method comprises, prior to or during the incubation, effecting intake of a gas into the internal cavity to increase the volume of the internal cavity, the internal cavity comprising the input composition and the gas during at least a portion of the incubation;
   the centrifugal chamber is rotating around an axis of rotation during at least a portion of the incubation; and
   the method generates an output composition comprising a plurality of the cells transduced with the recombinant viral vector.

2. The method of claim 1, wherein the centrifugal chamber comprises a movable member capable of moving within the centrifugal chamber to vary the volume of the internal cavity, and the effecting the intake of the gas effects movement of the movable member.

3. The method of claim 2, wherein the movable member is capable of moving axially within the centrifugal chamber to vary the volume of the internal cavity.

4. The method of claim 2, wherein the movable member is a piston.

5. The method of claim 1, wherein the rotating comprises rotation at a relative centrifugal force at a surface layer of the cells that is from about 500 g to about 2500 g.

6. The method of claim 1, wherein the rotating is for a time that is from about 5 minutes to about 60 minutes.

7. The method of claim 1, wherein the maximum liquid volume of the input composition present in the internal cavity at any one time during the incubation is no more than about 5 milliliters per square inch of the maximum internal surface area of the internal cavity during the incubation.

8. The method of claim 1, wherein the number of cells in the input composition is no more than two times the number of the cells sufficient to form a monolayer on the inner surface of the internal cavity during the rotating.

9. The method of claim 1, wherein:
the rotating comprises rotation at a relative centrifugal force at a surface layer of the cells that is from about 500 g to about 2500 g; and
the number of cells in the input composition is no more than two times the number of the cells sufficient to form a monolayer on the inner surface of the internal cavity during the rotating.

10. The method of claim 1, wherein the input composition comprises at least or at least about 1 infectious unit of viral particles per one of the cells.

11. The method of claim 1, wherein the titer of viral particles is from about $1 \times 10^6$ IU/mL to about $1 \times 10^8$ IU/mL.

12. The method of claim 1, wherein the maximum total liquid volume of the input composition present in the internal cavity at any one time during the incubation is no more than 100 times the total volume of the cells in the input composition.

13. The method of claim 1, wherein:
the maximum liquid volume of the input composition present in the internal cavity at any one time during the incubation is no more than about 5 milliliters per square inch of the maximum internal surface area of the internal cavity during the incubation; and
the maximum total liquid volume of the input composition present in the internal cavity at any one time during the incubation is no more than 100 times the total volume of the cells in the input composition.

14. The method of claim 1, wherein the gas is air.

15. The method of claim 1, wherein the centrifugal chamber comprises a movable member capable of moving within the centrifugal chamber to vary the volume of the internal cavity, and the intake of the gas is effected by movement of the movable member.

16. The method of claim 1, wherein
the centrifugal chamber is integral to a closed system, the closed system comprising the centrifugal chamber, at least one tubing operably linked to the one or more openings of the centrifugal chamber via at least one connector, and at least one container operably linked to the at least one tubing line, whereby liquid and gas are permitted to move between the internal cavity and the at least one container via the at least one tubing line in at least one configuration of the closed system.

17. The method of claim 16, wherein:
the at least one container comprises at least one input container comprising the viral particles and the cells, each of the at least one input container comprising one or both of the viral particles and the cells; and
the method further comprises, prior to the incubation, effecting intake of the viral particles and the cells into the internal cavity, the intake of the viral particles and the cells comprising flowing of liquid from the at least one input container into the internal cavity through the at least one opening that is capable of permitting intake and expression of liquid.

18. The method of claim 16, wherein
the closed system further comprises a microbial filter, the intake of the gas into the internal cavity being effected by flow of the gas under sterile conditions through the microbial filter.

19. The method of claim 1, wherein the cells in the input composition comprise T cells or NK cells.

20. The method of claim 1, wherein the input composition further comprises one or more additional agents to promote transduction efficiency.

21. The method of claim 20, wherein the one or more additional agents is protamine sulfate.

22. The method of claim 1, wherein the recombinant viral vector encodes a recombinant receptor, which is thereby expressed by cells of the output composition.

23. The method of claim 22, wherein the recombinant receptor is a chimeric antigen receptor (CAR) or a transgenic T cell receptor (TCR).

24. The method of claim 1, wherein the recombinant viral vector is a recombinant lentiviral vector.

25. The method of claim 1, wherein the rotating is for a time that is greater than about 60 minutes.

26. The method of claim 18, wherein the intake of the gas into the internal cavity is effected by flow of the gas under sterile conditions through a syringe connected to the microbial filter.

* * * * *